United States Patent
Herzog et al.

(10) Patent No.: US 7,342,007 B2
(45) Date of Patent: Mar. 11, 2008

(54) LACTAMS AND USES THEREOF

(75) Inventors: Keith John Herzog, Wilmington, DE (US); Robert Jacobs, Research Triangle Park, NC (US); Jianxing Kang, Wilmington, DE (US); Thomas Richard Simpson, Wilmington, DE (US); James M Woods, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 224 days.

(21) Appl. No.: 10/549,271

(22) PCT Filed: Mar. 10, 2004

(86) PCT No.: PCT/SE2004/000350

§ 371 (c)(1),
(2), (4) Date: Sep. 13, 2005

(87) PCT Pub. No.: WO2004/080983

PCT Pub. Date: Sep. 23, 2004

(65) Prior Publication Data

US 2006/0183732 A1 Aug. 17, 2006

(51) Int. Cl.
C07D 243/24 (2006.01)
C07D 223/16 (2006.01)
C07D 409/12 (2006.01)
A61K 31/55 (2006.01)
A61P 25/28 (2006.01)

(52) U.S. Cl. .................. 514/212.03; 540/527
(58) Field of Classification Search ........... 540/527; 514/212.03
See application file for complete search history.

(56) References Cited

U.S. PATENT DOCUMENTS 5,936,065 A 8/1999 Arrhenius et al.
2006/0089346 A1* 4/2006 Becker et al. ......... 514/211.03

FOREIGN PATENT DOCUMENTS

| WO | WO 90/09162 | 8/1990 |
|---|---|---|
| WO | WO 97/24339 | 7/1997 |
| WO | WO 98/17680 | 4/1998 |
| WO | WO 98/28268 | 7/1998 |
| WO | WO 99/67221 | 12/1999 |
| WO | WO 00/02903 | 1/2000 |
| WO | WO 00/07995 | 2/2000 |
| WO | WO 01/68655 | 9/2001 |
| WO | WO 01/72324 | 10/2001 |
| WO | 2004031154 | 4/2004 |

OTHER PUBLICATIONS

Petersen et al., "Practice parameter: early detection of dementia: mild cognitive impairment (an evidence-based review). Report of the Quality Standards Subcommittee of the American Academy of Neurology," *Neurology* (2001) 56(9):1133-1142.

Ritchie et al., "Classification criteria for mild cognitive impairment: a population-based validation study," *Neurology* (2001) 56(1):37-42.

Nitsch "Immunotherapy of Alzheimer Disease," *Alzheimer Dis Assoc Disord* (2004) 18(4):185-189.

Marjaux et al., "γ-Secretase inhibitors: still in the running as Alzheimer's therapeutics," *Drug Discovery Today: Therapeutic Strategies* (2004) 1(1):1-6.

Heinrikson "Secretases," *Biological Chemistry* Chapter 4, pp. 7-10, Elsevier Ltd., Oxford, UK (2004).

* cited by examiner

*Primary Examiner*—Bruck Kifle
(74) *Attorney, Agent, or Firm*—Pepper Hamilton LLP

(57) ABSTRACT

This invention relates to novel compounds having formula (I) to their pharmaceutical compositions and to their methods of use. These novel compounds inhibit secretase and thereby inhibit the production of amyloid β protein, thereby acting to prevent the formation of neurological deposits of amyloid protein. The present invention relates to the treatment of neurological disorders related to amyloid β-protein production such as Alzheimer's disease

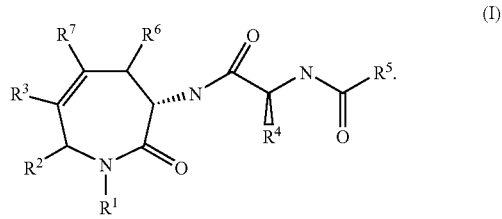

40 Claims, No Drawings

LACTAMS AND USES THEREOF

CROSS-REFERENCE TO RELATED APPLICATIONS

This application is the U.S. National Stage filing of International Application Ser. No. PCT/SE2004/000350 filed Mar. 10, 2004, which claims priority to U.S. application Ser. No. 60/459,416 filed Apr. 1, 2003, and U.S. application Ser. No. 60/455,100 filed Mar. 14, 2003, each of which is incorporated herein by reference in its entirety.

FIELD OF THE INVENTION

The present invention relates to novel lactams, their pharmaceutical compositions and methods of use. In addition, the present invention relates to therapeutic methods for the treatment and prevention of various diseases especially Alzheimer's disease.

BACKGROUND OF THE INVENTION

Alzheimer's Disease (AD) is a progressive, neurodegenerative disease characterized clinically by progressive loss of memory, cognition, reasoning, judgment and emotionally stability. AD is a common cause of dementia in humans and a leading cause of death in the United States. AD has been observed in races and ethnic groups worldwide and presents a major public health problem throughout the world. No treatment that effectively prevents AD or reverses the clinical symptoms and underlying pathophysiology is currently available and the disease is currently considered among experts to be incurable.

Dementia, for purposes of the present invention includes Alzheimer's disease (AD), vascular dementia and mixed cases. The early stages of dementia has to some degree been elucidated and defined. For example, studies have established a group of individuals that are at risk of developing dementia. These individuals suffer from mild cognitive impairment (MCI). MCI refers to a clinical state wherein the individuals are memory impaired but do not meet the clinical criteria for dementia. Petersen, et al., *Practice parameter: Early detection of dementia: Mild cognitive impairment (an evidence-based review)*, Neurology, 56:1133-1142 (2001). The criteria used to establish MCI is as follows: 1) the presence of a subjective memory complaint, preferably corroborated by an informant; 2) preserved general intellectual functioning as estimated by performance on a vocabulary test; 3) demonstration of a memory impairment by cognitive testing; 4) intact activities of daily living; and 5) absence of dementia.

Another group of individuals that are at risk for developing dementia are those in a pre-demented state found with age associated cognitive decline (AACD) which is generally defined by a decline of more than one standard deviation in any are of cognitive functioning in comparison with age matched controls. K. Ritchie et al., *Classification criteria for mild cognitive impairment: A population-based validation study*, Neurology 56:3742 (2001). Ritchie et al., argues that AACD has a higher predictive validity for dementia onset. Id. at 40.

The histopathological manifestations of AD are characteristic lesions known as amyloid (or senile) plaques and neurofibrillar tangles that are found in the regions of the brain associated with memory, reasoning and cognition. Similar alterations are observed in patients with Trisomy 21 (Down's syndrome) and hereditary cerebral hemorrhage with amyloidosis of the Dutch-type.

The major constituent of amyloid plaques is amyloid β protein. Amyloid β protein is derived from the proteolytic cleavage of amyloid precursor protein (APP). Processing of APP to amyloid β protein and other APP fragments is governed by a group of enzymes known as secretases. One type of secretase, γ-secretase, is responsible for the protein type of cleavage that produces amyloid β protein. Compounds that inhibit either β or γ secretase activity, either directly or indirectly would reduce the production of amyloid β protein resulting in the treatment or prevention of disorders associated with amyloid β protein. Thus there is a continuing need for compounds that inhibit amyloid β protein production. The present invention meets this and related needs by providing a family of novel compounds and related methods of use.

SUMMARY OF THE INVENTION

In accordance with the present invention, the applicants have hereby discovered novel compounds that inhibit γ secretase and thereby inhibit the production of amyloid β protein. The invention includes pharmaceutically acceptable salts or prodrugs of such compounds. Also in accordance with the present invention applicants provide pharmaceutical compositions and a method to use invention compounds in the treatment of dementia, including Alzheimer's disese, mild cognitive impairment and other degenerative neurological disorders.

DETAILED DESCRIPTION OF THE INVENTION

In a particular embodiment the present invention provides a compound having formula (I):

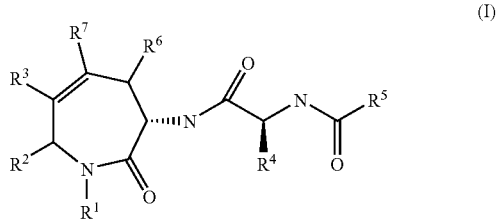

wherein:

$R^1$ is selected from H, optionally substituted $C_{1-3}$alkylaryl, optionally substituted $C_{1-3}$alkylheterocycle, optionally substituted alkyl, optionally substituted cycloalkyl, $C_{2-4}$alkylNR$^a$R$^b$, or $C_{1-4}$alkylCOR$^d$, wherein all such optional substitutions are made with 0, 1, 2 or 3 R$^e$;

$R^a$ and $R^b$ are, at each occurrence independently selected from H, $C_{1-4}$alkyl or $C_{5-6}$cycloalkyl, or R$^a$ and R$^b$ and the N to which they are attached in combination form a 5 or 6-membered N-linked heterocycle having 2 nitrogen or, 1 nitrogen and 1 oxygen, ring atoms, wherein the non-linked nitrogen is substituted with R$^c$;

$R^c$ is, at each occurrence independently selected from H, $C_{1-3}$alkyl, or substituted phenyl with 0, 1, 2, or 3 R$^e$;

$R^d$ is, at each occurrence independently selected from $C_{1-3}$alkyl, $C_{1-3}$alkoxy, or NR$^a$R$^b$;

$R^e$ is, at each occurrence independently selected from OH, F, Cl, Br, I, CN, $NO_2$, $CF_3$, $C_{1-6}$alkyl, or $C_{1-6}$alkoxy;

$R^2$, $R^3$, $R^6$ and $R^7$ are independently selected from H, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, optionally substituted $C_{1-3}$alkylaryl, optionally substituted $C_{1-3}$alkylheterocycle, optionally substituted $C_{1-6}$alkyl, or optionally substituted $C_{3-6}$ cycloalkyl, wherein all such optional substitutions are made with 0, 1, 2, or 3 $R^e$ moieties, with the requirement that one or more of $R^2$, $R^3$, $R^6$ and $R^7$ are aromatic or heteroaromatic;

$R^4$ is H, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, $C_{1-6}$alkyl, $C_{3-6}$ cycloalkyl, or $CR^9R^{10}R^{11}$;

$R^5$ is —$C_{1-6}$alkyl, —$C_{1-3}$alkyl$R^{12}$ or $CH(OH)R^{13}$;

$R^9$, $R^{10}$ and $R^{11}$ are, at each occurrence independently selected from H, F, $C_{1-4}$alkyl, OH, $OCH_3$, SH, $SCH_3$, $CH_2SCH_3$;

$R^{12}$ is phenyl substituted with 0, 1, 2 or 3 $R^e$;

$R^{13}$ is $C_{1-6}$alkyl or $R^{12}$;

or a pharmaceutically acceptable salt thereof.

In a particular embodiment the present invention provides a compound having formula (I) wherein:

$R^1$ is selected from H, or optionally substituted alkyl, wherein such optional substitution is made with 0, 1, or 2 substituents selected from $C_{1-6}$cycloalkyl, $C_{1-6}$cycloalkoxy, or phenyl;

$R^2$, $R^3$, $R^6$ and $R^7$ are independently selected from H, or optionally substituted 6-membered aromatic, wherein such optional substitution is made with 0, 1, 2, or 3 $R^e$ moieties, with the requirement that one or more of $R^2$, $R^3$, $R^6$ and $R^7$ are aromatic;

$R^4$ is H, or $C_{1-6}$alkyl;

$R^5$ is —$C_{1-6}$alkyl, —$C_{1-3}$alkyl$R^{12}$;

$R^{12}$ is phenyl substituted with 0, 1, 2 or 3 $R^e$;

$R^e$ is, at each occurrence independently selected from OH, F, Cl, Br, I, CN, $NO_2$, $CF_3$, $C_{1-6}$alkyl, or $C_{1-6}$alkoxy;

or a pharmaceutically acceptable salt thereof.

In a particular embodiment the present invention provides a compound having formula (I) wherein:

$R^1$ is selected from H, —$C_{1-6}$alkyl, —$(CH_2)_2OCH_3$, —$CH_2$-phenyl, —$CH_2C_{1-6}$cycloalkyl;

$R^2$, $R^3$, $R^6$ and $R^7$ are independently selected from H, or a substituted phenyl, wherein such substitutent is selected from 1, 2, or 3 of the following F, Cl, Br, I or $OCH_3$;

$R^4$ is H, or $C_{1-6}$alkyl;

$R^5$ is —$C_{1-6}$alkyl, —$C_{1-3}$alkyl$R^{12}$ wherein $R^{12}$ is a substituted phenyl, wherein such substitutent is selected from 1, 2 or 3 of the following F, Cl, Br, I or $OCH_3$;

or a pharmaceutically acceptable salt thereof.

In a particular embodiment the present invention provides a compound having formula (I) wherein:

$R^1$ is —$C_{1-3}$alkyl, —$CH_2C_{1-4}$cycloalkyl.

In a particular embodiment the present invention provides a compound having formula (I) wherein:

$R^1$ is methyl, or —$CH_2$-cyclopropane.

In a particular embodiment the present invention provides a compound having formula (I) wherein:

$R^e$ is, at each occurrence independently selected from F, Cl, $CF_3$, $C_{1-6}$alkyl, or $C_{1-6}$alkoxy.

In a particular embodiment the present invention provides a compound having formula (I) wherein:

$R^2$ is an optionally substituted phenyl, wherein such optional substitution is made with 0, 1, 2, or 3 $R^e$ moieties.

In a particular embodiment the present invention provides a compound having formula (I) wherein:

$R^3$, $R^6$ and $R^7$ are H.

In a particular embodiment the present invention provides a compound having formula (I) wherein:

$R^4$ is $C_{1-6}$alkyl.

In a particular embodiment the present invention provides a compound having formula (I) wherein:

$R^5$ is —$C_{1-6}$alkyl, —$C_{1-3}$alkyl$R^{12}$ wherein $R^{12}$ is a substituted phenyl, wherein such substitutent is selected from 1, 2 or 3 of the following F, Cl, Br, I or $OCH_3$.

In a particular embodiment the present invention provides a compound having formula (I) selected from:

$N^2$-[(3,5-difluorophenyl)acetyl]-$N^1$-[(3S,7S)-1-methyl-2-oxo-7-phenyl-2,3,4,7-tetrahydro-1H-azepin-3-yl]-L-alaninamide;

$N^1$-[(3,5-difluorophenyl)acetyl]-$N^1$-[(3S,7R)-1-methyl-2-oxo-7-phenyl-2,3,4,7-tetrahydro-1H-azepin-3-yl]-L-alaninamide;

$N^1$-[(3S,7S)-1-(cyclopropylmethyl)-2-oxo-7-phenyl-2,3,4,7-tetrahydro-1H-azepin-3-yl]-$N^2$-[(3,5-difluorophenyl)acetyl]-L-alaninamide;

$N^1$-[(3S,7R)-1-(cyclopropylmethyl)-2-oxo-7-phenyl-2,3,4,7-tetrahydro-1H-azepin-3-yl]-$N^2$-[(3,5-difluorophenyl)acetyl]-L-alaninamide;

$N^1$-[(3S,7S)-1-benzyl-2-oxo-7-phenyl-2,3,4,7-tetrahydro-1H-azepin-3-yl]-$N^2$-[(3,5-difluorophenyl)acetyl]-L-alaninamide;

$N^1$-[(3S,7R)-1-benzyl-2-oxo-7-phenyl-2,3,4,7-tetrahydro-1H-azepin-3-yl]-$N^2$-[(3,5-difluorophenyl)acetyl]-L-alaninamide;

$N^2$-[(3,5-difluorophenyl)acetyl]-$N^1$-[(3S,7S)-1-(2-methoxyethyl)-2-oxo-7-phenyl-2,3,4,7-tetrahydro-1H-azepin-3-yl]-L-alaninamide;

$N^2$-[(3,5-difluorophenyl)acetyl]-$N^1$-[(3S,7R)-1-(2-methoxyethyl)-2-oxo-7-phenyl-2,3,4,7-tetrahydro-1H-azepin-3-yl]-L-alaninamide;

$N^2$-[(2S)-2-hydroxy-4-methylpentanoyl]-$N^1$-[(3S,7S)-1-(2-methoxyethyl)-2-oxo-7-phenyl-2,3,4,7-tetrahydro-1H-azepin-3-yl]-L-leucinamide;

$N^1$-[(3R,7S)-1 cyclopentyl-2-oxo-7-phenyl-2,3,4,7-tetrahydro-1H-azepin-3-yl]-$N^2$-[(3,5-difluorophenyl)acetyl]-L-alaninamide;

$N^1$-[(3S,7S)-1-cyclopentyl-2-oxo-7-phenyl-2,3,4,7-tetrahydro-1H-azepin-3-yl]-$N^2$-[(3,5-difluorophenyl)acetyl]-L-alaninamide;

$N^1$-[(3R,7S)-1-isobutyl-2-oxo-7-phenyl-2,3,4,7-tetrahydro-1H-azepin-3-yl]-$N^2$-[(3,5-difluorophenyl)acetyl]-L-alaninamide;

$N^1$-[(3S,7S)-1-isobutyl-2-oxo-7-phenyl-2,3,4,7-tetrahydro-1H-azepin-3-yl]-$N^2$-[(3,5-difluorophenyl)acetyl]-L-alaninamide;

$N^1$-[(3S,7S)-1-(cyclopropylmethyl)-7-(4-fluorophenyl)-2-oxo-2,3,4,7-tetrahydro-1H-azepin-3-yl]-$N^2$-[(3,5-difluorophenyl)acetyl]-L-alaninamide;

$N^1$-[(3R,7S)-1-(cyclopropylmethyl)-7-(4-fluorophenyl)-2-oxo-2,3,4,7-tetrahydro-1H-azepin-3-yl]-$N^2$-[(3,5-difluorophenyl)acetyl]-L-alaninamide $N^1$-[(3S,7S)-1-(cyclopropylmethyl)-7-(4-methoxyphenyl)-2-oxo-2,3,4,7-tetrahydro-1H-azepin-3-yl]-$N^2$-[(3,5-difluorophenyl)acetyl]-L-alaninamide (11)

$N^1$-[(3R,7S)-1-(cyclopropylmethyl)-7-(4-methoxyphenyl)-2-oxo-2,3,4,7-tetrahydro-1H-azepin-3-yl]-$N^2$-[(3,5-difluorophenyl)acetyl]-L-alaninamide;

$N^1$-[(3S,7S)-1-(cyclopropylmethyl)-7-(4-methoxyphenyl)-2-oxo-2,3,4,7-tetrahydro-1H-azepin-3-yl]-$N^2$-[(2S)-2-hydroxy-4-methylpentanoyl]-L-leucinamide;

N²-[(2S)-2-(3,5-difluorophenyl)-2-hydroxyacetyl]-N¹-[(3S,7S)-1-methyl-2-oxo-7-phenyl-2,3,4,7-tetrahydro-1H-azepin-3-yl]-L-alaninamide;

N²-[(2R)-2-(3,5-difluorophenyl)-2-hydroxyacetyl]-N¹-[(3S,7S)-1-methyl-2-oxo-7-phenyl-2,3,4,7-tetrahydro-1H-azepin-3-yl]-L-alaninamide;

N²-[(2S)-2-(3,5-difluorophenyl)-2-hydroxyacetyl]-N¹-[(3S,7S)-2-oxo-7-phenyl-2,3,4,7-tetrahydro-1H-azepin-3-yl]-L-alaninamide;

N²-[(2R)-2-(3,5-difluorophenyl)-2-hydroxyacetyl]-N¹-[(3S,7S)-2-oxo-7-phenyl-2,3,4,7-tetrahydro-1H-azepin-3-yl]-L-alaninamide;

N²-[(3,5-difluorophenyl)acetyl]-N¹-[(3S)-1-methyl-2-oxo-6-phenyl-2,3,4,7-tetrahydro-1H-azepin-3-yl]-L-alaninamide;

N²-[(3,5-difluorophenyl)acetyl]-N¹-[(3S)-2-oxo-6-phenyl-2,3,4,7-tetrahydro-1H-azepin-3-yl]-L-alaninamide;

N²-[(2S)-2-(3,5-difluorophenyl)-2-hydroxyacetyl]-N¹-[(3S)-1-methyl-2-oxo-6-phenyl-2,3,4,7-tetrahydro-1H-azepin-3-yl]-L-alaninamide;

N²-[(2R)-2-(3,5-difluorophenyl)-2-hydroxyacetyl]-N¹-[(3S)-1-methyl-2-oxo-6-phenyl-2,3,4,7-tetrahydro-1H-azepin-3-yl]-L-alaninamide;

N²-[(2R)-2-(3,5-difluorophenyl)-2-hydroxyacetyl]-N¹-[(3S)-2-oxo-6-phenyl-2,3,4,7-tetrahydro-1H-azepin-3-yl]-L-alaninamide;

N²-[(2S)-2-(3,5-difluorophenyl)-2-hydroxyacetyl]-N¹-[(3S)-2-oxo-6-phenyl-2,3,4,7-tetrahydro-1H-azepin-3-yl]-L-alaninamide;

N²-[(3,5-difluorophenyl)acetyl]-N¹-[(3S)-1-methyl-2-oxo-5-phenyl-2,3,4,7-tetrahydro-1H-azepin-3-yl]-L-alaninamide;

N²-[(3,5-difluorophenyl)acetyl]-N¹-[(3S)-2-oxo-5-phenyl-2,3,4,7-tetrahydro-1H-azepin-3-yl]-L-alaninamide;

N²-[(2S)-2-(3,5-difluorophenyl)-2-hydroxyacetyl]-N¹-[(3S)-1-methyl-2-oxo-5-phenyl-2,3,4,7-tetrahydro-1H-azepin-3-yl]-L-alaninamide;

N²-[(2R)-2-(3,5-difluorophenyl)-2-hydroxyacetyl]-N¹-[(3S)-1-methyl-2-oxo-5-phenyl-2,3,4,7-tetrahydro-1H-azepin-3-yl]-L-alaninamide;

N²-[(2R)-2-(3,5-difluorophenyl)-2-hydroxyacetyl]-N¹-[(3S)-2-oxo-5-phenyl-2,3,4,7-tetrahydro-1H-azepin-3-yl]-L-alaninamide;

N²-[(2S)-2-(3,5-difluorophenyl)-2-hydroxyacetyl]-N¹-[(3S)-2-oxo-5-phenyl-2,3,4,7-tetrahydro-1H-azepin-3-yl]-L-alaninamide;

N²-[(3,5-difluorophenyl)acetyl]-N¹-[(3S,4S)-1-methyl-2-oxo-4-phenyl-2,3,4,7-tetrahydro-1H-azepin-3-yl]-L-alaninamide;

N²-[(3,5-difluorophenyl)acetyl]-N¹-[(3S,4S)-2-oxo-4-phenyl-2,3,4,7-tetrahydro-1H-azepin-3-yl]-L-alaninamide;

N²-[(2S)-2-(3,5-difluorophenyl)-2-hydroxyacetyl]-N¹-[(3S,4S)-1-methyl-2-oxo-4-phenyl-2,3,4,7-tetrahydro-1H-azepin-3-yl]-L-alaninamide;

N²-[(2R)-2-(3,5-difluorophenyl)-2-hydroxyacetyl]-N¹-[(3S,4S)-1-methyl-2-oxo-4-phenyl-2,3,4,7-tetrahydro-1H-azepin-3-yl]-L-alaninamide;

N²-[(2R)-2-(3,5-difluorophenyl)-2-hydroxyacetyl]-N¹-[(3S,4S)-2-oxo-4-phenyl-2,3,4,7-tetrahydro-1H-azepin-3-yl]-L-alaninamide;

N²-[(2S)-2-(3,5-difluorophenyl)-2-hydroxyacetyl]-N¹-[(3S,4S)-2-oxo-4-phenyl-2,3,4,7-tetrahydro-1H-azepin-3-yl]-L-alaninamide;

N²-[(3,5-difluorophenyl)acetyl]-N²-[(3S,4R)-1-methyl-2-oxo-4-phenyl-2,3,4,7-tetrahydro-1H-azepin-3-yl]-L-alaninamide;

N²-[(3,5-difluorophenyl)acetyl]-N¹-[(3S,4R)-2-oxo-4-phenyl-2,3,4,7-tetrahydro-1H-azepin-3-yl]-L-alaninamide;

N²-[(2S)-2-(3,5-difluorophenyl)-2-hydroxyacetyl]-N¹-[(3S,4R)-1-methyl-2-oxo-4-phenyl-2,3,4,7-tetrahydro-1H-azepin-3-yl]-L-alaninamide;

N²-[(2R)-2-(3,5-difluorophenyl)-2-hydroxyacetyl]-N¹-[(3S,4R)-1-methyl-2-oxo-4-phenyl-2,3,4,7-tetrahydro-1H-azepin-3-yl]-L-alaninamide;

N²-[(2S)-2-(3,5-difluorophenyl)-2-hydroxyacetyl]-N¹-[(3S,4R)-2-oxo-4-phenyl-2,3,4,7-tetrahydro-1H-azepin-3-yl]-L-alaninamide;

N²-[(2R)-2-(3,5-difluorophenyl)-2-hydroxyacetyl]-N¹-[(3S,4R)-2-oxo-4-phenyl-2,3,4,7-tetrahydro-1H-azepin-3-yl]-L-alaninamide;

N²-[(3,5-difluorophenyl)acetyl]-N¹-[(3S,4S,7S)-1-methyl-2-oxo-4,7-diphenyl-2,3,4,7-tetrahydro-1H-azepin-3-yl]-L-alaninamide;

N²-[(3,5-difluorophenyl)acetyl]-N¹-[(3S,4S,7S)-2-oxo-4,7-diphenyl-2,3,4,7-tetrahydro-1H-azepin-3-yl]-L-alaninamide;

N²-[(2S)-2-(3,5-difluorophenyl)-2-hydroxyacetyl]-N¹-[(3S,4S,7S)-1-methyl-2-oxo-4,7-diphenyl-2,3,4,7-tetrahydro-1H-azepin-3-yl]-L-alaninamide;

N²-[(2R)-2-(3,5-difluorophenyl)-2-hydroxyacetyl]-N¹-[(3S,4S,7S)-1-methyl-2-oxo-4,7-diphenyl-2,3,4,7-tetrahydro-1H-azepin-3-yl]-L-alaninamide;

N²-[(2S)-2-(3,5-difluorophenyl)-2-hydroxyacetyl]-N¹-[(3S,4S,7S)-2-oxo-4,7-diphenyl-2,3,4,7-tetrahydro-1H-azepin-3-yl]-L-alaninamide;

N²-[(2R)-2-(3,5-difluorophenyl)-2-hydroxyacetyl]-N¹-[(3S,4S,7S)-2-oxo-4,7-diphenyl-2,3,4,7-tetrahydro-1H-azepin-3-yl]-L-alaninamide;

N²-[(3,5-difluorophenyl)acetyl]-N¹-[(3S,4R,7S)-1-methyl-2-oxo-4,7-diphenyl-2,3,4,7-tetrahydro-1H-azepin-3-yl]-L-alaninamide;

N²-[(3,5-difluorophenyl)acetyl]-N¹-[(3S,4R,7S)-2-oxo-4,7-diphenyl-2,3,4,7-tetrahydro-1H-azepin-3-yl]-L-alaninamide;

N²-[(2S)-2-(3,5-difluorophenyl)-2-hydroxyacetyl]-N¹-[(3S,4R,7S)-1-methyl-2-oxo-4,7-diphenyl-2,3,4,7-tetrahydro-1H-azepin-3-yl]-L-alaninamide;

N²-[(2R)-2-(3,5-difluorophenyl)-2-hydroxyacetyl]-N¹-[(3S,4R,7S)-1-methyl-2-oxo-4,7-diphenyl-2,3,4,7-tetrahydro-1H-azepin-3-yl]-L-alaninamide;

N²-[(2S)-2-(3,5-difluorophenyl)-2-hydroxyacetyl]-N¹-[(3S,4R,7S)-2-oxo-4,7-diphenyl-2,3,4,7-tetrahydro-1H-azepin-3-yl]-L-alaninamide;

N²-[(2R)-2-(3,5-difluorophenyl)-2-hydroxyacetyl]-N¹-[(3S,4R,7S)-2-oxo-4,7-diphenyl-2,3,4,7-tetrahydro-1H-azepin-3-yl]-L-alaninamide;

N²-[(3,5-difluorophenyl)acetyl]-N¹-[(3S,4R,7R)-1-methyl-2-oxo-4,7-diphenyl-2,3,4,7-tetrahydro-1H-azepin-3-yl]-L-alaninamide;

N²-[(3,5-difluorophenyl)acetyl]-N¹-[(3S,4R,7R)-2-oxo-4,7-diphenyl-2,3,4,7-tetrahydro-1H-azepin-3-yl]-L-alaninamide;

N²-[(2S)-2-(3,5-difluorophenyl)-2-hydroxyacetyl]-N¹-[(3S,4R,7R)-1-methyl-2-oxo-4,7-diphenyl-2,3,4,7-tetrahydro-1H-azepin-3-yl]-L-alaninamide;

N²-[(2R)-2-(3,5-difluorophenyl)-2-hydroxyacetyl]-N¹-[(3S,4R,7R)-1-methyl-2-oxo-4,7-diphenyl-2,3,4,7-tetrahydro-1H-azepin-3-yl]-L-alaninamide;

N²-[(2S)-2-(3,5-difluorophenyl)-2-hydroxyacetyl]-N¹-[(3S,4R,7R)-2-oxo-4,7-diphenyl-2,3,4,7-tetrahydro-1H-azepin-3-yl]-L-alaninamide;

$N^2$-[(2R)-2-(3,5-difluorophenyl)-2-hydroxyacetyl]-$N^1$-[(3S, 4R,7R)-2-oxo-4,7-diphenyl-2,3,4,7-tetrahydro-1H-azepin-3-yl]-L-alaninamide;

$N^2$-[(3,5-difluorophenyl)acetyl]-$N^1$-[(3S,7R)-1-methyl-2-oxo-5,7-diphenyl-2,3,4,7-tetrahydro-1H-azepin-3-yl]-L-alaninamide;

$N^2$-[(3,5-difluorophenyl)acetyl]-$N^1$-[(3S,7R)-2-oxo-5,7-diphenyl-2,3,4,7-tetrahydro-1H-azepin-3-yl]-L-alaninamide;

$N^2$-[(2S)-2-(3,5-difluorophenyl)-2-hydroxyacetyl]-$N^1$-[(3S, 7R)-1-methyl-2-oxo-5,7-diphenyl-2,3,4,7-tetrahydro-1H-azepin-3-yl]-L-alaninamide;

$N^2$-[(2R)-2-(3,5-difluorophenyl)-2-hydroxyacetyl]-$N^1$-[(3S, 7R)-1-methyl-2-oxo-5,7-diphenyl-2,3,4,7-tetrahydro-1H-azepin-3-yl]-L-alaninamide;

$N^2$-[(2S)-2-(3,5-difluorophenyl)-2-hydroxyacetyl]-$N^1$-[(3S, 7R)-2-oxo-5,7-diphenyl-2,3,4,7-tetrahydro-1H-azepin-3-yl]-L-alaninamide;

$N^2$-[(2R)-2-(3,5-difluorophenyl)-2-hydroxyacetyl]-$N^1$-[(3S, 7R)-2-oxo-5,7-diphenyl-2,3,4,7-tetrahydro-1H-azepin-3-yl]-L-alaninamide;

$N^2$-[(3,5-difluorophenyl)acetyl]-$N^1$-[(3S,7S)-1-methyl-2-oxo-5,7-diphenyl-2,3,4,7-tetrahydro-1H-azepin-3-yl]-L-alaninamide;

$N^2$-[(3,5-difluorophenyl)acetyl]-$N^1$-[(3S,7S)-2-oxo-5,7-diphenyl-2,3,4,7-tetrahydro-1H-azepin-3-yl]-L-alaninamide;

$N^2$-[(2S)-2-(3,5-difluorophenyl)-2-hydroxyacetyl]-$N^1$-[(3S, 7S)-1-methyl-2-oxo-5,7-diphenyl-2,3,4,7-tetrahydro-1H-azepin-3-yl]-L-alaninamide;

$N^2$-[(2R)-2-(3,5-difluorophenyl)-2-hydroxyacetyl]-$N^1$-[(3S, 7S)-1-methyl-2-oxo-5,7-diphenyl-2,3,4,7-tetrahydro-1H-azepin-3-yl]-L-alaninamide;

$N^2$-[(2S)-2-(3,5-difluorophenyl)-2-hydroxyacetyl]-$N^1$-[(3S, 7S)-2-oxo-5,7-diphenyl-2,3,4,7-tetrahydro-1H-azepin-3-yl]-L-alaninamide;

$N^2$-[(2R)-2-(3,5-difluorophenyl)-2-hydroxyacetyl]-1-[(3S, 7S)-2-oxo-5,7-diphenyl-2,3,4,7-tetrahydro-1H-azepin-3-yl]-L-alaninamide;

$N^2$-[(3,5-difluorophenyl)acetyl]-$N^1$-[(3S,4R)-1-methyl-2-oxo-4,6-diphenyl-2,3,4,7-tetrahydro-1H-azepin-3-yl]-L-alaninamide;

$N^2$-[(3,5-difluorophenyl)acetyl]-$N^1$-[(3S,4R)-2-oxo-4,6-diphenyl-2,3,4,7-tetrahydro-1H-azepin-3-yl]-L-alaninamide;

$N^2$-[(2S)-2-(3,5-difluorophenyl)-2-hydroxyacetyl]-$N^1$-[(3S, 4R)-1-methyl-2-oxo-4,6-diphenyl-2,3,4,7-tetrahydro-1H-azepin-3-yl]-L-alaninamide;

$N^2$-[(2R)-2-(3,5-difluorophenyl)-2-hydroxyacetyl]-$N^1$-[(3S, 4R)-1-methyl-2-oxo-4,6-diphenyl-2,3,4,7-tetrahydro-1H-azepin-3-yl]-L-alaninamide;

$N^2$-[(2S)-2-(3,5-difluorophenyl)-2-hydroxyacetyl]-$N^1$-[(3S, 4R)-2-oxo-4,6-diphenyl-2,3,4,7-tetrahydro-1H-azepin-3-yl]-L-alaninamide;

$N^2$-[(2R)-2-(3,5-difluorophenyl)-2-hydroxyacetyl]-$N^1$-[(3S, 4R)-2-oxo-4,6-diphenyl-2,3,4,7-tetrahydro-1H-azepin-3-yl]-L-alaninamide;

$N^2$-[(3,5-difluorophenyl)acetyl]-$N^1$-[(3S,4S)-1-methyl-2-oxo-4,6-diphenyl-2,3,4,7-tetrahydro-1H-azepin-3-yl]-L-alaninamide;

$N^2$-[(3,5-difluorophenyl)acetyl]-$N^1$-[(3S,4S)-2-oxo-4,6-diphenyl-2,3,4,7-tetrahydro-1H-azepin-3-yl]-L-alaninamide;

$N^2$-[(2S)-2-(3,5-difluorophenyl)-2-hydroxyacetyl]-$N^1$-[(3S, 4S)-1-methyl-2-oxo-4,6-diphenyl-2,3,4,7-tetrahydro-1H-azepin-3-yl]-L-alaninamide;

$N^2$-[(2R)-2-(3,5-difluorophenyl)-2-hydroxyacetyl]-$N^1$-[(3S, 4S)-1-methyl-2-oxo-4,6-diphenyl-2,3,4,7-tetrahydro-1H-azepin-3-yl]-L-alaninamide;

$N^2$-[(2S)-2-(3,5-difluorophenyl)-2-hydroxyacetyl]-$N^1$-[(3S, 4S)-2-oxo-4,6-diphenyl-2,3,4,7-tetrahydro-1H-azepin-3-yl]-L-alaninamide;

$N^2$-[(2R)-2-(3,5-difluorophenyl)-2-hydroxyacetyl]-$N^1$-[(3S, 4S)-2-oxo-4,6-diphenyl-2,3,4,7-tetrahydro-1H-azepin-3-yl]-L-alaninamide.

In a particular embodiment the present invention provides a compound having formula (II):

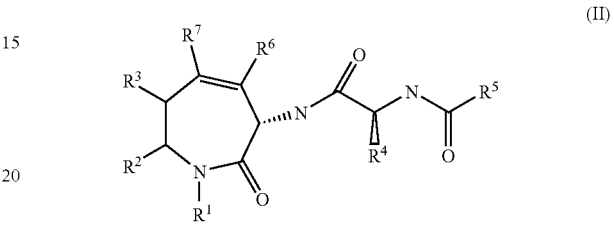

wherein:

$R^1$ is selected from H, optionally substituted $C_{1-3}$alkylaryl, optionally substituted $C_{1-3}$alkylheterocycle, optionally substituted alkyl, optionally substituted $C_{3-6}$cycloalkyl, $C_{2-4}$alkylNR$^a$R$^b$, or $C_{1-4}$alkylCOR$^d$, wherein all such optional substitutions are made with 0, 1, 2 or 3 R$^e$;

$R^a$ and $R^b$ are, at each occurrence independently selected from H, $C_{1-4}$alkyl or $C_{5-6}$cycloalkyl, or $R^a$ and $R^b$ and the N to which they are attached in combination form a 5 or 6-membered N-linked heterocycle having 2 nitrogen or, 1 nitrogen and 1 oxygen, ring atoms, wherein the non-linked nitrogen is substituted with R$^c$;

$R^c$ is, at each occurrence independently selected from H, $C_{1-3}$alkyl, or substituted phenyl with 0, 1, 2, or 3 R$^e$;

$R^d$ is, at each occurrence independently selected from $C_{1-3}$alkyl, $C_{1-3}$alkoxy, or NR$^a$R$^b$;

$R^e$ is, at each occurrence independently selected from OH, F, Cl, Br, I, CN, $NO_2$, $CF_3$, $C_{1-6}$alkyl, or $C_{1-6}$alkoxy;

$R^2$, $R^3$, 10 and $R^7$ are independently selected from H, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, optionally substituted $C_{1-3}$alkylaryl, optionally substituted $C_{1-3}$alkylheterocycle, optionally substituted $C_{1-6}$alkyl, or optionally substituted $C_{3-6}$ cycloalkyl, wherein all such optional substitutions are made with 0, 1, 2, or 3 R$^e$ moieties, with the requirement that one or more of $R^2$, $R^3$, $R^6$ and $R^7$ are aromatic or heteroaromatic;

$R^4$ is H, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, $C_{1-6}$alkyl, $C_{3-6}$ cycloalkyl, or CR$^9$R$^{10}$R$^{11}$;

$R^5$ is $C_{1-6}$alkylR$^{12}$ or CH(OH)R$^{13}$;

$R^9$, $R^{10}$ and $R^{11}$ are, at each occurrence independently selected from H, F, $C_{1-4}$alkyl, OH, $OCH_3$, SH, $SCH_3$, $CH_2SCH_3$;

$R^{12}$ is phenyl substituted with 0, 1, 2 or 3 R$^e$;

$R^{13}$ is $C_{1-6}$alkyl or R$^{12}$;

or a pharmaceutically acceptable salt thereof.

In a particular embodiment the present invention provides a compound having formula (II) wherein:

$R^1$ is selected from H, or optionally substituted alkyl wherein such optional substitution is made with 0, 1, or 2 substituents selected from $C_{1-6}$cycloalkyl, $C_{1-6}$cycloalkoxy, or phenyl;

$R^2$, $R^3$, $R^6$ and $R^7$ are independently selected from H, or optionally substituted 6-membered aromatic, wherein such optional substitution is made with 0, 1, 2, or 3 $R^e$ moieties, with the requirement that one or more of $R^2$, $R^3$, $R^6$ and $R^7$ are aromatic;

$R^4$ is H, or $C_{1-6}$alkyl;

$R^5$ is $C_{1-3}$alkyl$R^{12}$ or $C_{1-6}$alkyl;

$R^{12}$ is phenyl substituted with 0, 1, 2 or 3 $R^e$;

$R^e$ is, at each occurrence independently selected from OH, F, Cl, Br, I, CN, $NO_2$, $CF_3$, $C_{1-6}$alkyl, or $C_{1-6}$alkoxy;

or a pharmaceutically acceptable salt thereof.

In a particular embodiment the present invention provides a compound having formula (II) wherein:

$R^1$ is selected from H, —$C_{1-6}$alkyl, —$(CH_2)_2OCH_3$, —$CH_2$-phenyl, —$CH_2C_{1-6}$cycloalkyl;

$R^2$, $R^3$, $R^6$ and $R^7$ are independently selected from H, or a substituted phenyl, wherein such substitutent is selected from 1, 2, or 3 of the following F, Cl, Br, I or $OCH_3$;

$R^4$ is H, or $C_{1-6}$alkyl;

$R^5$ is —$C_{1-6}$alkyl, —$C_{1-3}$alkyl$R^{12}$ wherein $R^{12}$ is a substituted phenyl, wherein such substitutent is selected from 1, 2 or 3 of the following F, Cl, Br, I or $OCH_3$;

or a pharmaceutically acceptable salt thereof.

In a particular embodiment the present invention provides a compound having formula (II) wherein:

$R^1$ is selected from —$C_{1-3}$alkyl, or —$CH_2C_{1-4}$cycloalkyl.

In a particular embodiment the present invention provides a compound having formula (II) wherein:

$R^1$ is selected from methyl or —$CH_2$cyclopropane.

In a particular embodiment the present invention provides a compound having formula (II) wherein:

$R^e$ is at each occurrence independently selected from F, Cl, $CF_3$, $C_{1-6}$alkyl, or $C_{1-6}$alkoxy.

In a particular embodiment the present invention provides a compound having formula (II) wherein:

$R^2$ is an optionally substituted phenyl, wherein such optional substitution is made with 0, 1, 2, or 3 $R^e$ moieties.

In a particular embodiment the present invention provides a compound having formula (II) wherein:

$R^3$, $R^6$ and $R^7$ are H.

In a particular embodiment the present invention provides a compound having formula (II) wherein:

$R^4$ is $C_{1-6}$alkyl.

In a particular embodiment the present invention provides a compound having formula (II) wherein:

$R^5$ is —$C_{1-6}$alkyl, —$C_{1-3}$alkyl$R^{12}$ wherein $R^{12}$ is a substituted phenyl, wherein such substitutent is selected from 1, 2 or 3 of the following F, Cl, Br, I or $OCH_3$.

In a particular embodiment the present invention provides a compound having formula (II) selected from:

$N^2$-[(3,5-difluorophenyl)acetyl]-1-[(3S,7S)-1-methyl-2-oxo-7-phenyl-2,3,6,7-tetrahydro-1H-azepin-3-yl]-L-alaninamide;

$N^2$-[(3,5-difluorophenyl)acetyl]-$N^1$-[(3S,7S)-2-oxo-7-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S,7S)-1-methyl-2-oxo-7-phenyl-2,3,6,7-tetrahydro-1H-azepin-3-yl]-L-alaninamide;

$N^2$-[(2R)-2-(3,5-difluorophenyl)-2-hydroxyacetyl]-$N^1$-[(3S,7S)-1-methyl-2-oxo-7-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S,7S)-2-oxo-7-phenyl-2,3,6,7-tetrahydro-1H-azepin-3-yl]-L-alaninamide;

$N^2$-[(2R)-2-(3,5-difluorophenyl)-2-hydroxyacetyl]-$N^1$-[(3S,7S)-2-oxo-7-phenyl-2,3,6,7-tetrahydro-1H-azepin-3-yl]-L-alaninamide;

$N^2$-[(3,5-difluorophenyl)acetyl]-$N^1$-[(3S,7R)-1-methyl-2-oxo-7-phenyl-2,3,6,7-tetrahydro-1H-azepin-3-yl]-L-alaninamide;

$N^2$-[(3,5-difluorophenyl)acetyl]-$N^1$-[(3S,7R)-2-oxo-7-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S,7R)-1-methyl-2-oxo-7-phenyl-2,3,6,7-tetrahydro-1H-azepin-3-yl]-L-alaninamide;

$N^2$-[(2R)-2-(3,5-difluorophenyl)-2-hydroxyacetyl]-$N^1$-[(3S,7R)-1-methyl-2-oxo-7-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S,7R)-2-oxo-7-phenyl-2,3,6,7-tetrahydro-1H-azepin-3-yl]-L-alaninamide;

$N^2$-[(2R)-2-(3,5-difluorophenyl)-2-hydroxyacetyl]-$N^1$-[(3S,7R)-2-oxo-7-phenyl-2,3,6,7-tetrahydro-1H-azepin-3-yl]-L-alaninamide;

$N^2$-[(3,5-difluorophenyl)acetyl]-$N^1$-[(3S,6R)-1-methyl-2-oxo-6-phenyl-2,3,6,7-tetrahydro-1H-azepin-3-yl]-L-alaninamide;

$N^2$-[(3,5-difluorophenyl)acetyl]-$N^1$-[(3S,6R)-2-oxo-6-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S,6R)-1-methyl-2-oxo-6-phenyl-2,3,6,7-tetrahydro-1H-azepin-3-yl]-L-alaninamide;

$N^2$-[(2R)-2-(3,5-difluorophenyl)-2-hydroxyacetyl]-$N^1$-[(3S,6R)-1-methyl-2-oxo-6-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S,6R)-2-oxo-6-phenyl-2,3,6,7-tetrahydro-1H-azepin-3-yl]-L-alaninamide;

$N^2$-[(2R)-2-(3,5-difluorophenyl)-2-hydroxyacetyl]-$N^1$-[(3S,6R)-2-oxo-6-phenyl-2,3,6,7-tetrahydro-1H-azepin-3-yl]-L-alaninamide;

$N^2$-[(3,5-difluorophenyl)acetyl]-$N^1$-[(3S,6S)-1-methyl-2-oxo-6-phenyl-2,3,6,7-tetrahydro-1H-azepin-3-yl]-L-alaninamide;

$N^2$-[(3,5-difluorophenyl)acetyl]-$N^1$-[(3S,6S)-2-oxo-6-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S,6S)-1-methyl-2-oxo-6-phenyl-2,3,6,7-tetrahydro-1H-azepin-3-yl]-L-alaninamide;

$N^2$-[(2R)-2-(3,5-difluorophenyl)-2-hydroxyacetyl]-$N^1$-[(3S,6S)-1-methyl-2-oxo-6-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S,6S)-2-oxo-7-phenyl-2,3,6,7-tetrahydro-1H-azepin-3-yl]-L-alaninamide;

$N^2$-[(2R)-2-(3,5-difluorophenyl)-2-hydroxyacetyl]-$N^1$-[(3S,6S)-2-oxo-6-phenyl-2,3,6,7-tetrahydro-1H-azepin-3-yl]-L-alaninamide;

$N^2$-[(3,5-difluorophenyl)acetyl]-$N^1$-[(3S)-1-methyl-2-oxo-5-phenyl-2,3,6,7-tetrahydro-1H-azepin-3-yl]-L-alaninamide;

$N^2$-[(3,5-difluorophenyl)acetyl]-$N^1$-[(3S)-2-oxo-5-phenyl-2,3,6,7-tetrahydro-1H-azepin-3-yl]-L-alaninamide;

$N^2$-[(2S)-2-(3,5-difluorophenyl)-2-hydroxyacetyl]-$N^1$-[(3S)-1-methyl-2-oxo-5-phenyl-2,3,6,7-tetrahydro-1H-azepin-3-yl]-L-alaninamide;

N²-[(2R)-2-(3,5-difluorophenyl)-2-hydroxyacetyl]-N¹-[(3S)-1-methyl-2-oxo-5-phenyl-2,3,6,7-tetrahydro-1H-azepin-3-yl]-L-alaninamide;
N²-[(2S)-2-(3,5-difluorophenyl)-2-hydroxyacetyl]-N¹-[(3S)-2-oxo-5-phenyl-2,3,6,7-tetrahydro-1H-azepin-3-yl]-L-alaninamide;
N²-[(2R)-2-(3,5-difluorophenyl)-2-hydroxyacetyl]-N¹-[(3S)-2-oxo-5-phenyl-2,3,6,7-tetrahydro-1H-azepin-3-yl]-L-alaninamide;
N²-[(3,5-difluorophenyl)acetyl]-N¹-[(3S)-1-methyl-2-oxo-4-phenyl-2,3,6,7-tetrahydro-1H-azepin-3-yl]-L-alaninamide;
N²-[(3,5-difluorophenyl)acetyl]-N¹-[(3S)-2-oxo-4-phenyl-2,3,6,7-tetrahydro-1H-azepin-3-yl]-L-alaninamide;
N²-[(2S)-2-(3,5-difluorophenyl)-2-hydroxyacetyl]-N¹-[(3S)-1-methyl-2-oxo-4-phenyl-2,3,6,7-tetrahydro-1H-azepin-3-yl]-L-alaninamide;
N²-[(2R)-2-(3,5-difluorophenyl)-2-hydroxyacetyl]-N¹-[(3S)-1-methyl-2-oxo-4-phenyl-2,3,6,7-tetrahydro-1H-azepin-3-yl]-L-alaninamide;
N²-[(2S)-2-(3,5-difluorophenyl)-2-hydroxyacetyl]-N¹-[(3S)-2-oxo-4-phenyl-2,3,6,7-tetrahydro-1H-azepin-3-yl]-L-alaninamide;
N²-[(2R)-2-(3,5-difluorophenyl)-2-hydroxyacetyl]-N¹-[(3S)-2-oxo-4-phenyl-2,3,6,7-tetrahydro-1H-azepin-3-yl]-L-alaninamide.

In a particular embodiment the present invention provides a compound having formula (III):

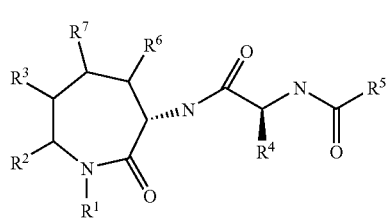

(III)

wherein:

$R^1$ is selected from H, optionally substituted $C_{1-3}$alkylaryl, optionally substituted $C_{1-3}$alkylheterocycle, optionally substituted alkyl, optionally substituted $C_{3-6}$cycloalkyl, $C_{2-4}$alkylNR$^a$R$^b$, or $C_{1-4}$alkylCOR$^d$, wherein all such optional substitutions are made with 0, 1, 2 or 3 R$^e$;

R$^a$ and R$^b$ are, at each occurrence independently selected from H, $C_{1-4}$alkyl or $C_{5-6}$cycloalkyl, or R$^a$ and R$^b$ and the N to which they are attached in combination form a 5 or 6-membered N-linked heterocycle having 2 nitrogen or, 1 nitrogen and 1 oxygen, ring atoms, wherein the non-linked nitrogen is substituted with R$^c$;

R$^c$ is, at each occurrence independently selected from H, $C_{1-3}$alkyl, or substituted phenyl with 0, 1, 2, or 3 R$^e$;

R$^d$ is, at each occurrence independently selected from $C_{1-3}$alkyl, $C_{1-3}$alkoxy, or NR$^a$R$^b$;

R$^e$ is, at each occurrence independently selected from OH, F, Cl, Br, I, CN, NO$_2$, CF$_3$, $C_{1-6}$alkyl, or $C_{1-6}$alkoxy;

$R^2$, $R^3$ and $R^7$ are independently selected from H, optionally substituted $C_{1-3}$alkylaryl, optionally substituted $C_{1-3}$alkylheterocycle, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, optionally substituted $C_{1-6}$alkyl, or optionally substituted $C_{3-6}$cycloalkyl, wherein all such optional substitutions are made with 0, 1, 2, or 3 R$^e$ moieties, with the requirement that one or more of $R^2$, $R^3$ and $R^7$ are aromatic or heteroaromatic;

$R^6$ is independently selected from H, optionally substituted $C_{1-3}$alkylaryl, optionally substituted $C_{1-3}$alkylheterocycle, optionally substituted $C_{1-6}$alkyl, or optionally substituted $C_{3-6}$cycloalkyl, wherein all such optional substitutions are made with 0, 1, 2, or 3 R$^e$ moieties;

$R^4$ is H, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, $C_{1-6}$alkyl, $C_{3-6}$cycloalkyl, or CR$^9$R$^{10}$R$^{11}$; a $R^5$ is —$C_{1-6}$alkyl, —$C_{1-3}$alkylR$^{12}$ or CH(OH)R$^{13}$;

$R^9$, $R^{10}$ and $R^{11}$ are, at each occurrence independently selected from H, F, $C_{1-4}$alkyl, OH, OCH$_3$, SH, SCH$_3$, CH$_2$SCH$_3$;

$R^{12}$ is phenyl substituted with 0, 1, 2 or 3 R$^e$;

$R^{13}$ is $C_{1-6}$alkyl or $R^{12}$;

or a pharmaceutically acceptable salt thereof.

In a particular embodiment the present invention provides a compound having formula (III) wherein:

$R^1$ is selected from H, or optionally substituted alkyl, wherein such optional substitution is made with 0, 1, or 2 substituents selected from $C_{1-6}$cycloalkyl, $C_{1-6}$cycloalkoxy, or phenyl;

$R^2$, $R^3$, $R^6$ and $R^7$ are independently selected from H, or optionally substituted 6-membered aromatic, wherein such optional substitution is made with 0, 1, 2, or 3 R$^e$ moieties, with the requirement that one or more of $R^2$, $R^3$, $R^6$ and $R^7$ are aromatic;

$R^4$ is H, or $C_{1-6}$alkyl;

$R^5$ is —$C_{1-6}$alkyl or —$C_{1-3}$alkylR$^{12}$;

$R^{12}$ is phenyl substituted with 0, 1, 2 or 3 R$^e$;

R$^e$ is, at each occurrence independently selected from OH, F, Cl, Br, I, CN, NO$_2$, CF$_3$, $C_{1-6}$alkyl, or $C_{1-6}$alkoxy;

or a pharmaceutically acceptable salt thereof.

In a particular embodiment the present invention provides a compound having formula (III) wherein:

$R^1$ is selected from H, —$C_{1-6}$alkyl, —(CH$_2$)$_2$OCH$_3$, —CH$_2$-phenyl, —CH$_2$C$_{1-6}$cycloalkyl;

$R^2$, $R^3$, $R^6$ and $R^7$ are independently selected from H, or a substituted phenyl, wherein such substitutent is selected from 1, 2, or 3 of the following F, Cl, Br, I or OCH$_3$;

$R^4$ is H, or $C_{1-6}$alkyl;

$R^5$ is —$C_{1-6}$alkyl, —$C_{1-3}$alkylR$^{12}$ wherein $R^{12}$ is a substituted phenyl, wherein such substitutent is selected from 1, 2 or 3 of the following F, Cl, Br, I or OCH$_3$;

or a pharmaceutically acceptable salt thereof.

In a particular embodiment the present invention provides a compound having formula (III) wherein:

$R^1$ is —$C_{1-6}$alkyl, —CH$_2$C$_{1-4}$cycloalkyl.

In a particular embodiment the present invention provides a compound having formula (III) wherein:

$R^1$ is methyl or —CH$_2$cyclopropane.

In a particular embodiment the present invention provides a compound having formula (III) wherein:

R$^e$ is, at each occurrence independently selected from F, Cl, CF$_3$, $C_{1-6}$alkyl, or $C_{1-6}$alkoxy.

In a particular embodiment the present invention provides a compound having formula (III) wherein:

$R^2$ is an optionally substituted phenyl, wherein such optional substitution is made with 0, 1, 2, or 3 R$^e$ moieties.

In a particular embodiment the present invention provides a compound having formula (III) wherein:

$R^3$, $R^6$ and $R^7$ are H.

In a particular embodiment the present invention provides a compound having formula (III) wherein:
R⁴ is $C_{1-6}$alkyl.

In a particular embodiment the present invention provides a compound having formula (III) wherein:

In a particular embodiment the present invention provides a compound having formula (III) wherein:
R⁵ is —$C_{1-6}$alkyl, —$C_{1-3}$alkylR¹² wherein R¹² is a substituted phenyl, wherein such substituent is selected from 1, 2 or 3 of the following F, Cl, Br, I or $OCH_3$.

In a particular embodiment the present invention provides a compound having formula (III) selected from:

N²-[(3,5-difluorophenyl)acetyl]-N¹-[(3S,7S)-1-methyl-2-oxo-7-phenylazepan-3-yl]-L-alaninamide;

N²-[(3,5-difluorophenyl)acetyl]-N¹-[(3S,7R)-1-methyl-2-oxo-7-phenylazepan-3-yl]alaninamide;

N²-[(3,5-difluorophenyl)acetyl]-N¹-[(3R,7S)-1-methyl-2-oxo-7-phenylazepan-3-yl]-L-alaninamide;

N²-[(3,5-difluorophenyl)acetyl]-N¹-[(3R,7R)-1-methyl-2-oxo-7-phenylazepan-3-yl]-L-alaninamide (3□);

N²-[(3,5-difluorophenyl)acetyl]-N¹-[(3S,7R)-2-oxo-7-phenylazepan-3-yl]-L-alaninamide;

N²-[(2S)-2-(3,5-difluorophenyl)-2-hydroxyacetyl]-N¹-[(3S,7R)-1-methyl-2-oxo-7-phenylazepan-3-yl]-L-alaninamide;

N²-[(2R)-2-(3,5-difluorophenyl)-2-hydroxyacetyl]-N¹-[(3S,7R)-1-methyl-2-oxo-phenylazepan-3-yl]-L-alaninamide;

N²-[(2S)-2-(3,5-difluorophenyl)-2-hydroxyacetyl]-N¹-[(3S,7R)-2-oxo-7-phenylazepan-3-yl]-L-alaninamide;

N²-[(2R)-2-(3,5-difluorophenyl)-2-hydroxyacetyl]-N¹-[(3S,7R)-2-oxo-7-phenylazepan-3-yl]-L-alaninamide;

N²-[(3,5-difluorophenyl)acetyl]-N¹-[(3S,7S)-2-oxo-7-phenylazepan-3-yl]-L-alaninamide;

N²-[(2S)-2-(3,5-difluorophenyl)-2-hydroxyacetyl]-N¹-[(3S,7S)-1-methyl-2-oxo-7-phenylazepan-3-yl]-L-alaninamide;

N²-[(2R)-2-(3,5-difluorophenyl)-2-hydroxyacetyl]-N¹-[(3S,7S)-1-methyl-2-oxo-phenylazepan-3-yl]-L-alaninamide;

N²-[(2S)-2-(3,5-difluorophenyl)-2-hydroxyacetyl]-N¹-[(3S,7S)-2-oxo-7-phenylazepan-3-yl]-L-alaninamide;

N²-[(2R)-2-(3,5-difluorophenyl)-2-hydroxyacetyl]-N¹-[(3S,7S)-2-oxo-7-phenylazepan-3-yl]-L-alaninamide;

N²-[(3,5-difluorophenyl)acetyl]-N¹-[(3S,6R)-1-methyl-2-oxo-6-phenylazepan-3-yl]-L-alaninamide;

N²-[(3,5-difluorophenyl)acetyl]-N¹-[(3S,6R)-2-oxo-6-phenylazepan-3-yl]-L-alaninamide;

N²-[(2S)-2-(3,5-difluorophenyl)-2-hydroxyacetyl]-N¹-[(3S,6R)-1-methyl-2-oxo-6-phenylazepan-3-yl]-L-alaninamide;

N²-[(2R)-2-(3,5-difluorophenyl)-2-hydroxyacetyl]-N¹-[(3S,6R)-1-methyl-2-oxo-6-phenylazepan-3-yl]-L-alaninamide;

N²-[(2S)-2-(3,5-difluorophenyl)-2-hydroxyacetyl]-N¹-[(3S,6R)-2-oxo-6-phenylazepan-3-yl]-L-alaninamide;

N²-[(2R)-2-(3,5-difluorophenyl)-2-hydroxyacetyl]-N¹-[(3S,6R)-1-methyl-2-oxo-6-phenylazepan-3-yl]-L-alaninamide;

N²-[(3,5-difluorophenyl)acetyl]-N¹-[(3S,6S)-1-methyl-2-oxo-6-phenylazepan-3-yl]-L-alaninamide;

N²-[(3,5-difluorophenyl)acetyl]-N¹-[(3S,6S)-2-oxo-6-phenylazepan-3-yl]-L-alaninamide;

N²-[(2S)-2-(3,5-difluorophenyl)-2-hydroxyacetyl]-N¹-[(3S,6S)-1-methyl-2-oxo-6-phenylazepan-3-yl]-L-alaninamide;

N¹-[(2R)-2-(3,5-difluorophenyl)-2-hydroxyacetyl]-N¹-[(3S,6S)-1-methyl-2-oxo-6-phenylazepan-3-yl]-L-alaninamide;

N²-[(2S)-2-(3,5-difluorophenyl)-2-hydroxyacetyl]-N¹-[(3S,6S)-2-oxo-6-phenylazepan-3-yl]-L-alaninamide;

N²-[(2R)-2-(3,5-difluorophenyl)-2-hydroxyacetyl]-N¹-[(3S,6S)-2-oxo-6-phenylazepan-3-yl]-L-alaninamide;

N²-[(3,5-difluorophenyl)acetyl]-N¹-[(3S,4R)-1-methyl-2-oxo-4-phenylazepan-3-yl]-L-alaninamide;

N²-[(3,5-difluorophenyl)acetyl]-N¹-[(3S,4R)-2-oxo-4-phenylazepan-3-yl]-L-alaninamide;

N²-[(2S)-2-(3,5-difluorophenyl)-2-hydroxyacetyl]-N¹-[(3S,4R)-1-methyl-2-oxo-4-phenylazepan-3-yl]-L-alaninamide;

N²-[(2R)-2-(3,5-difluorophenyl)-2-hydroxyacetyl]-N¹-[(3S,4R)-1-methyl-2-oxo-4-phenylazepan-3-yl]-L-alaninamide;

N²-[(2S)-2-(3,5-difluorophenyl)-2-hydroxyacetyl]-N¹-[(3S,4R)-2-oxo-4-phenylazepan-3-yl]-L-alaninamide;

N²-[(2R)-2-(3,5-difluorophenyl)-2-hydroxyacetyl]-N¹-[(3S,4R)-2-oxo-4-phenylazepan-3-yl]-L-alaninamide;

N²-[(3,5-difluorophenyl)acetyl]-N¹-[(3S,4S)-1-methyl-2-oxo-4-phenylazepan-3-yl]-L-alaninamide;

N²-[(3,5-difluorophenyl)acetyl]-N¹-[(3S,4S)-2-oxo-4-phenylazepan-3-yl]-L-alaninamide;

N²-[(2S)-2-(3,5-difluorophenyl)-2-hydroxyacetyl]-N¹-[(3S,4S)-1-methyl-2-oxo-4-phenylazepan-3-yl]-L-alaninamide;

N²-[(2R)-2-(3,5-difluorophenyl)-2-hydroxyacetyl]-N¹-[(3S,4S)-1-methyl-2-oxo-4-phenylazepan-3-yl]-L-alaninamide;

N²-[(2S)-2-(3,5-difluorophenyl)-2-hydroxyacetyl]-N¹-[(3S,4S)-2-oxo-4-phenylazepan-3-yl]-L-alaninamide;

N²-[(2R)-2-(3,5-difluorophenyl)-2-hydroxyacetyl]-N¹-[(3S,4S)-2-oxo-4-phenylazepan-3-yl]-L-alaninamide;

N²-[(3,5-difluorophenyl)acetyl]-N¹-[(3S,4R,7S)-1-methyl-2-oxo-4,7-diphenylazepan-3-yl]-L-alaninamide;

N²-[(3,5-difluorophenyl)acetyl]-N¹-[(3S,4R,7S)-2-oxo-4,7-diphenylazepan-3-yl]-L-alaninamide;

N²-[(2S)-2-(3,5-difluorophenyl)-2-hydroxyacetyl]-N¹-[(3S,4R,7S)-1-methyl-2-oxo-4,7-diphenylazepan-3-yl]-L-alaninamide;

N²-[(2R)-2-(3,5-difluorophenyl)-2-hydroxyacetyl]-N¹-[(3S,4R,7S)-1-methyl-2-oxo-4,7-diphenylazepan-3-yl]-L-alaninamide;

N²-[(2S)-2-(3,5-difluorophenyl)-2-hydroxyacetyl]-N¹-[(3S,4R,7S)-2-oxo-4,7-diphenylazepan-3-yl]-L-alaninamide;

N²-[(2R)-2-(3,5-difluorophenyl)-2-hydroxyacetyl]-N¹-[(3S,4R,7S)-2-oxo-4,7-diphenylazepan-3-yl]-L-alaninamide;

N²-[(3,5-difluorophenyl)acetyl]-N¹-[(3S,4S,7S)-1-methyl-2-oxo-4,7-diphenylazepan-3-yl]-L-alaninamide;

N²-[(3,5-difluorophenyl)acetyl]-N¹-[(3S,4S,7S)-2-oxo-4,7-diphenylazepan-3-yl]-L-alaninamide;

N²-[(2S)-2-(3,5-difluorophenyl)-2-hydroxyacetyl]-N¹-[(3S,4S,7S)-1-methyl-2-oxo-4,7-diphenylazepan-3-yl]-L-alaninamide;

N²-[(2R)-2-(3,5-difluorophenyl)-2-hydroxyacetyl]-N¹-[(3S,4S,7S)-1-methyl-2-oxo-4,7-diphenylazepan-3-yl]-L-alaninamide;

N²-[(2S)-2-(3,5-difluorophenyl)-2-hydroxyacetyl]-N¹-[(3S,4S,7S)-2-oxo-4,7-diphenylazepan-3-yl]-L-alaninamide;

N²-[(2R)-2-(3,5-difluorophenyl)-2-hydroxyacetyl]-N¹-[(3S,4S,7S)-2-oxo-4,7-diphenylazepan-3-yl]-L-alaninamide;

N²-[(3,5-difluorophenyl)acetyl]-N¹-[(3S,4R,7R)-1-methyl-2-oxo-4,7-diphenylazepan-3-yl]-L-alaninamide;

N²-[(3,5-difluorophenyl)acetyl]-N¹-[(3S,4R,7R)-2-oxo-4,7-diphenylazepan-3-yl]-L-alaninamide;

N²-[(2S)-2-(3,5-difluorophenyl)-2-hydroxyacetyl]-N¹-[(3S,4R,7R)-1-methyl-2-oxo-4,7-diphenylazepan-3-yl]-L-alaninamide;

N²-[(2R)-2-(3,5-difluorophenyl)-2-hydroxyacetyl]-N¹-[(3S,4R,7R)-1-methyl-2-oxo-4,7-diphenylazepan-3-yl]-L-alaninamide;
N²-[(2S)-2-(3,5-difluorophenyl)-2-hydroxyacetyl]-N¹-[(3S,4R,7R)-2-oxo-4,7-diphenylazepan-3-yl]-L-alaninamide;
N²-[(2R)-2-(3,5-difluorophenyl)-2-hydroxyacetyl]-N¹-[(3S,4R,7R)-2-oxo-4,7-diphenylazepan-3-yl]-L-alaninamide;
N²-[(3,5-difluorophenyl)acetyl]-N¹-[(3S,4R,6S)-1-methyl-2-oxo-4,6-diphenylazepan-3-yl]-L-alaninamide;
N²-[(3,5-difluorophenyl)acetyl]-N¹-[(3S,4R,6S)-2-oxo-4,6-diphenylazepan-3-yl]-L-alaninamide;
N²-[(2S)-2-(3,5-difluorophenyl)-2-hydroxyacetyl]-N¹-[(3S,4R,6S)-1-methyl-2-oxo-4,6-diphenylazepan-3-yl]-L-alaninamide;
N²-[(2R)-2-(3,5-difluorophenyl)-2-hydroxyacetyl]-N¹-[(3S,4R,6S)-1-methyl-2-oxo-4,6-diphenylazepan-3-yl]-L-alaninamide;
N²-[(2S)-2-(3,5-difluorophenyl)-2-hydroxyacetyl]-N¹-[(3S,4R,6S)-2-oxo-4,6-diphenylazepan-3-yl]-L-alaninamide;
N²-[(2R)-2-(3,5-difluorophenyl)-2-hydroxyacetyl]-N¹-[(3S,4R,6S)-2-oxo-4,6-diphenylazepan-3-yl]-L-alaninamide;
N²-[(3,5-difluorophenyl)acetyl]-N¹-[(3S,4S,6S)-1-methyl-2-oxo-4,6-diphenylazepan-3-yl]-L-alaninamide;
N²-[(3,5-difluorophenyl)acetyl]-N¹-[(3S,4S,6S)-2-oxo-4,6-diphenylazepan-3-yl]-L-alaninamide;
N²-[(2S)-2-(3,5-difluorophenyl)-2-hydroxyacetyl]-N¹-[(3S,4S,6S)-1-methyl-2-oxo-4,6-diphenylazepan-3-yl]-L-alaninamide;
N²-[(2R)-2-(3,5-difluorophenyl)-2-hydroxyacetyl]-N¹-[(3S,4S,6S)-1-methyl-2-oxo-4,6-diphenylazepan-3-yl]-L-alaninamide;
N²-[(2S)-2-(3,5-difluorophenyl)-2-hydroxyacetyl]-N¹-[(3S,4S,6S)-2-oxo-4,6-diphenylazepan-3-yl]-L-alaninamide;
N²-[(2R)-2-(3,5-difluorophenyl)-2-hydroxyacetyl]-N¹-[(3S,4S,6S)-2-oxo-4,6-diphenylazepan-3-yl]-L-alaninamide;
N²-[(3,5-difluorophenyl)acetyl]-N¹-[(3S,4R,6R)-1-methyl-2-oxo-4,6-diphenylazepan-3-yl]-L-alaninamide;
N²-[(3,5-difluorophenyl)acetyl]-N¹-[(3S,4R,6R)-2-oxo-4,6-diphenylazepan-3-yl]-L-alaninamide;
N²-[(2S)-2-(3,5-difluorophenyl)-2-hydroxyacetyl]-N¹-[(3S,4R,6R)-1-methyl-2-oxo-4,6-diphenylazepan-3-yl]-L-alaninamide;
N²-[(2R)-2-(3,5-difluorophenyl)-2-hydroxyacetyl]-N¹-[(3S,4R,6R)-1-methyl-2-oxo-4,6-diphenylazepan-3-yl]-L-alaninamide;
N²-[(2S)-2-(3,5-difluorophenyl)-2-hydroxyacetyl]-N¹-[(3S,4R,6R)-2-oxo-4,6-diphenylazepan-3-yl]-L-alaninamide;
N²-[(2R)-2-(3,5-difluorophenyl)-2-hydroxyacetyl]-N¹-[(3S,4R,6R)-2-oxo-4,6-diphenylazepan-3-yl]-L-alaninamide;
N²-[(3,5-difluorophenyl)acetyl]-N¹-[(3S,5R,7S)-1-methyl-2-oxo-5,7-diphenylazepan-3-yl]-L-alaninamide;
N²-[(3,5-difluorophenyl)acetyl]-N¹-[(3S,5R,7S)-2-oxo-5,7-diphenylazepan-3-yl]-L-alaninamide;
N²-[(2S)-2-(3,5-difluorophenyl)-2-hydroxyacetyl]-N¹-[(3S,5R,7S)-1-methyl-2-oxo-5,7-diphenylazepan-3-yl]-L-alaninamide;
N²-[(2R)-2-(3,5-difluorophenyl)-2-hydroxyacetyl]-N¹-[(3S,5R,7S)-1-methyl-2-oxo-5,7-diphenylazepan-3-yl]-L-alaninamide;
N²-[(2S)-2-(3,5-difluorophenyl)-2-hydroxyacetyl]-N¹-[(3S,5R,7S)-2-oxo-5,7-diphenylazepan-3-yl]-L-alaninamide;
N²-[(2R)-2-(3,5-difluorophenyl)-2-hydroxyacetyl]-N¹-[(3S,5R,7S)-2-oxo-5,7-diphenylazepan-3-yl]-L-alaninamide;
N²-[(3,5-difluorophenyl)acetyl]-N¹-[(3S,5S,7S)-1-methyl-2-oxo-5,7-diphenylazepan-3-yl]-L-alaninamide;
N²-[(3,5-difluorophenyl)acetyl]-N¹-[(3S,5S,7S)-2-oxo-5,7-diphenylazepan-3-yl]-L-alaninamide;
N²-[(2S)-2-(3,5-difluorophenyl)-2-hydroxyacetyl]-N¹-[(3S,5S,7S)-1-methyl-2-oxo-5,7-diphenylazepan-3-yl]-L-alaninamide;
N²-[(2R)-2-(3,5-difluorophenyl)-2-hydroxyacetyl]-N¹-[(3S,5S,7S)-1-methyl-2-5,7-diphenylazepan-3-yl]-L-alaninamide;
N²-[(2S)-2-(3,5-difluorophenyl)-2-hydroxyacetyl]-N¹-[(3S,5S,7S)-2-oxo-5,7-diphenylazepan-3-yl]-L-alaninamide;
N²-[(2R)-2-(3,5-difluorophenyl)-2-hydroxyacetyl]-N¹-[(3S,5S,7S)-2-oxo-5,7-diphenylazepan-3-yl]-L-alaninamide;
N²-[(3,5-difluorophenyl)acetyl]-N¹-[(3S,5R,7R)-1-methyl-2-oxo-5,7-diphenylazepan-3-yl]-L-alaninamide;
N²-[(3,5-difluorophenyl)acetyl]-N¹-[(3S,5R,7R)-2-oxo-5,7-diphenylazepan-3-yl]-L-alaninamide;
N²-[(2S)-2-(3,5-difluorophenyl)-2-hydroxyacetyl]-N¹-[(3S,5R,7R)-1-methyl-2-oxo-5,7-diphenylazepan-3-yl]-L-alaninamide;
N²-[(2R)-2-(3,5-difluorophenyl)-2-hydroxyacetyl]-N¹-[(3S,5R,7R)-1-methyl-2-oxo-5,7-diphenylazepan-3-yl]-L-alaninamide;
N²-[(2S)-2-(3,5-difluorophenyl)-2-hydroxyacetyl]-N¹-[(3S,5R,7R)-2-oxo-5,7-diphenylazepan-3-yl]-L-alaninamide;
N²-[(2R)-2-(3,5-difluorophenyl)-2-hydroxyacetyl]-N¹-[(3S,5R,7R)-2-oxo-5,7-diphenylazepan-3-yl]-L-alaninamide;
N²-[(3,5-difluorophenyl)acetyl]-N¹-[(3S,5S)-1-methyl-2-oxo-5-phenylazepan-3-yl]-L-alaninamide;
N²-[(3,5-difluorophenyl)acetyl]-N¹-[(3S,5S)-2-oxo-5-phenylazepan-3-yl]-L-alaninamide;
N²-[(2S)-2-(3,5-difluorophenyl)-2-hydroxyacetyl]-N¹-[(3S,5S)-1-methyl-2-oxo-5-phenylazepan-3-yl]-L-alaninamide;
N²-[(2R)-2-(3,5-difluorophenyl)-2-hydroxyacetyl]-N¹-[(3S,5S)-1-methyl-2-oxo-5-phenylazepan-3-yl]-L-alaninamide;
N²-[(2S)-2-(3,5-difluorophenyl)-2-hydroxyacetyl]-N¹-[(3S,5S)-2-oxo-5-phenylazepan-3-yl]-L-alaninamide;
N²-[(2R)-2-(3,5-difluorophenyl)-2-hydroxyacetyl]-N¹-[(3S,5S)-2-oxo-5-phenylazepan-3-yl]-L-alaninamide;
N²-[(3,5-difluorophenyl)acetyl]-N¹-[(3S,5R)-1-methyl-2-oxo-5-phenylazepan-3-yl]-L-alaninamide;
N²-[(3,5-difluorophenyl)acetyl]-N¹-[(3S,5R)-2-oxo-5-phenylazepan-3-yl]-L-alaninamide;
N²-[(2S)-2-(3,5-difluorophenyl)-2-hydroxyacetyl]-N¹-[(3S,5R)-1-methyl-2-oxo-5-phenylazepan-3-yl]-L-alaninamide;
N²-[(2R)-2-(3,5-difluorophenyl)-2-hydroxyacetyl]-N¹-[(3S,5R)-1-methyl-2-oxo-5-phenylazepan-3-yl]-L-alaninamide;
N²-[(2S)-2-(3,5-difluorophenyl)-2-hydroxyacetyl]-N¹-[(3S,5R)-2-oxo-5-phenylazepan-3-yl]-L-alaninamide;
N²-[(2R)-2-(3,5-difluorophenyl)-2-hydroxyacetyl]-N¹-[(3S,5R)-2-oxo-5-phenylazepan-3-yl]-L-alaninamide.

In a particular embodiment the present invention provides a compound according to any one of claims 1 to 33 for use as a medicament.

In a particular embodiment the present invention provides a compound according to any one of claims 1 to 33 for use in the treatment of neurological disorders.

In a particular embodiment the present invention provides a compound according to any one of claims 1 to 33 for use in the prevention of Alzheimer's disease, or Down's Syndrome.

In a particular embodiment the present invention provides a compound according to any one of claims 1 to 33 for use in the treatment of Alzheimer's disease, or Down's Syndrome.

In a particular embodiment the present invention provides a compound according to any one of claims 1 to 33 for the treatment or prophylaxis of disorders associated with β-amyloid production.

In a particular embodiment the present invention provides a method of treatment of a human or animal suffering from neurological disorders associated with β-amyloid production comprising administering to a host in need of such treatment a therapeutically effective amount of a compound as defined in any one of claims 1 to 33.

In a particular embodiment the present invention provides a method of treating Alzheimer's disease in a patient comprising administering to a patient in need of such treatment an effective amount of a compound as defined in any one of claims 1 to 33.

In a particular embodiment the present invention provides a method of treating dementia in a patient comprising administering to a patient in need of such treatment and effective amount of a compound as defined in any one of claims 1 to 33.

In a particular embodiment the present invention provides a method of treating age associated cognitive decline, mild cognitive impairment, learning deficit, cognition deficit, attention deficit, memory loss, Attention Deficit Hyperactivity Disorder or Down's Syndrome in a patient comprising administering to a patient in need of such treatment and effective amount of a compound as defined in any one of claims 1 to 33.

In a particular embodiment the present invention provides a method of preventing Alzheimer's disease a patient comprising administering to a patient at risk of developing Alzheimer's disease an effective amount of a compound as defined in any one of claims 1 to 33.

In a particular embodiment the present invention provides a method of preventing dementia in a patient comprising administering to a patient at risk of developing dementia an effective amount of a compound as defined in any one of claims 1 to 33.

In a particular embodiment the present invention provides a method of preventing age associated cognitive decline, mild cognitive impairment, learning deficit, cognition deficit, attention deficit, memory loss, Attention Deficit Hyperactivity Disorder or Down's Syndrome in a patient comprising administering to a patient at risk of developing a learning deficit, cognition deficit, attention deficit, memory loss, Attention Deficit Hyperactivity Disorder or Down's Syndrome an effective amount of a compound as defined in any one of claims 1 to 33.

In a particular embodiment the present invention provides a method for inhibiting γ-secretase activity comprising administering to a host in need of such inhibition a therapeutically effective amount of a compound as defined in any one of claims 1 to 33.

In a particular embodiment the present invention provides a pharmaceutical composition comprising a compound as defined in any one of claims 1 to 33 or a pharmaceutically acceptable salt or in vivo hydrolysable ester thereof, together with at least one phamraceutically acceptable carrier, diluent or excipient.

In a particular embodiment the present invention provides a process for preparing a compound of formula (I) as claimed in claim 1 or a pharmaceutically acceptable salt or an in vivo hydrolysable ester therof which process comprises:

In a particular embodiment the present invention provides a process for the preparation of a compound of formula (1f) or a pharmaceutically acceptable salt or an in vivo hydrolysable ester therof which process comprises reacting a compound of formula 1d with TFA.

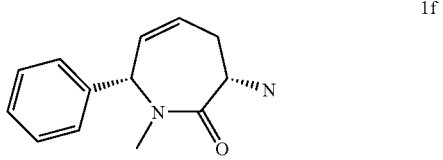

1f

In a particular embodiment the present invention provides a process for the preparation of a compound of formula 1 comprising reacting a compound of formula 1f and N-[(3, 5-difluorophenyl)acetyl]-L-alanine with HOBt-hydrate, EDAC.HCL and N-methyl morpholine.

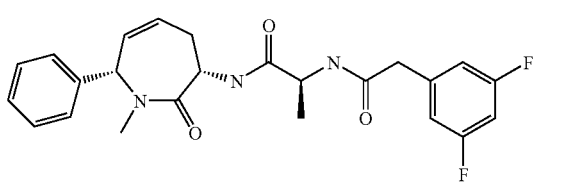

1

In a particular embodiment the present invention provides a process for the preparation of a compound of formula 2e comprising reacting a compound of formula 2c with H$_2$, Pearlman's Catalyst in ETOH.

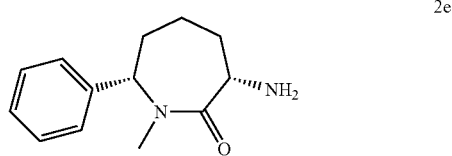

2e

In a particular embodiment the present invention provides a process for the preparation of a compound of formula 2 comprising reacting a compound of formula 2e and N-[(3, 5-difluorophenyl)acetyl]-L-alanine with HOBt-hydrate, EDAC.HCL and N-methyl morpholine.

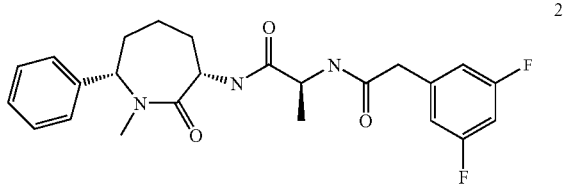

2

In a particular embodiment the present invention provides a process for the preparation of compound of formula 11f comprising reacting a compound of formula 11d with H2NNH2 in MeOH.

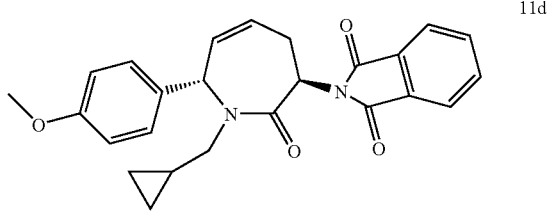

11d

In a particular embodiment the present invention provides a process for the preparation of a compound of formula 11A comprising reacting a compound of formula 11f and N-[(3, 5-difluorophenyl)acetyl]-L-alanine with with HOBt-hydrate, EDAC.HCL and N-methyl morpholine.

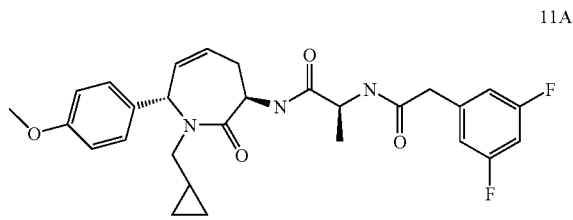

11A

Definitions

The definitions set forth in this section are intended to clarify terms used throughout this application. The term "herein" means the entire application.

As used in this application, the term "optionally substituted," as used herein, means that substitution is optional and therefore it is possible for the designated atom to be unsubstituted. In the event a substitution is desired then such substitution means that any number of hydrogens on the designated atom is replaced with a selection from the indicated group, provided that the normal valency of the designated atom is not exceeded, and that the substitution results in a stable compound. For example when a substituent is keto (i.e., =O), then 2 hydrogens on the atom are replaced. Other such examples include: halogen, hydroxy, nitro, cyano, trifluoromethyl, $C_{1-6}$alkyl, $C_{1-6}$alkoxy, alkenyl, alkynyl, $C_{3-6}$cycloalkyl, —OCOalkyl, amino, NHCHO, N-(alkyl)-CHO, NH—CO-amino, N-(alkyl)-CO-amino, NH—COalkyl, N-(alkyl)-COalkyl, carboxy, amidino, CO-amino, CO-alkyl, $CO_2$alkyl, mercapto, alkylthio, SO(alkyl), $SO_2$(alkyl), $SO_2$-amino, alkylsulfonylamino, aryl, and heterocyclic.

When any variable (e.g., $R^1$, $R^7$, $R^a$, $R^e$ etc.) occurs more than one time in any constituent or formula for a compound, its definition at each occurrence is independent of its definition at every other occurrence. Thus, for example, if a group is shown to be substituted with 0-3 $R^1$, then said group may optionally be substituted with 0, 1, 2 or 3 $R^1$ groups and $R^e$ at each occurrence is selected independently from the definition of $R^e$. Also, combinations of substituents and/or variables are permissible only if such combinations result in stable compounds.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein "acyl" refers to radicals of the of the general formula —C(=O)—R, wherein R is hydrogen, hydrocarbyl radical, amino or alkoxy. Acyl groups include, for example, acetyl, propionyl, benzoyl, phenyl acetyl, carboethoxy, and dimethylcarbamoyl.

As used herein "aromatic" refers to hydrocarbyl radicals having one or more polyunsaturated carbon rings having aromatic character, (e.g., 4n+2 delocalized electrons) and comprising up to about 14 carbon atoms.

As used herein, "alkyl" or "alkylene" is intended to include both branched and straight-chain saturated aliphatic hydrocarbon groups having the specified number of carbon atoms. For example, "$C_{1-6}$ alkyl" denotes alkyl having 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. As used herein, "$C_{1-3}$ alkyl", whether a terminal substituent or an alkylene group linking two substituents, is understood to specifically include both branched and straight-chain methyl, ethyl, and propyl.

As used herein, "alkenyl" or "alkenylene" is intended to include hydrocarbon chains of either a straight or branched configuration with one or more unsaturated carbon-carbon bonds that may occur at any stable point along the chain. Examples of "$C_{3-6}$alkenyl" include, but are not limited to, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration with one or more carbon-carbon triple bonds that may occur at any stable point along the chain, such as ethynyl, 1-propynyl, 2-propynyl, 1-butynyl, 2-butynyl, 3-butynyl, and the like.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" represent an alkyl group as defined above with the indicated number of carbon atoms attached through a sulphur bridge.

As used herein, the term "aryl" is intended to mean aromatic radicals including both monocyclic aromatic radicals comprising 6 carbon atoms and polycyclic aromatic radicals comprising up to about 14 carbon atoms.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, bicyclooctane, bicyclononane, bicyclodecane (decalin), bicyclooctane, fluorenyl, phenyl, naphthyl, indanyl, adamantyl, or tetrahydronaphthyl (tetralin).

As used herein "cycloalkyl" is intended to include saturated ring groups, having the specified number of carbon atoms. For example, "$C_{3-6}$ cycloalkyl" denotes such groups as cyclopropyl, cyclobutyl, cyclopentyl, or cyclohexyl.

As used herein "cycloalkenyl refers to ring-containing radicals having at least one carbon-carbon double bond in the ring, and having in the range about 3 up to 12 carbons atoms.

As used herein "cycloalkynyl" refers to ring-containing radicals having at least one carbon-carbon triple bond in the ring, and having in the range about 3 up to 12 carbons atoms.

As used herein, "halo" or "halogen" refers to fluoro, chloro, bromo, and iodo. "Counterion" is used to represent a small, negatively charged species such as chloride, bromide, hydroxide, acetate, sulfate, and the like. "Haloalkyl" is intended to include both branched and straight-chain saturated aliphatic hydrocarbon groups having the specified number of carbon atoms, substituted with 1 or more halogen (for example—$C_vF_w$ where v=1 to 3 and w-1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

As used herein, the term "heterocycle" or "heterocyclic" refers to a ring-containing monovalent and divalent radicals having one or more heteroatoms, independently selected from N, O and S, as part of the ring structure and comprising at least 3 and up to about 20 atoms in the rings. Heterocyclic groups may be saturated or unsaturated, containing one or more double bonds, and heterocyclic groups may contain more that one ring. The heterocyclic rings described herein may be substituted on carbon or on a nitrogen atom if the resulting compound is stable. If specifically noted, nitrogen in the heterocycle may optionally be quaternized. It is understood that when the total number of S and O atoms in the heterocycle exceeds 1, then these heteroatoms are not adjacent to one another.

Examples of heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azetidine, aziridine, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dioxolane, furyl, 2,3-dihydrofuran, 2,5-dihydrofuran, dihydrofuro[2,3-b]tetrahydrofuran, furanyl, furazanyl, homopiperidinyl, imidazolidine, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxirane, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, purinyl, pyranyl, pyrrolidine, pyrroline, pyrrolidine, pyrazinyl, pyrazolidinyl, pyrazolinyl, pyrazolyl, pyridazinyl, pyridooxazole, pyridoimidazole, pyridothiazole, pyridinyl, N-oxide-pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, thiophane, thiotetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, thiirane, triazinyl, 1,2,3-triazolyl, 1,2,4-triazolyl, 1,2,5-triazolyl, 1,3,4-triazolyl, xanthenyl.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

"Prodrugs" are intended to include any covalently bonded carriers that release the active parent drug in vivo when such prodrug is administered to a mammalian subject. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug or compound of the present invention is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of the present invention, and the like. Stable compound" and "stable structure" are meant to indicate a compound that is sufficiently robust to survive isolation to a useful degree of purity from a reaction mixture, and formulation into an efficacious therapeutic agent.

Compounds of the present invention may be administered orally, sublingually, intramuscularly, subcutaneously, topically, intranasally, intraperitoneally, intrathoracially, intravenously, epidurally, intrathecally, intracerebroventricularly and by injection into the joints.

Preferred routes of administration are orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of Alzheimer's Disease is an amount sufficient to symptomatically relieve in a warm-blooded animal, particularly a human the cognitive symptoms, to slow the progression of worsening cognitive symptoms, or to reduce in patients with cognitive symptoms the risk of getting worse (progressing to dementia or worsening the present degree of dementia).

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Salts include, but are not limited to, pharmaceutically acceptable salts. Examples of pharmaceutically acceptable salts of compounds of the present invention include: acetate, bicarbonate, carbonate, hydrobromide, hydrochloride, phosphate/diphosphate, sulfate, choline, diethanolamine, ethylenediamine, meglumine, aluminum, calcium, magnesium, potassium and sodium.

The term composition is intended to include the formulation of the active component with encapsulating material as a carrier providing a capsule in which the active component (with or without other carriers) is surrounded by a carrier which is thus in association with it. Similarly, cachets are included. Tablets, powders, cachets, and capsules can be used as solid dosage forms suitable for oral administration.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds of this invention may be prepared using the reactions and techniques described in this application. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

An example of such a process is illustrated herein.
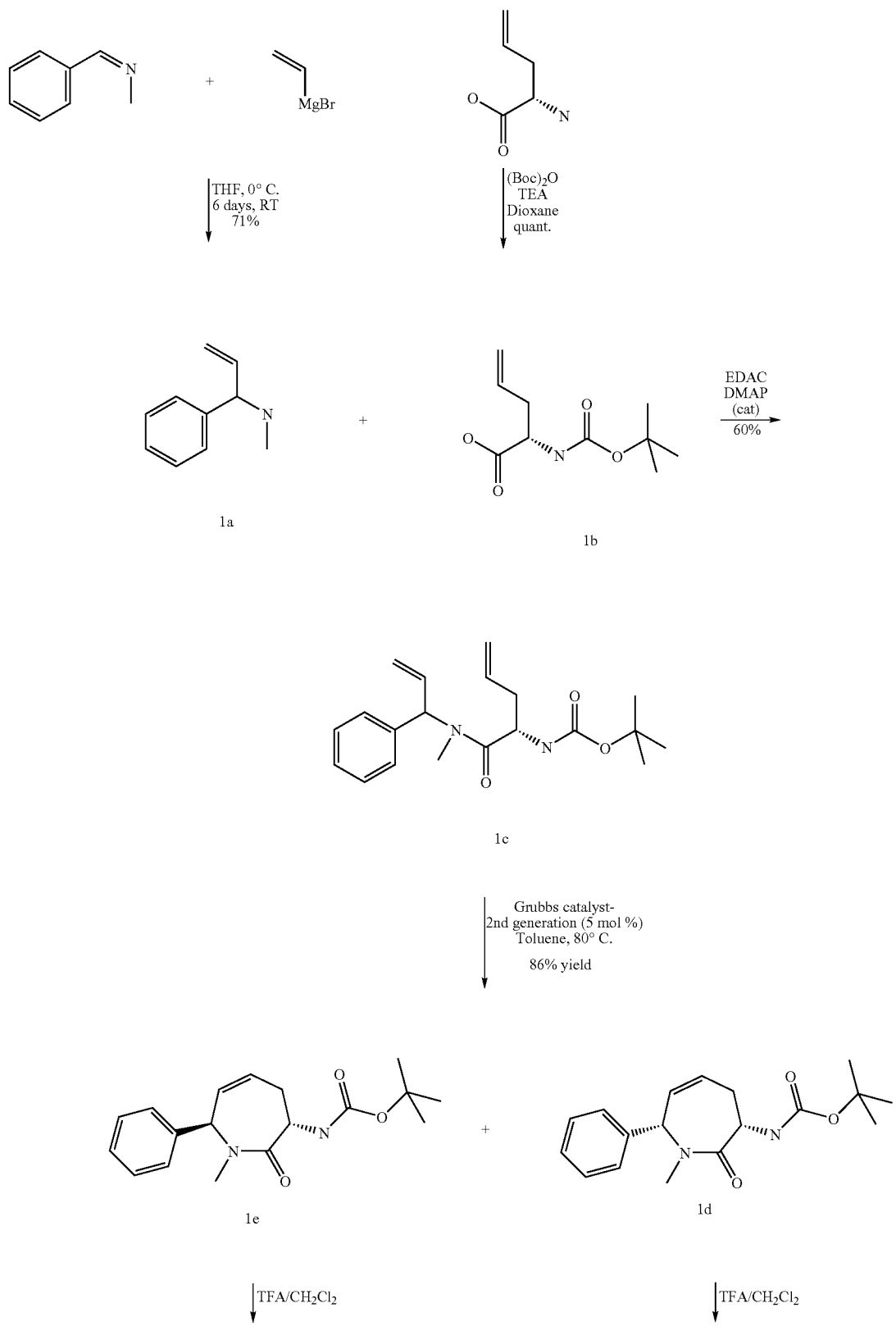

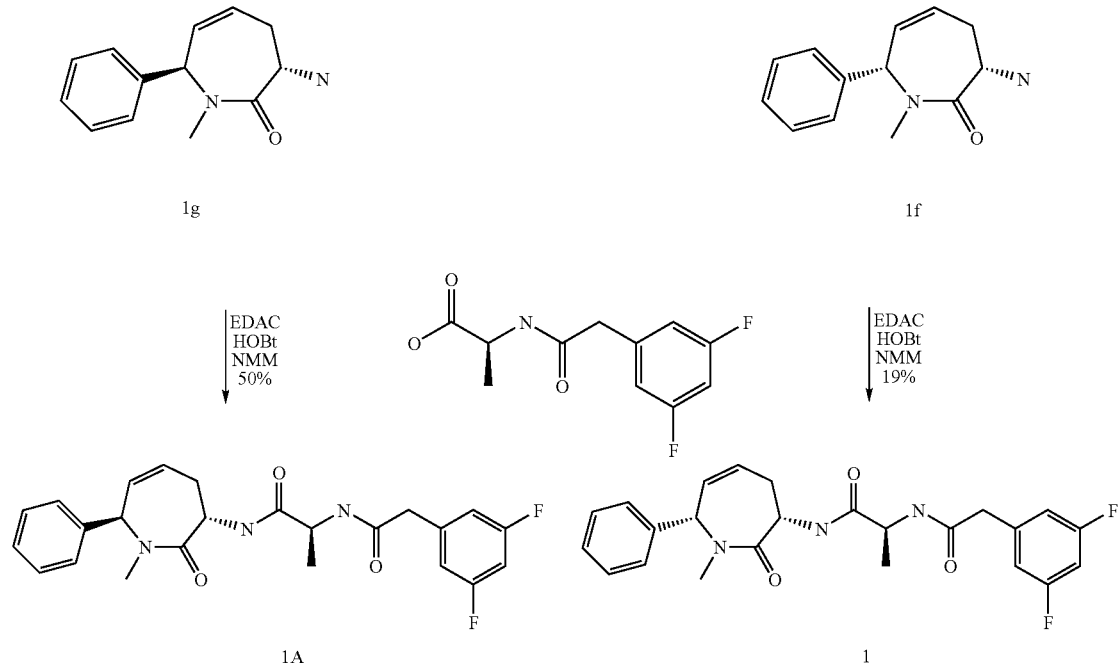

EXAMPLES

Chemical abbreviations used in the Examples are defined as follows: "BOC" denotes N-tert-butoxycarbonyl, "CBZ" denotes carbobenzyloxy; "DBU" denotes 1,8-diazabicyclo[5.4.0]undec-7-ene; "DCM" denotes dichloromethane; "DMAP" denotes 4-dimethylaminopyridine trifluoroacetic acid; "DMF" denotes N,N-dimethylformamide; "EDAC-HCl" denotes 1-Ethyl-3-(dimethylaminopropyl)carbodiimide hydrochloride; "HOBt" denotes hydroxybenzotriazole; "NMM" denotes N-methylmorpholine; "p-TSA" denotes p-toluenesulfonic acid "TBAB" denotes tetrabutylammonium bromide; "TEA" denotes triethylamine; "TFA" denotes triflouroacetic acid; "THF" denotes tetrahydrofuran, Tos-Cl denotes p-toluenesulfonyl chloride, "min." denotes minutes; "h" denotes hours; "RT" denotes room temperature. Unless otherwise noted, organic solutions were "dried" over anhydrous sodium sulfate.

HPLC Method A: Phenomenex Luna 3μ C18(2), 4.6×75 mm column. Solvents: A H$_2$O with 0.1% TFA, B=Acetonitrile with 0.1% TFA. Flow rate 2.0 mL/min. 20% B until 0.5 min then a linear gradient to 95% B at 3 min. Maintain at 95% B until 6 min LC/MS HPLC method: Agilent Zorbax 5μ SB-C8 column 2.1 mm×5 cm. Solvents: A=H$_2$O with 0.05% TFA, B=10% H$_2$O, 90% Acetonitrile, 0.05% TFA. Gradient: (10-90% B over 3 min., 90% B hold thru 4 min., −10% B at 5 min. and hold at 10% B until 6 min).

Analytical Supercritical Fluid Chromatography Method: ChiralPak AD-H, 4.6×250 mm column. Solvent: 30% isopropanol in CO$_2$. Flow rate: 2.2 mL/min for 7 min.

Preparative Supercritical Fluid Chromatography Method: ChiralPak AD-H (5μ), 21×250 mm column. Solvent: 30% isopropanol in CO$_2$. Flow rate: 50 mL/min for 7 min.

Example 1 and 1A

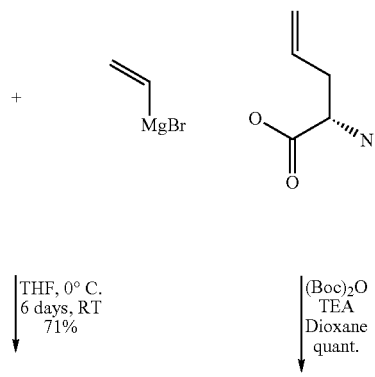

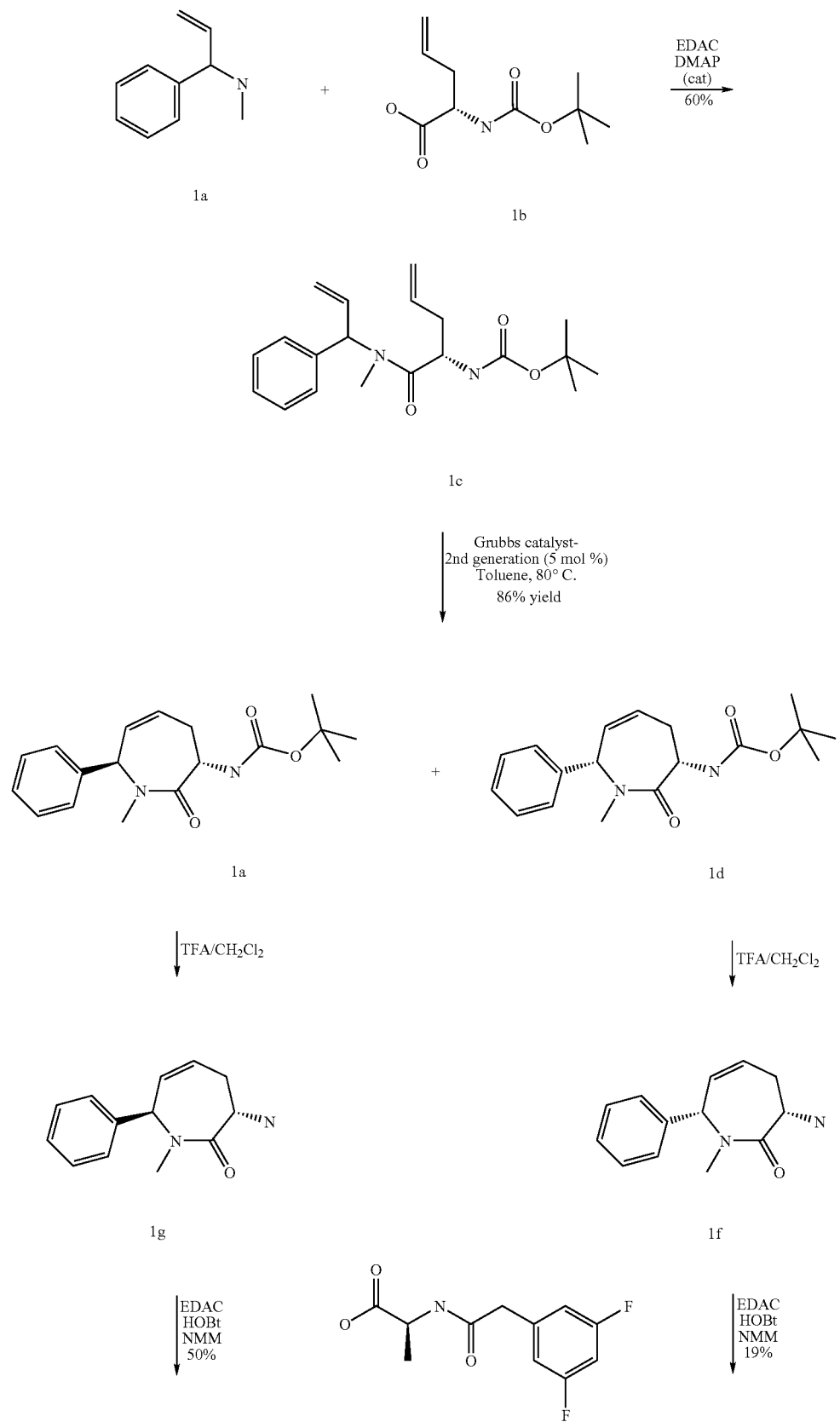

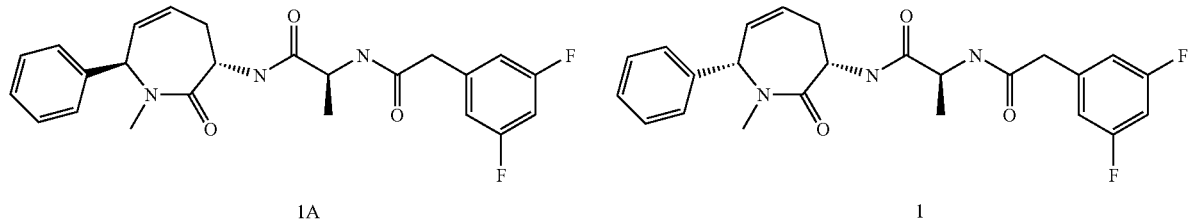

1A            1

Example 1

$N^2$-[(3,5-difluorophenyl)acetyl]-$N^1$-[(3S,7S)-1-methyl-2-oxo-7-phenyl-2,3,4,7-tetrahydro-1H-azepin-3-yl]-L-alaninamide To a solution of (3S,7S)-3-amino-1-methyl-7-phenyl-1,3,4,7-tetrahydro-2H-azepin-2-one (1f) (120 mg) in DCM (6 mL) at 0° C. under $N_2$ was added N-[(3,5-difluorophenyl)acetyl]-L-alanine (135 mg), HOBt-hydrate (186 mg), EDAC.HCl (160 mg) and N-methyl morpholine (92 mg). The reaction mixture was stirred 1 h at 0° C. and 2.5 h at room temperature, then diluted with 30% Hexanes/EtOAc (100 mL). The organic phase was consecutively washed with $H_2O$, 0.2 N HCl, saturated $NaHCO_3$, and brine, dried ($Na_2SO_4$), filtered and evaporated. The crude product was purified by flash chromatography (1% MeOH/DCM) to afford the title compound as an off-white solid (45 mg, 19%). $^1$H NMR (300 MHz, $CDCl_3$) δ 1.41 (d, 3H), 2.18-2.29 (m, 1H), 2.54 (s, 3H), 2.79-2.87 (m, 1H), 3.55 (s, 2H), 4.47-4.57 (m, 1H), 5.45-5.54 (m, 1H), 5.86 (m, 2H), 6.14-6.19 (m, 1H), 6.29 (bd, 1H), 6.69-6.76 (m, 1H), 6.84 (bd, 2H), 7.22-7.45 (m, 5H). MS APCI, m/z=464 (M+Na). LC/MS 2.52 min., Method A.

The starting amine (1f), was prepared in the following manner:

a. methyl(1-phenylprop-2-en-1-yl)amine (1a)

To a solution of N-benzylidenemethylamine (7.93 g) in THF (100 mL) at 0° C. under $N_2$ was added vinylmagnesium bromide (100 mL of a 1.0 M THF solution) dropwise. The reaction mixture stirred at 0° C. for 2 h, then at RT for 6 days. The reaction mixture was cooled to 0° C., carefully quenched with EtOH (25 mL) and concentrated. The crude product was partitioned between EtOAc and 2N HCl. The acidic aqueous layer was extracted with EtOAc (2×), and then made basic with 2N NaOH. The basic aqueous layer was extracted with EtOAc (3×). The combined EtOAc layer was washed with brine, dried ($Na_2SO_4$) filtered and concentrated to an oil. (6.87 g, 71%).

$^1$H NMR (300 MHz, $CDCl_3$) δ 2.37 (s, 3H), 4.05 (d, 1H), 5.10 (d, 1H), 5.20 (d, 1H), 5.80-5.97 (m, 1H) 7.24-7.32 (m, 5H). LC/MS 1.25 min., Method A.

b. (2S)-2-[(tert-butoxycarbonyl)amino]pent-4-enoic acid (1b)

To a suspension of L-2-amino-4-pentenoic acid (1.15 g) in Dioxane (40 mL) at RT was added triethylamine (2.5 g), water (1.0 mL), and di-tert-butyldicarbonate (4.58 g). The reaction mixture was stirred for 4 b at RT, concentrated in vacuo, diluted with saturated $NaHCO_3$ and extracted with ether (3×). The basic aqueous layer was acidified to pH 4 with 10% aq. HOAc and extracted with EtOAc (3×). The combined EtOAc layer was washed with brine, dried ($Na_2SO_4$), filtered and evaporated, then concentrated from Toluene (2×) to give a viscous oil (2.1 g, quantitative). $^1$H NMR (300 MHz, $CDCl_3$) δ 1.45 (s, 9H), 2.53-2.65 (m, 2H), 4.38-4.40 (m, 1H), 5.00-5.03 (m, 1H), 5.15-5.20 (m, 2H), 5.68-5.81 (m, 1H).). MS APCI-m/z=214 (M−1).

c. tert-butyl(1S)-1-{[methyl(phenylprop-2-en-1-yl)amino]carbonyl}but-3-en-1-yl)carbamate (1c)

To a solution of (2S)-2-[(tert-butoxycarbonyl)amino]pent-4-enoic acid (1b) (881 mg) in DCM (5 mL) at −20° C. under $N_2$ was added a mixture of EDAC.HCl (940 mg) and DMAP (12 mg) in DCM (7 mL) portionwise. Methyl(1-phenylprop-2-en-1-yl)amine (1a) (602 mg) in DCM (3 mL) was then added dropwise to the reaction mixture. The reaction mixture was stirred for 1 h at −20° C. and overnight at RT, then diluted with DCM (50 mL) and washed with 0.2 N HCl, saturated $NaHCO_3$, brine, dried ($Na_2SO_4$), filtered, and evaporated. The crude product was purified via flash chromatography (10% EtOAc/hexanes) to give the desired product as a viscous oil (838 mg, 60%). $^1$H NMR (300 MHz, $CDCl_3$) δ 1.44 (s, 9H), 2.31-2.44 (m, 1H), 2.47-2.56 (m, 1H), 2.64-2.83 (m, 3H—diastereomer/rotamer mixture), 4.73 (m, 1H), 5.08-5.18 (m, 2H), 5.22-5.49 (m, 3H), 5.72-5.84 (m, 1H) 6.03-6.16 (m, 1H), 6.39-6.44 (m, 1H) 7.28-7.34 (m, 5H). MS APCI, m/z=245 (M-t-Boc). LC/MS 2.93 min., Method A.

d. tert-butyl(3S,7S)-1-methyl-2-oxo-7-phenyl-2,3,4,7-tetrahydro-1H-azepin-3yl]carbamate (1d)

To a solution of tert-butyl(1S)-1-{[methyl(phenylprop-2-en-1-yl)amino]carbonyl}but-3-en-1-yl)carbamate (1c) (890 mg) dissolved in Toluene (100 mL) at 80° C. under $N_2$ was added Grubbs catalyst (2nd generation) (109 mg) and the reaction mixture was stirred at 80° C. for 1 h, cooled to RT and concentrated in vacuo. The crude product was directly purified via flash chromatography (gradient—5%, 10% and 20% EtOAc/hexanes) to give the title compound (1d) (412 mg) and tert-butyl[(3S,7R)-1-methyl-2-oxo-7-phenyl-2,3,4,7-tetrahydro-1H-azepin-3-yl]carbamate (1e) (293 mg) (combined yield of 86%).

1d $^1$H NMR (300 MHz, $CDCl_3$) δ 1.47 (s, 9H), 2.23-2.32 (m, 1H), 2.54 (s, 3H), 2.77-2.83 (m, 1H), 5.30-5.36 (m, 1H), 5.83-5.88 (m, 2H), 5.95 (bd, 1H), 6.09-6.15(m, 1H), 7.30-7.44 (m, 5H). MS APCI, m/z=217 (M-t-Boc). LC/MS 2.66 min., Method A. 1e $^1$H NMR (300 MHz, $CDCl_3$) δ 1.36 (bs, 9H), 2.16-2.23 (m, 1H), 2.62-2.68 (m, 1H), 3.32 (s, 3H), 4.32-4.35 (m, 1H), 5.03 (bd, 1H), 5.82 (bs, 1H), 5.94-5.98 (m, 1H), 6.04-6.09 (m, 1H), 7.26-7.40 (m, 5H). MS APCI, m/z=217 (M-t-Boc). LC/MS 2.57 min., Method A.

e. (3S,7S)-3-amino-1-methyl-7-phenyl-1,3,4,7-tetrahydro-2H-azepin-2-one (1c)

To the tert-butyl[(3S,7S)-1-methyl-2-oxo-7-phenyl-2,3,4,7-tetrahydro-1H-azepin-3-yl]carbamate (1d) (200 mg) was added a 1:3 mixture of TFA/DCM (2 ml). The reaction mixture was stirred for 1 h, then diluted with DCM and saturated aq. NaHCO$_3$. The organic layer was isolated and washed with saturated aq. NaHCO$_3$, brine, dried (Na$_2$SO$_4$) and concentrated to yield an oil (128 mg, 93%). MS APCI, m/z=217 (M+1). LC/MS 1.55 min., Method A.

Example 1A

N$^2$-[(3,5-difluorophenyl)acetyl]-N$^1$-[(3S,7R)-1-methyl-2-oxo-7-phenyl-2,3,4,7-tetrahydro-1H-azepin-3-yl]-L-alaninamide Using a procedure similar to that described in example 1, except using (3S,7R)-3-amino-1-methyl-7-phenyl-1,3,4,7-tetrahydro-2H-azepin-2-one (1g) (48 mg) to couple with N$^1$-[(3,5-difluorophenyl)acetyl]-L-alanine (54 mg), the title compound was obtained as a white solid (48 mg, 50%). $^1$H NMR (300 MHz, CDCl$_3$) δ 1.27 (d, 3H), 2.12-2.22 (m, 1H), 2.56-2.64 (m, 1H), 3.34 (s, 3H), 3.48 (s, 2H), 4.35-4.45 (m, 1H), 4.50-4.57 (m, 1H), 5.05 (bd, 1H), 5.93-5.99 (m, 1H), 6.10-6.20 (m, 2H), 6.67-6.74 (m, 1H), 6.78-6.80 (m, 2H), 7.00 (bd, 1H), 7.29-7.40 (m, 5H). MS APCI, m/z=464 (M+Na). LC/MS 2.24 min., Method A.

The starting amine (1g), was prepared in the following manner a. (3S,7R)-3-amino-1-methyl-7-phenyl-1,3,4,7-tetrahydro-2H-azepin-2-one (1g)

Using a procedure similar to that described in Example 1e except using tert-butyl[(3S,7R)-1-methyl-2-oxo-7-phenyl-2,3,4,7-tetrahydro-1H-azepin-3-yl]carbamate (1e) (80 mg), the title compound was isolated as a viscous oil (48 mg, 89%). $^1$H NMR (300 MHz, CDCl$_3$) δ 2.15-2.37 (m, 2H), 3.33 (s, 3H), 3.52-3.56 (m, 1H), 5.00 (d, 1H), 5.94-6.00 (m, 1H), 6.10-6.16 (m, 1H), 7.24-7.33 (m, 5H). MS APCI, m/z=217 (M+1). LC/MS 1.18 min., Method A.

Example 2 and 2A

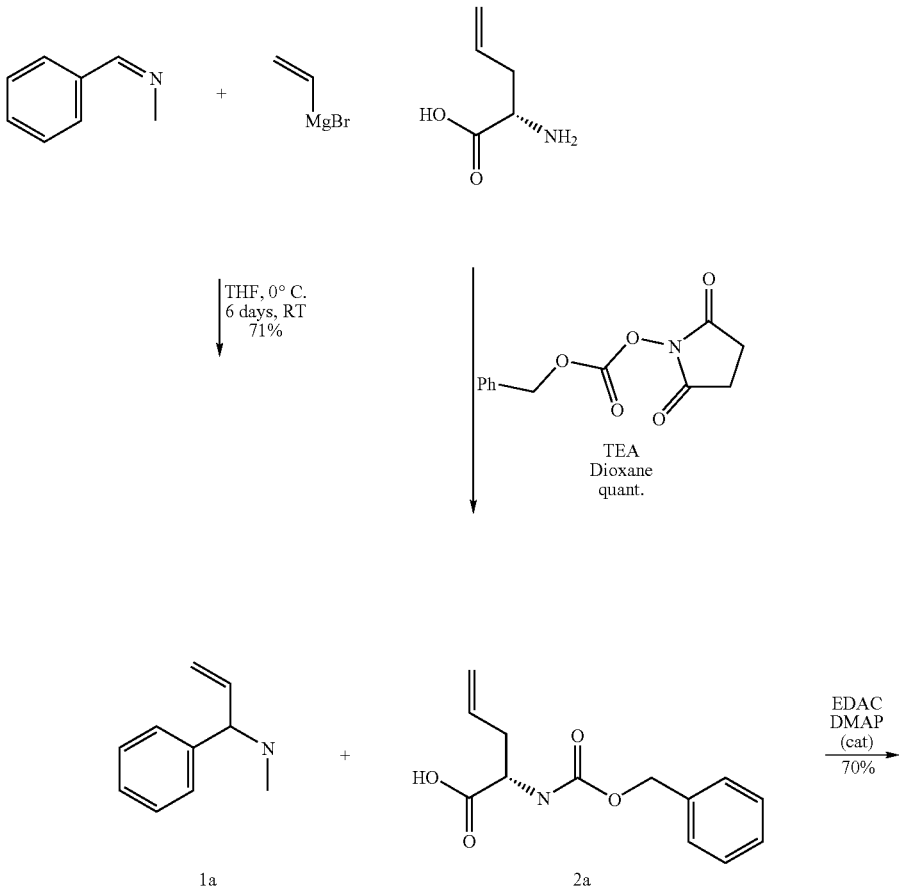

-continued
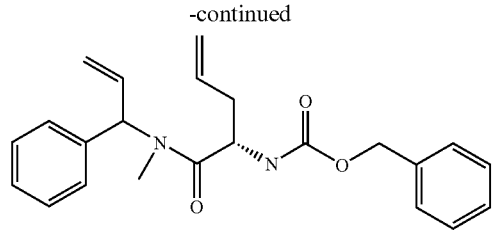
2b
| Grubbs catalyst-
2nd generation (5 mol %)
Toluene, 80° C.
89%
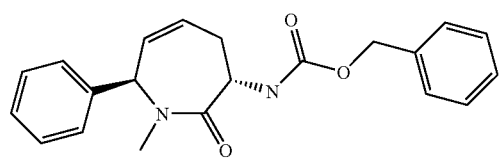   +   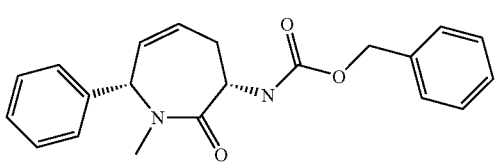
2d                                        2c
| H₂,
Pearlman's Catalyst
EtOH
85%
| H₂,
Pearlman's Catalyst
EtOH
90%
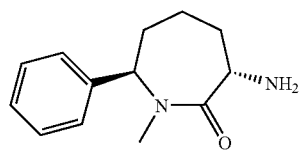                          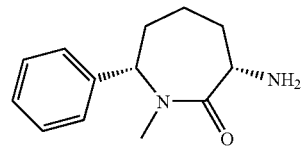
2f                                        2e
| EDAC
HOBt
NMM
71%
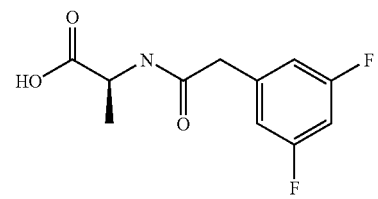
| EDAC
HOBt
NMM
70%
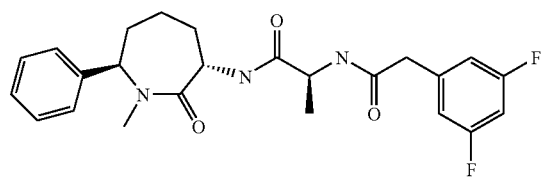                          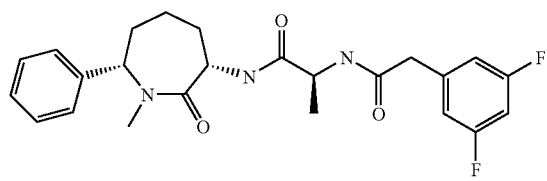
2A                                        2

Example 2

N²-[(3,5-difluorophenyl)acetyl]-N¹-[(3S,7S)-1-methyl-2-oxo-7-phenylazepan-3-yl]-L-alaninamide To a solution of (3S,7S)-3-amino-1-methyl-7-phenylazepan-2-one (2e) (57 mg) in DCM (3 mL) at 0° C. under N₂ was added N-[(3,5-difluorophenyl)acetyl]-L-alanine (95 mg), HOBt-hydrate (88 mg), EDAC.HCl (75 mg) and N-methyl morpholine (42 mg). The reaction mixture was stirred 1 h at 0° C. and 3H at room temperature, then diluted with 30% Hexanes/EtOAc (100 mL). The organic phase was consecutively washed with H₂O, 0.2 N HCl, saturated NaHCO₃, and brine, dried (Na₂SO₄), filtered and evaporated. The crude product was purified by flash chromatography (2% MeOH/DCM) to afford the title compound as an off-white solid (80 mg, 70%). ¹H NMR (300 MHz, CDCl₃) δ 1.40 (d, 3H), 1.51 (m, 1H), 1.90-2.01 (m, 3H), 2.12-2.15 (m, 2H), 2.52 (s, 3H), 3.55 (s, 2H), 4.47-4.56 (m, 1H), 4.92-5.00 (m, 2H), 6.29 (bd, 1H), 6.69-6.76 (m, 1H), 6.84 (bd, 2H), 7.27-7.41 (m, 6H). MS APCI, m/z=444 (M+1)/466 (M+Na). LC/MS 2.54 min., Method A.

The starting amine (2e), was prepared in the following manner:

a. (2S)-2-{[(benzyloxy)carbonyl]amino}pent-4-enoic acid (2a)

To a suspension of L-2-amino-4-pentenoic acid (2.0 g) in Dioxane (80 mL) at RT was added triethylamine (4.3 g), water (2.0 mL), and N-(benzyloxycarbonyloxy)succinimide (9.1 g). The reaction mixture was stirred overnight at RT, concentrated in vacuo, diluted with saturated NaHCO₃ and extracted with ether (3×). The basic aqueous layer was acidified to pH 2 with 2N HCl and extracted with EtOAc (3×). The combined EtOAc layer was washed with brine, dried (Na₂SO₄), filtered and evaporated, then concentrated from Toluene (2×) to give a viscous oil (4.51 g, quantitative). ¹H NMR (300 MHz, DMSO-d₆) δ 2.31-2.50 (m, 2H), 4.00-4.06 (m, 1H), 5.03 (s, 2H), 5.05-5.12 (m, 2H), 5.71-5.84 (m, 1H), 7.35 (m, 5H), 7.53 (d, 1H), 12.57 (bs, 1H). MS APCI, m/z=250 (M+1). LC/MS 2.30 min., Method A.

b. benzyl ((1S)-1-{[methyl(1-phenylprop-2-en-1-yl)amino]carbonyl}but-3-en-1-yl)carbamate (1b)

To a solution of (2S)-2-{[(benzyloxy)carbonyl]amino}pent-4-enoic acid (2a) (1.7 g) in DCM (8 mL) at −20° C. under N₂ was added a mixture of EDAC.HCl (1.56 g) and DMAP (18 mg) in DCM (12 mL) portionwise. Methyl(1-phenylprop-2-en-1-yl)amine (1d) (1.0 g) in DCM (5 mL) was then added dropwise to the reaction mixture. The reaction mixture was stirred for 1 h at −20° C. and overnight at RT, then diluted with DCM (100 mL) and washed with 0.2 N HCl, saturated NaHCO₃, brine, dried (Na₂SO₄), filtered, and evaporated. The crude product was purified via flash chromatography (20% EtOAc/hexanes) to give the desired product as a viscous oil (1.8 g, 70%). ¹H NMR (300 MHz, CDCl₃) δ 2.41-2.47 (m, 1H), 2.52-2.57 (m, 1H), 2.66-2.82 (m, 3H-diastereomer/rotamer mixture), 4.77 (m, 1H), 5.11-5.17 (m, 4H), 5.22-5.41 (m, 2H), 5.68-5.82 (m, 2H), 6.08 (m, 1H), 6.39-6.41 (m, 1H), 7.26-7.35 (m, 10H). MS APCI, m/z=379 (M+1). LC/MS 2.99 min., Method A.

c. benzyl [(3S,7S)-1-methyl-2-oxo-7-phenyl-2,3,4,7-tetrahydro-1H-azepin-3-yl]carbamate (2c)

To a solution of benzyl ((1S)-1-{[methyl(1-phenylprop-2-en-1-yl)amino]carbonyl}but-3-en-1-yl)carbamate (2b) (1.7 g) dissolved in Toluene (200 mL) at 80° C. under N₂ was added Grubbs catalyst (2nd generation) (191 mg) and the reaction mixture was stirred at 80° C. for 1 h, cooled to RT and concentrated in vacuo. The crude product was directly purified via flash chromatography (gradient—5%, 10%, 15% and 20% EtOAc/hexanes) to give the title compound (2c) (811 mg) and benzyl [(3S,7R)-1-methyl-2-oxo-7-phenyl-2,3,4,7-tetrahydro-1H-azepin-3-yl]carbamate (2d) (590 mg) (combined yield of 89%).

2c ¹H NMR (300 MHz, CDCl₃) δ 2.18-2.35 (m, 1H), 2.53 (s, 3H), 2.75-2.88 (m, 1H), 5.14 (d, 2H), 5.33-5.41 (m, 1H), 5.83-5.88 (m, 2H), 6.12-6.24 (m, 2H), 7.29-7.45 (m, 10H). MS APCI, m/z=351 (M+1). LC/MS 2.81 min., Method A. 2d ¹H NMR (300 MHz, CDCl₃) δ 2.18-2.27 (m, 1H), 2.63-2.69 (m, 1H), 3.32 (s, 3H), 4.37-4.45 (m, 1H), 4.94-5.05 (m, 3H), 5.94-6.14 (m, 3H), 7.25-7.38 (m, 10H). MS APCI, m/z=351 (M+1). LC/MS 2.72 min., Method A d. (3S,7S)-3-amino-1-methyl-7-phenylazepan-2-one (2e)

A mixture of benzyl [(3S,7S)-1-methyl-2-oxo-7-phenyl-2,3,4,7-tetrahydro-1H-azepin-3-yl]carbamate (2c) (216 mg) and Pearlman's catalyst (40 mg) in EtOH (7 mL) was hydrogenated at 45 psi overnight. The reaction mixture was filtered through Celite and concentrated in vacuo. The residue was dissolved in EtOAc and washed with saturated NaHCO₃, brine, dried (Na₂SO₄), filtered and concentrated to a viscous oil. The aqueous layer from above were extracted 3×50 ml DCM. The combined organic layer was washed with brine, dried (Na₂SO₄), filtered and concentrated to a viscous oil (60 mg). The two isolated oils were combined to give a 90% yield of the desired product. ¹H NMR (300 MHz, CDCl₃) δ 1.57-2.12 (m, 9H), 2.53 (s, 3H), 4.92 (d, 1H), 7.26-7.41 (m, 5H). APCI, m/z=219 (M+1). LC/MS 1.82 min., Method A

Example 2A

N²-[(3,5-difluorophenyl)acetyl]-N¹-[(3S,7R)-1-methyl-2-oxo-7-phenylazepan-3-yl]-L-alaninamide Using a procedure similar to that described in example 1, except using (3S,7R)-3-amino-1-methyl-7-phenylazepan-2-one (2f) (60 mg) to couple with N-[(3,5-difluorophenyl)acetyl]-L-alanine (1e) (67 mg), the title compound was obtained as a white solid (85 mg, 71%). ¹H NMR (300 MHz, CDCl₃) δ 1.34 (d, 3H), 1.39-1.49 (m, 1H), 1.71-1.79 (m, 1H), 1.87-2.13 (m, 3H), 2.45-2.53 (m, 1H), 3.20 (s, 3H), 3.49 (s, 2H), 4.12-4.18 (m, 1H), 4.40-4.49 (m, 1H), 4.67-4.70 (m, 1H), 6.24 (bd, 1H), 6.66-6.74 (m, 1H), 6.79-6.83 (m, 2H), 7.11-7.17 (m, 3H), 7.28-7.30 (m, 1H), 7.36-7.41 (m, 2H). MS APCI, m/z=444 (M+1)/466 (M+Na). LC/MS 2.49 min., Method A.

The starting amine (2f), was prepared in the following manner a. (3S,7R)-3-amino-1-methyl-7-phenylazepan-2-one (2f)

Using a procedure similar to that described in Example 2d except using benzyl [(3S,7R)-1-methyl-2-oxo-7-phenyl-2,3, 4,7-tetrahydro-1H-azepin-3-yl]carbamate (2d) (565 mg) the title compound was isolated as a viscous oil (295 mg, 85%). $^1$H NMR (300 MHz, CDCl$_3$) δ 1.40-1.52 (m, 1H), 1.67-1.87 (m, 6H), 2.08-2.16 (m, 1H), 2.34-2.41 (m, 1H), 3.19 (s, 3H), 4.66 (t, 1H), 7.16 (d, 2H) 7.24-7.29 (m, 1H), 7.34-7.39 (m, 1H). MS APCI, m/z=219 (M+1). LC/MS 1.63 min., Method A.
Example 3 and 3A
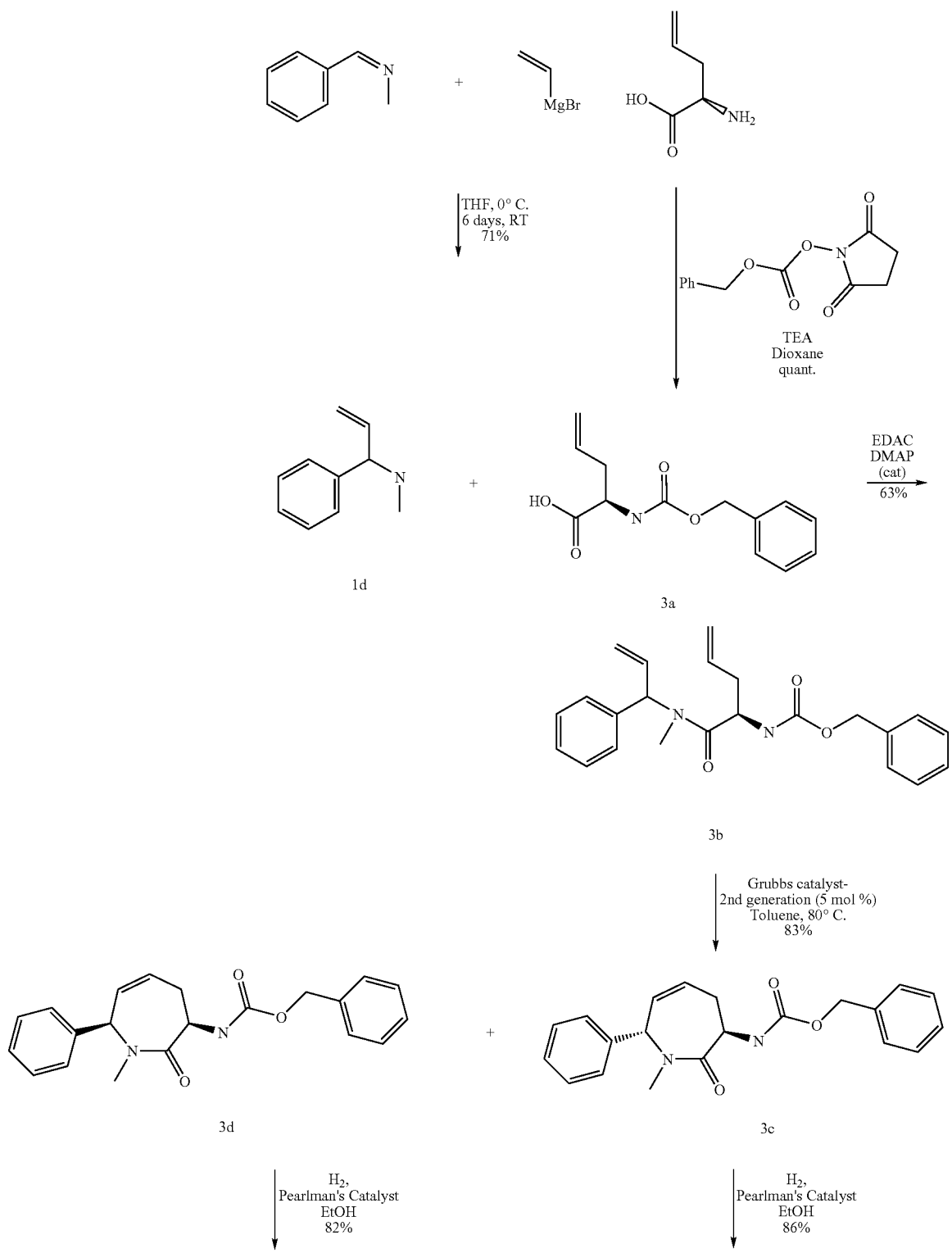

-continued

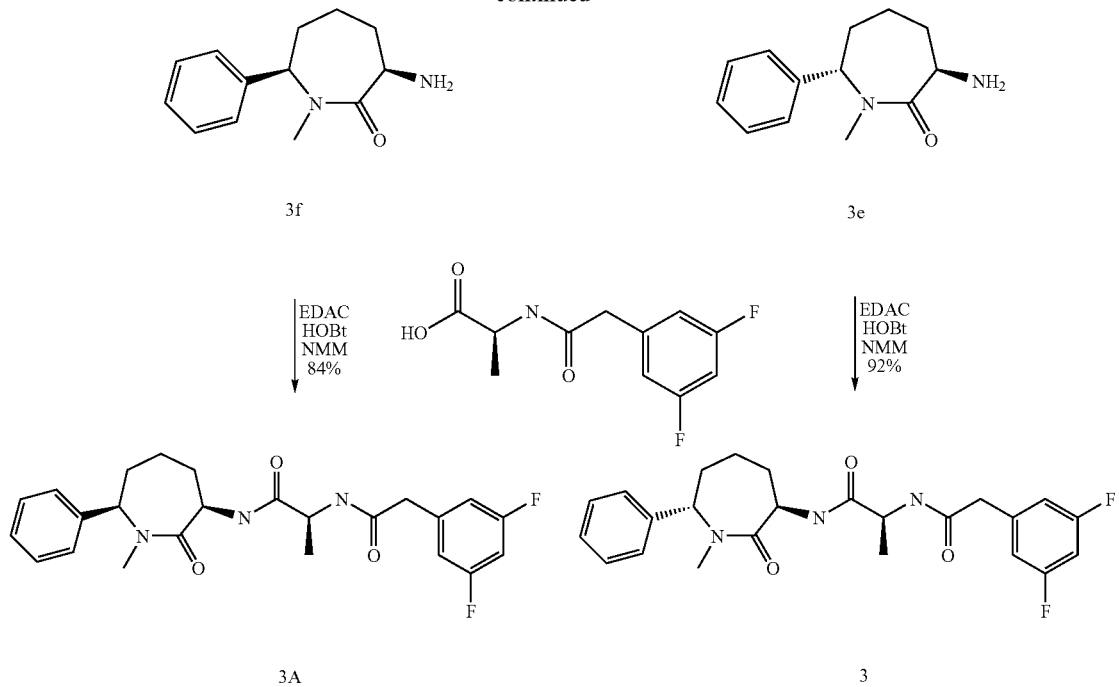

Example 3

N²-[(3,5-difluorophenyl)acetyl]-N¹-[(3R,7S)-1-methyl-2-oxo-7-phenylazepan-3-yl]-L-alaninamide To a solution of (3R,7S)-3-amino-1-methyl-7-phenylazepan-2-one (3e) (60 mg) in DCM (3 mL) at 0° C. under N₂ was added N-[(3,5-difluorophenyl)acetyl]-L-alanine (1e) (67 mg), HOBt-hydrate (92 mg), EDAC.HCl (79 mg) and N-methyl morpholine (46 mg). The reaction mixture was stirred 1 h at 0° C. and 4.5H at room temperature, then diluted with 30% Hexanes/EtOAc (100 mL). The organic phase was consecutively washed with H₂O, 0.2 N HCl, saturated NaHCO₃, and brine, dried (Na₂SO₄), filtered and evaporated. The crude product was purified by flash chromatography (2% MeOH/DCM) to afford the title compound as a white solid (110 mg, 92%). ¹H NMR (300 MHz, CDCl₃) δ 1.32 (d, 3H), 1.40-1.48 (m, 1H), 1.76-1.81 (m, 1H), 1.94-2.11 (m, 3H), 2.45-2.52 (m, 1H), 3.20 (s, 3H), 3.51 (s, 2H), 4.11-4.17 (m, 1H), 4.43-4.52 (m, 1H), 4.67-4.71 (m, 1H), 6.22 (bd, 1H), 6.68-6.75 (m, 1H), 6.82 (bd, 2H), 7.14 (bd, 3H), 7.28-7.31 (m, 1H), 7.36-7.41 (m, 2H). MS APCI, m/z=444 (M+1). LC/MS 2.24 min., Method A.

The starting amine (3e), was prepared in the following manner:

a. (2R)-2-{[(benzyloxy)carbonyl]amino}pent-4-enoic acid (3a)

To a suspension of D-2-amino-4-pentenoic acid (500 mg) in Dioxane (20 mL) at RT was added triethylamine (1.09 g), water (0.5 mL), and N-(benzyloxycarbonyloxy)succinimide (2.27 g). The reaction mixture was stirred overnight at RT, concentrated in vacuo, diluted with saturated NaHCO₃ and extracted with ether (3×). The basic aqueous layer was acidified to pH 2 with 2N HCl and extracted with EtOAc (3×). The combined EtOAc layer was washed with brine, dried (Na₂SO₄), filtered and concentrated to give a clear viscous oil (1.17 g, quantitative).

¹H NMR (300 MHz, DMSO-d₆) δ 2.29-2.50 (m, 2H), 3.98-4.06 (m, 1H), 5.03 (s, 2H), 5.05-5.12 (m, 2H), 5.71-5.84 (m, 1H), 7.35 (m, 5H), 7.54 (d, 1H), 12.57 (bs, 1H). MS APCI, m/z=250 (M+1). LC/MS 1.90 min., Method A.

b. benzyl ((1R)-1-{[methyl(1-phenylprop-2-en-1-yl)amino]carbonyl}but-3-en-1-yl)carbamate (3b)

To a solution of (2R)-2-{[(benzyloxy)carbonyl]amino}pent-4-enoic acid (3a) (1.1 g) in DCM (5 mL) at −20° C. under N₂ was added a mixture of EDAC.HCl (1.02 g) and DMAP (12 mg) in DCM (8 mL) portionwise. Methyl(1-phenylprop-2-en-1-yl)amine (1d) (650 mg) in DCM (3 mL) was then added dropwise to the reaction mixture. The reaction mixture was stirred for 1.5 h at −20° C. and 4 h at RT, then diluted with DCM (100 mL) and washed with 0.2 N HCl, saturated NaHCO₃, brine, dried (Na₂SO₄), filtered, and evaporated. The crude product was purified via flash chromatography (20% EtOAc/hexanes) to give the desired product as a viscous oil (1.04 g, 63%). ¹H NMR (300 MHz, CDCl₃) δ 2.38-2.47 (m, 1H), 2.50-2.59 (m, 1H), 2.66-2.82 (m, 3H-diastereomer/rotamer mixture), 4.77-4.80 (m, 1H), 5.08-5.17 (m, 4H), 5.22-5.48 (m, 2H), 5.69-5.82 (m, 2H), 6.03-6.14 (m, 1H), 6.39-6.43 (m, 1H), 7.25-7.35 (m, 10H). MS APCI, m/z=379 (M+1). LC/MS 2.72 min., Method A.

c. benzyl [(3R,7S)-1-methyl-2-oxo-7-phenyl-2,3,4,7-tetrahydro-1H-azepin-3-yl]carbamate (3c)

To a solution of benzyl ((1R)-1-{[methyl(1-phenylprop-2-en-1-yl)amino]carbonyl}but-3-en-1-yl)carbamate (3b) (1.01 g) dissolved in Toluene (100 mL) at 80° C. under N₂ was added Grubbs catalyst (2nd generation) (113 mg) and the reaction mixture was stirred at 80° C. for 50 min., cooled to RT and concentrated in vacuo. The crude product was directly purified via flash chromatography (gradient—10%, 15%, 20% and 30% EtOAc/hexanes) to give the title compound (3c) (331 mg) and benzyl [(3R,7R)-1-methyl-2-oxo-7-phenyl-2,3,4,7-tetrahydro-1H-azepin-3-yl]carbamate (3d) (453 mg) (combined yield of 83%).

3c $^1$H NMR (300 MHz, CDCl$_3$) δ 2.18-2.28 (m, 1H), 2.63-2.69 (m, 1H), 3.32 (s, 3H), 4.37-4.45 (m, 1H), 4.94-5.05 (m, 3H), 5.94-6.14 (m, 3H), 7.26-7.38 (m, 10H). MS APCI, m/z=351 (M+1). LC/MS 2.33 min., Method A. 3d $^1$H NMR (300 MHz, CDCl$_3$) δ 2.24-2.35 (m, 1H), 2.54 (s, 3H), 2.82-2.87 (m, 1H) 5.09-5.19 (m, 2H), 5.33-5.41 (m, 1H), 5.86-5.87 (m, 2H), 6.13-6.24 (m, 2H), 7.31-7.44 (m, 10H). MS APCI, m/z=351 (M+1)/373 (M+Na). LC/MS 2.46 min., Method A d. (3R,7S)-3-amino-1-methyl-7-phenylazepan-2-one (1e)

A mixture of benzyl [(3R,7S)-1-methyl-2-oxo-7-phenyl-2,3,4,7-tetrahydro-1H-azepin-3-yl]carbamate (3c) (310 mg) and Pearlman's catalyst (62 mg) in EtOH (8 mL) was hydrogenated at 45 psi for 6 h. The reaction mixture was filtered through Celite and concentrated in vacuo. The residue was dissolved in DCM and washed with saturated NaHCO$_3$, brine, dried (Na$_2$SO$_4$), filtered and concentrated to a viscous oil. The aqueous layer was extracted with DCM (3×). The combined organic layer was washed with brine, dried (Na$_2$SO$_4$), filtered and concentrated to a viscous oil. (166 mg, 86%).

$^1$H NMR (300 MHz, CDCl$_3$) δ 1.40-1.53 (m, 1H), 1.69-1.87 (m, 3H), 2.06-2.17 (m, 1H), 2.36-2.41 (m, 1H), 3.19 (s, 3H), 3.24 (m, 1H), 4.64-4.68 (m, 1H), 7.16 (d, 2H), 7.24-7.29 (m, 1H), 7.34-7.39 (m, 2H). MS APCI, m/z=219 (M+1). LC/MS 1.05 min., Method A

Example 3A

N$^2$-[(3,5-difluorophenyl)acetyl]-N$^1$-[(3R,7R)-1-methyl-2-oxo-7-phenylazepan-3-yl]-L-alaninamide (3A)

Using a procedure similar to that described in example 3, except using (3R,7R)-3-amino-1-methyl-7-phenylazepan-2-one (3f) (60 mg) to couple with N-[(3,5-difluorophenyl)acetyl]-L-alanine (1e) (67 mg), the title compound was obtained as a white solid (100 mg, 84%). $^1$H NMR (300 MHz, CDCl$_3$) δ 1.39 (d, 3H), 1.57 (m, 1H), 1.94 (m, 3H), 2.14 (m, 2H), 2.51 (s, 3H), 3.56 (s, 2H), 4.51-4.56 (m, 1H), 4.92-4.95 (m, 2H), 6.24 (bd, 1H), 6.70-6.75 (m, 1H), 6.83-6.85 (bd, 2H), 7.28-7.39 (m, 6H). MS APCI, m/z=444 (M+1). LC/MS 2.33 min., Method A.

The starting amine (3f), was prepared in the following manner a. (3R,7R)-3-amino-1-methyl-7-phenylazepan-2-one (3f)

Using a procedure similar to that described in Example 3d except using benzyl [(3R,7R)-1-methyl-2-oxo-7-phenyl-2,3,4,7-tetrahydro-1H-azepin-3-yl]carbamate (3d) (393 mg) the title compound was isolated as a viscous oil (216 mg, 82%). $^1$H NMR (300 MHz, CDCl$_3$) δ 1.50-1.62 (m, 1H), 1.83-1.91 (m, 2H), 1.95-2.01 (m, 2H), 2.06-2.12 (m, 1H), 2.53 (s, 3H), 4.02 (m, 1H), 4.92 (d, 1H), 7.26-7.41 (m, 5H). MS APCI, m/z=219 (M+1). LC/MS 1.12 min., Method A.

Example 4 and 4A

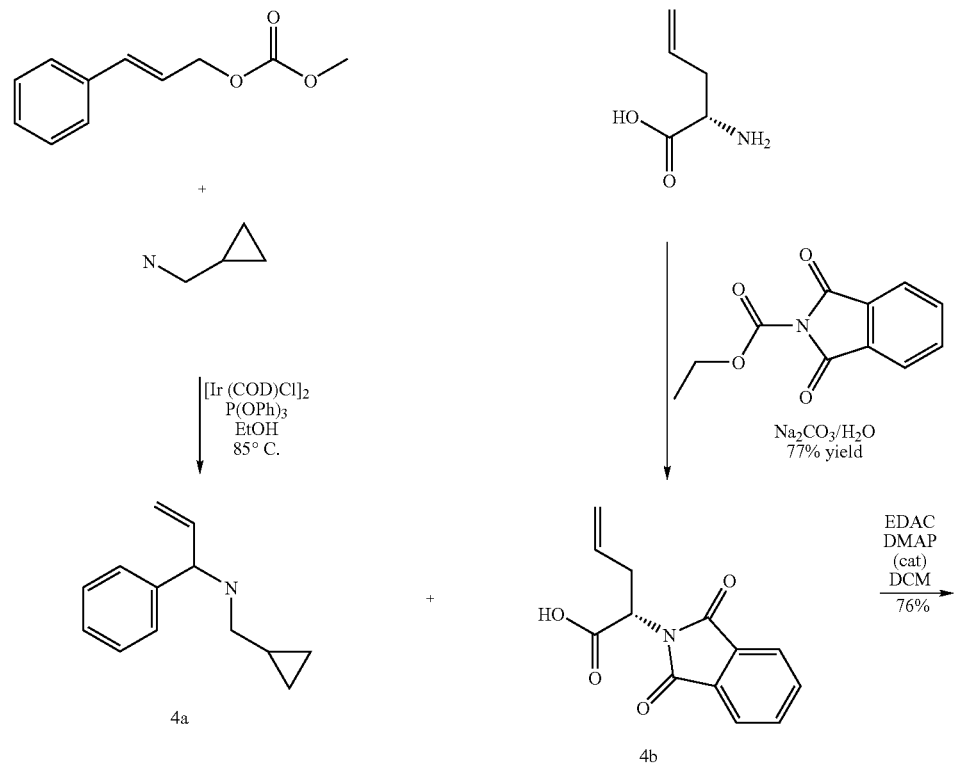

-continued
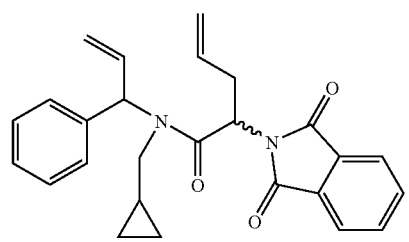
4c
Grubbs catalyst-
2nd generation (5 mol %)
Toluene, 80° C.
66% yield
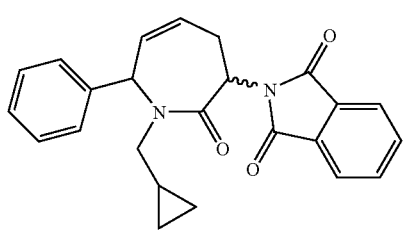
4d
H₂NNH₂, H₂O
MeOH
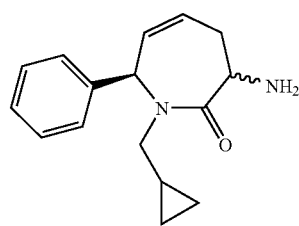   +   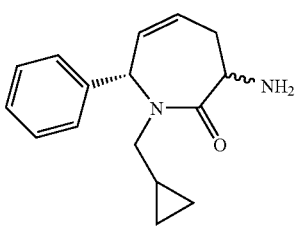
4f       4e
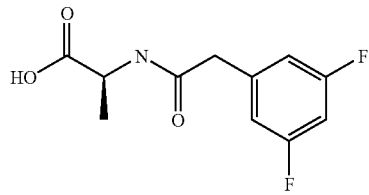
EDAC HOBt NMM 77%         EDAC HOBt NMM 65%
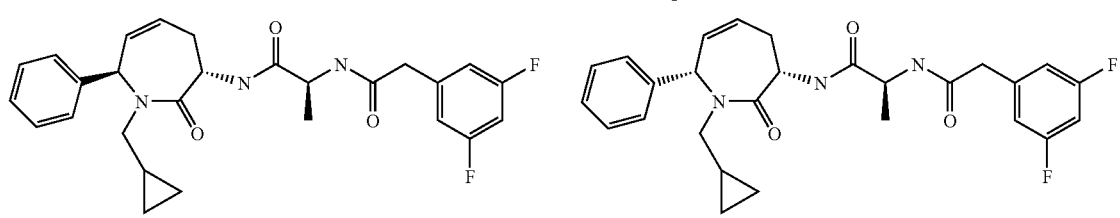
4A        4
+         +

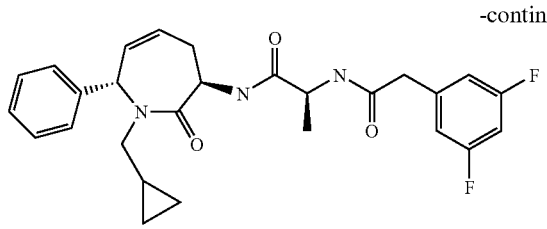
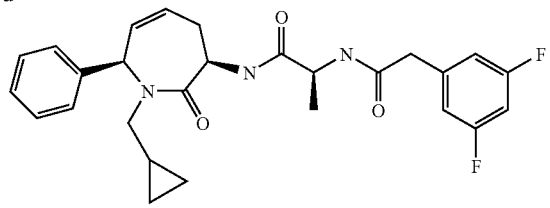

Example 4

N¹-[(3S,7S)-1-(cyclopropylmethyl)-2-oxo-7-phenyl-2,3,4,7-tetrahydro-1H-azepin-3-yl]-N²-[(3,5-difluorophenyl)acetyl]-L-alaninamide (4)

To a solution of (7S)-3-amino-1-(cyclopropylmethyl)-7-phenyl-1,3,4,7-tetrahydro-2H-azepin-2-one (4e) (40 mg) in DCM (2 mL) at 0° C. under $N_2$ was added N-[(3,5-difluorophenyl)acetyl]-L-alanine (38 mg), HOBt-hydrate (52 mg), EDAC.HCl (45 mg) and N-methyl morpholine (24 mg). The reaction mixture was stirred 1 h at 0° C. and 1.5 h at RT, then diluted with 30% hexanes/EtOAc (100 mL). The organic phase was consecutively washed with $H_2O$, 0.2 N HCl, saturated $NaHCO_3$, and brine, dried $Na_2SO_4$), filtered and evaporated. The crude product was purified by flash chromatography (gradient: 1-2% MeOH/DCM) to afford a white solid (49 mg, 65%). The mixture was further purified via chiral supercritical fluid chromatography (SFC)

Isomer 1

$^1$H NMR (300 MHz, $CDCl_3$) δ −0.15-0.10 (m, 1H), 0.00-0.06 (m, 1H), 0.19-0.28 (m, 2H), 0.51-0.56 (m, 1H), 1.40 (d, 3H), 2.17-2.29 (m, 1H), 2.77-2.87 (m, 2H), 3.22 (dd, 1H), 3.56 (s, 2H), 4.50-4.59 (m, 1H), 5.52-5.60 (m, 1H), 5.80-5.86 (m, 1H), 5.91-5.92 (m, 1H), 6.23-6.28 (m, 1H), 6.36 (bd, 1H), 6.68-6.76 (m, 1H), 6.85 (bd, 2H), 7.31 (bd, 1H), 7.36-7.43 (m, 5H). MS APCI, m/z=482 (M+1). LC/MS 2.63 min., Method A.

Isomer 2

$^1$H NMR (300 MHz, $CDCl_3$) δ −0.15-0.09 (m, 1H), 0.00-0.06 (m, 1H), 0.19-0.28 (m, 2H), 0.51-0.56 (m, 1H), 1.41 (d, 3H), 2.18-2.30 (m, 1H), 2.75-2.88 (m, 2H), 3.22 (dd, 1H), 3.55 (s, 2H), 4.48-4.57 (m, 1H), 5.51-5.59 (m, 1H), 5.80-5.85 (m, 1H), 5.92-5.93 (m, 1H), 6.23-6.28 (m, 1H), 6.38 (bd, 1H), 6.68-6.76 (m, 1H), 6.83-6.87 (m, 2H), 7.29 (bd, 1H), 7.35-7.44 (m, 5H). MS APCI, m/z=482 (M+1). LC/MS 2.62 min., Method A.

Example 4A

N¹-[(3S,7R)-1-(cyclopropylmethyl)-2-oxo-7-phenyl-2,3,4,7-tetrahydro-1H-azepin-3-yl]-N²-[(3,5-difluorophenyl)acetyl]-L-alaninamide (4A)

Utilizing (7R)-3-amino-1-(cyclopropylmethyl)-7-phenyl-1,3,4,7-tetrahydro-2H-azepin-2-one (4f), the title compound was synthesized using the same procedure as that described in Example 4. The desired product was isolated as a white solid (41 mg, 77%). The mixture was further purified via chiral supercritical fluid chromatography (SFC)

Isomer 1

$^1$H NMR (300 MHz, $CDCl_3$) δ 0.26-0.37 (m, 2H), 0.48-0.62 (m, 2H), 1.02-1.08 (m, 1H), 1.28 (d, 3H), 2.10-2.20 (m, 1H), 2.57-2.63 (m, 1H), 3.20 (dd, 1H), 3.46 (s, 2H), 4.00 (dd, 1H), 4.37-4.46 (m, 1H), 4.49-4.57 (m, 1H), 5.18 (d, 1H), 5.92-5.98 (m, 1H), 6.18-6.30 (m, 2H), 6.67-6.73 (m, 1H), 6.79 (bd, 2H), 7.05 (bd, 1H), 7.26-7.38 (m, 5H). MS APCI, m/z=482 (M+1). LC/MS 2.57 min., Method A.

Isomer 2

$^1$H NMR (300 MHz, $CDCl_3$) δ 0.26-0.36 (m, 2H), 0.49-0.62 (m, 2H), 1.02-1.10 (m, 1H), 1.27 (d, 3H), 2.10-2.20 (m, 1H), 2.55-2.64 (m, 1H), 3.20 (dd, 1H), 3.48 (s, 2H), 4.00 (dd, 1H), 4.34-4.43 (m, 1H), 4.49-4.57 (m, 1H), 5.18 (d, 1H), 5.92-5.99 (m, 1H), 6.18-6.24 (m, 2H), 6.66-6.74 (m, 1H), 6.79 (bd, 2H), 6.95 (bd, 1H), 7.26-7.38 (m, 5H). MS APCI, m/z=482 (M+1). LC/MS 2.57 min., Method A.

The starting amine (4e/4f), was prepared in the following manner:

a. N-(cyclopropylmethyl)-1-phenylprop-2-en-1-amine (4a)

To a solution of (E)-cinnamyl methyl carbonate (0.73 g) in EtOH (8 mL) at RT under $N_2$ was added (aminomethyl)cyclopropane (1 mL), triphenyl phosphite (0.096 g) and [Ir(COD)Cl]$_2$ (0.051 g). The reaction mixture was stirred at 85° C. overnight, then cooled to RT. MP-TsOH resin (1.3 mmol/g, 9 g) and EtOH (30 mL) were added to the reaction and the resulting mixture stirred for 2 hr. The resin was filtered from the reaction mixture and thoroughly washed with EtOH. The isolated resin was then washed separately with ammonia (7 N in MeOH) and the filtrate was concentrated to an oil. The crude material was purified via column chromatography (10% then 15% EtOAc/hexanes) to give the desired product (0.13 g, 18%). $^1$H NMR (300 MHz, $CDCl_3$) δ 0.045-0.092 (m, 2H), 0.42-0.49 (m, 2H), 0.92-1.02 (m, 1H), 2.33 (dd, 1H), 2.47 (dd, 1H), 4.21 (d, 1H), 5.08 (d, 1H), 5.19 (d, 1H), 5.88-5.99 (m, 1H), 7.23 (m, 5H). MS APCI, m/z=188 (M+1). LC/MS 1.25 min., Method A.

b. (2S)-2-(1,3-dioxo-1,3-dihydro-2H-isoindol-2-yl)pent-4-enoic acid (4b)

To a solution of L-2-amino-4-pentenoic acid (9.88 g) in an aqueous $Na_2CO_3$ (9.11 g, 150 mL) at RT was added N-carboethoxyphthalimide (18.8 g). The reaction mixture was stirred for 6 h at RT, gradually becoming homogeneous. The reaction mixture was transferred to a separatory funnel and extracted with DCM (3×). The basic aqueous layer was made acidic with 2N HCl and extracted with DCM (3×). The combined DCM layer was washed with brine, dried ($Na_2SO_4$), filtered and evaporated. The crude product was purified via column chromatography (2% MeOH/DCM) to give a viscous oil (20.0 g), which crystallized upon standing. $^1$H NMR (300 MHz, $CDCl_3$) δ 2.93-3.11 (m, 2H), 4.97-5.11 (m, 3H), 5.65-5.79 (m, 1H), 7.71-7.75 (m, 2H), 7.83-7.88 (m, 2H). MS APCI-m/z=246 (M+1). LCMS 1.91 min., Method A.

c. (N-(cyclopropylmethyl)-2-(1,3-dioxo-1,3-dihydro-2H-isoindol-2-yl)-N-(1-phenylprop-2-en-1-yl)pent-4-enamide (4c)

To a solution of (2S)-2-(1,3-dioxo-1,3-dihydro-2H-isoindol-2-yl)pent-4-enoic acid (4b) (166 mg) in DCM (1 mL) at −20° C. under $N_2$ was added a mixture of EDAC.HCl (156 mg) and DMAP (3 mg) in DCM (1 mL) portionwise. This mixture stirred for ten min. before N-(cyclopropylmethyl)-1-phenylprop-2-en-1-amine (4a) (127 mg) in DCM (0.5 mL) was added dropwise. The reaction mixture was stirred for 1 h at −20° C. and 3 h at RT, then diluted with DCM (50 mL) and washed with 0.2 N HCl, saturated $NaHCO_3$, brine, dried ($Na_2SO_4$), filtered, and evaporated. The crude product was purified via flash chromatography (5% then 10% EtOAc/hexanes) to give the desired product (214 mg, 76%). $^1$H NMR (300 MHz) The NMR of this compound in both $CDCl_3$ and DMSO-$d_6$ (with elevated temperatures) was complex, thus limiting interpretation. MS APCI, m/z=415 (M+1). LC/MS 2.86 min., Method A.

d. 2-[1-(cyclopropylmethyl)-2-oxo-7-phenyl-2,3,4,7-tetrahydro-1H-azepin-3-yl]-1H-isoindole-1,3(2H)-dione (4d)

To a solution of (N-(cyclopropylmethyl)-2-(1,3-dioxo-1,3-dihydro-2H-isoindol-2-yl)-N-(1-phenylprop-2-en-1-yl)pent-4-enamide (4c) (210 mg) dissolved in Toluene (25 mL) at 80° C. under $N_2$ was added Grubbs catalyst (2nd generation) (21 mg) and the reaction mixture was stirred at 80° C. for 1 h, then cooled to RT. DMSO (0.1 mL) was added to the reaction mixture which was stirred for 2 h, then concentrated. The crude product was directly purified via flash chromatography (gradient—5%, 10% and 15% EtOAc/hexanes) to give a diastereomeric mixture (1.5:1) of the title compound (128 mg, 66%). $^1$H NMR (300 MHz, $CDCl_3$) δ 0.03-0.09 (m, 1H), 0.22-0.34 (m, 2H), 0.46-0.57 (m, 1H), 0.66-0.72 (m, 0.6H), 1.03-1.09 (m, 0.4H), 2.42-2.48 (m, 1H), 2.98 (dd, 0.6H), 3.20 (dd, 0.4H), 3.55 (dd, 0.6H), 3.61-3.74 (m, 1H), 3.94 (dd, 0.4H), 5.09 (dd, 0.4H), 5.28 (bd, 0.4H), 5.57 (dd, 0.6H), 5.77 (d, 0.6H), 6.00-6.08 (m, 1H), 6.26-6.35 (m, 1H), 7.35-7.48 (m, 5H), 7.65-7.88 (m, 4H). MS APCI, m/z=387 (M+1). LC/MS 2.66 min., Method A.

e. (7S)-3-amino-1-(cyclopropylmethyl)-7-phenyl-1,3,4,7-tetrahydro-2H-azepin-2-one (4e) and (7R)-3-amino-1-(cyclopropylmethyl)-7-phenyl-1,3,4,7-tetrahydro-2H-azepin-2-one (4f)

To 2-[1-(cyclopropylmethyl)-2-oxo-7-phenyl-2,3,4,7-tetrahydro-1H-azepin-3-yl]-1H-isoindole-1,3(2H)-dione (4d) (126 mg) dissolved in MeOH (4 mL) was added hydrazine hydrate (0.033 mL) and the mixture was stirred overnight at RT. A white precipitate formed in solution. The reaction mixture was diluted with ether and the precipitate was filtered and washed with ether. The etheral filtrate was concentrated and the resulting residue dissolved in DCM. The DCM solution was washed with $H_2O$ and brine, dried ($Na_2SO_4$) and concentrated to an oil. The diastereomeric mixture was separated via preparative plate chromatography (eluent 10% MeOH/DCM) to give (7R)-3-amino-1-(cyclopropylmethyl)-7-phenyl-1,3,4,7-tetrahydro-2H-azepin-2-one (4f) (28 mg) and (7S)-3-amino-1-(cyclopropylmethyl)-7-phenyl-1,3,4,7-tetrahydro-2H-azepin-2-one (4e) (40 mg) (combined yield of 82%).

4f
$^1$H NMR (300 MHz, $CDCl_3$) δ 0.25-0.36 (m, 2R), 0.47-0.58 (m, 2H), 1.03-1.11 (m, 1H), 2.14-2.36 (m, 4H), 3.20 (dd, 1H), 3.52-3.56 (m, 1H), 4.01 (dd, 1H), 5.14 (d, 1H), 5.93-6.00 (m, 1H), 6.18-6.26 (m, 1H), 7.27-7.43 (m, 5H). MS APCI, m/z=257 (+1). LC/MS 1.51 min., Method A.

4e (Sample Contains 12% 4f)
$^1$H NMR (300 MHz, $CDCl_3$) δ −0.15-−0.073 (m, 1H), 0.00-0.08 (m, 1H), 0.19-0.30 (m, 2H), 0.50-0.57 (m, 1H, 2.21-2.32 (m, 1H), 2.58-2.66 (m, 1H), 2.87 (dd, 1H), 3.21 (dd, 1H), 4.53-4.58 (m, 1H), 5.82-5.90 (m, 2H), 6.24-6.29 (m, 1H), 7.32-7.43 (m, 5H). MS APCI, m/z=257 (M+1). LC/MS 1.61 min., Method A.

Example 5 and 5A

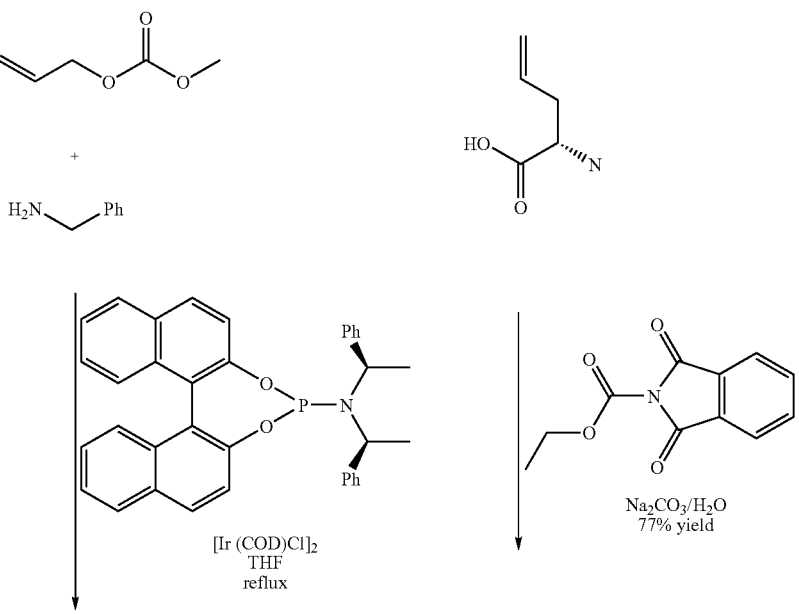

-continued
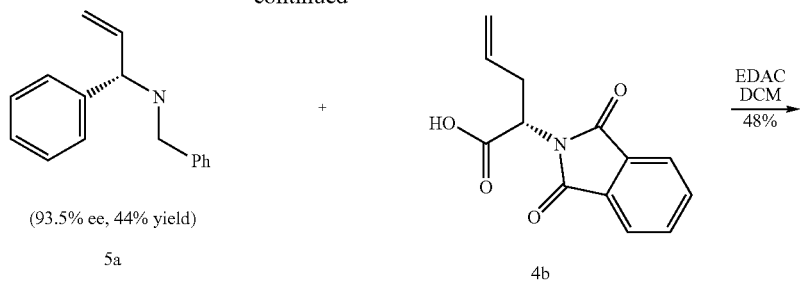
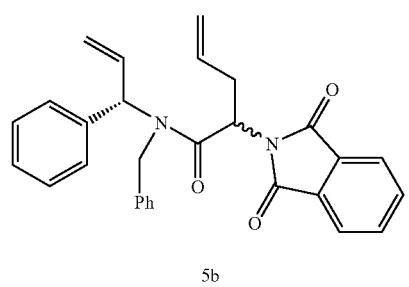
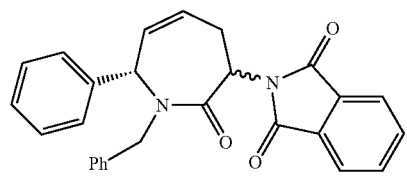
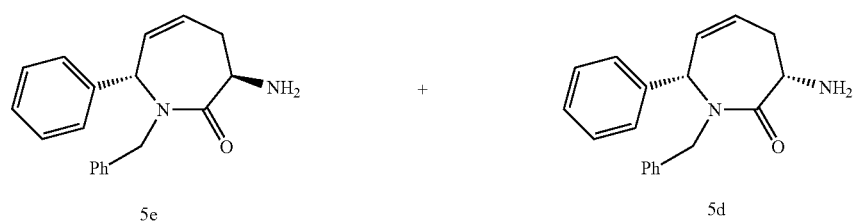
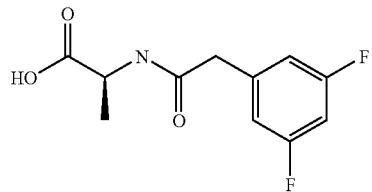

-continued

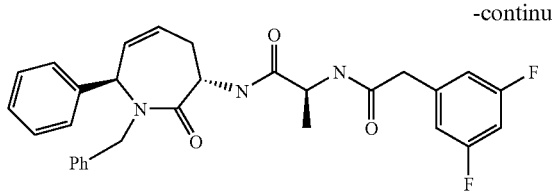

5A

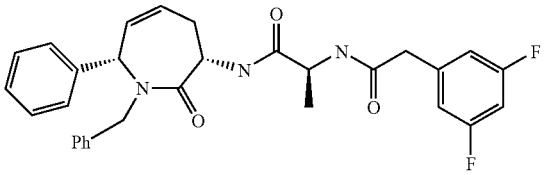

5

Example 5

N$^1$-[(3S,7S)-benzyl-2-oxo-7-phenyl-2,3,4,7-tetrahydro-1H-azepin-3-yl]-N$^2$-[(3,5-difluorophenyl)acetyl]-L-alaninamide (5)

To a solution of (3S,7S)-3-amino-1-benzyl-7-phenyl-1,3,4,7-tetrahydro-2H-azepin-2-one (5d) (40 mg) in DCM (2 mL) at 0° C. under N$_2$ was added N-[(3,5-difluorophenyl)acetyl]-L-alanine (33 mg), HOBt-hydrate (46 mg), EDAC.HCl (39 mg) and N-methyl morpholine (22 mg). The reaction mixture was stirred 1 h at 0° C. and 3 h at RT, then diluted with 30% hexanes/EtOAc (100 mL). The organic phase was consecutively washed with H$_2$O, 0.2 N HCl, saturated NaHCO$_3$, and brine, dried (Na$_2$SO$_4$), filtered and evaporated. The crude product was purified by flash chromatography (1%-2% MeOH/DCM) to afford a white solid (50 mg, 71%). Sample contains approx. 20% 5A.

$^1$H NMR (300 MHz, CDCl$_3$) δ 1.42 (d, 3H), 2.29-2.40 (m, 1H), 2.84-2.92 (m, 1H), 3.55 (s, 2H), 4.03 (d, 1H), 4.47-4.56 (m, 1H), 4.63 (d, 1H), 5.53-5.76 (m, 1H), 5.83-5.92 (m, 2H), 6.07-6.12 (m, 1H), 6.27 (bd, 1H), 6.70-6.86 (m, 4H), 7.12-7.15 (m, 3H), 7.20-7.35 (m, 7H). $^{19}$F NMR (300 MHz, CDCl$_3$)δ −108.96. MS APCI, m/z=518(M+1). LC/MS 2.79 min., Method A.

Example 5A

N$^1$-[(3S,7R)-1-benzyl-2-oxo-7-phenyl-2,3,4,7-tetrahydro-1H-azepin-3-yl]-N$^2$-[(3,5-difluorophenyl)acetyl]-L-alaninamide (5A)

Utilizing (3R,7S)-3-amino-1-benzyl-7-phenyl-1,3,4,7-tetrahydro-2H-azepin-2-one (5e), the title compound was synthesized using the same procedure as that described for Example 5. The desired product was isolated as a white solid (25 mg, 64%).

$^1$H NMR (300 MHz, CDCl$_3$) δ 1.31 (d, 3H), 2.18-2.28 (m, 1H), 2.59-2.68 (m, 1H), 3.48 (s, 2H), 4.41-4.50 (m, 1H), 4.60-4.65 (m, 1H), 5.06 (d, 1H), 5.58 (d, 1H), 5.87-6.02 (m, 2H), 6.26 (bd, 1H), 6.67-6.83 (m, 1H), 6.80 (bd, 2H), 7.12 (bd, 1H), 7.20-7.36 (m, 10H). $^{19}$F NMR (300 MHz, CDCl$_3$) δ −109.1 MS APCI, m/z=518(M+1). LC/MS 2.77 min., Method A.

The starting amine (5d/5e), was prepared in the following manner:

a. (1S)-N-benzyl-1-phenylprop-2-en-1-amine (5a)

To a solution of (E)-cinnamyl methyl carbonate (0.50 g) in THF (10 mL) at RT under N$_2$ was added the (S)-(1,1'-Dinaphthyl-2,2'-di-(S,S)-1-phenylethylphosphoramidite* (0.140 g), [Ir(COD)Cl]$_2$ (0.035 g) and benzylamine (0.557 g). The reaction mixture was stirred at reflux overnight, then cooled to RT. MP-TsOH resin (4.07 mmol/g, 2 g) was added to the reaction mixture and the resulting mixture stirred for 1 hr. The resin was then filtered from the reaction mixture and thoroughly washed with MeOH. The isolated resin was then washed separately with ammonia (7 N in MeOH) and the filtrate was concentrated to an oil. The crude material was purified via column chromatography (5% EtOAc/hexanes) to give the desired product (0.26 g, 93.5% ee, 44% yield). $^1$H NMR (300 MHz, CDCl$_3$) δ 3.73 (s, 2H), 4.22 (d, 1H), 5.12 (d, 1H), 5.22 (dd, 1H), 5.89-6.01 (m, 1H), 7.21-7.38 (m, 10H). MS APCI, m/z=224 (M+1). LC/MS 1.79 min., Method A.

b. N-benzyl-2-(1,3-dioxo-1,3-dihydro-2H-isoindol-2-yl)-N-[(1S)-1-phenylprop-2-en-1-yl]pent-4-enamide (5b)

To a solution of (S)-N-benzyl-1-phenylprop-2-en-1-amine (5a) (240 mg) in DCM (5 mL) at RT under N$_2$ was added (2S)-2-(1,3-dioxo-1,3-dihydro-2H-isoindol-2-yl)pent-4-enoic acid (4b) (263 mg) and EDAC.HCl (224 mg). The mixture was stirred overnight at RT, then diluted with 30% hexanes/EtOAc and washed with H$_2$O, 0.2 N HCl, saturated NaHCO$_3$, brine, dried (Na$_2$SO$_4$), filtered, and concentrated to a white foamy solid (233 mg, 48%). $^1$H NMR (300 MHz) The NMR of this compound in both CDCl$_3$ and DMSO-d$_6$ (with elavated temperatures) was complex, thus limiting interpretation. MS APCI, m/z=451 (M+1). LC/MS 3.13 min., Method A.

c. 2-[(7S)-1-benzyl-2-oxo-7-phenyl-2,3,4,7-tetrahydro-1H-azepin-3-yl]-1H-isoindole-1,3(2H)-dione (5c)

To a solution of N-benzyl-2-(1,3-dioxo-1,3-dihydro-2H-isoindol-2-yl)-N-[(1S)-1-phenylprop-2-en-1-yl]pent-4-enamide (5b) (230 mg) dissolved in Toluene (25 mL) at 80° C. under N$_2$ was added Grubbs catalyst (2nd generation) (22 mg) and the reaction mixture was stirred at 80° C. for 2 h, then cooled to RT. DMSO (0.1 mL) was added to the reaction and the mixture stirred for 1 h, then concentrated. The crude product was directly purified via flash chromatography (gradient—5%, 10%, 15% EtOAc/hexanes) to give a diastereomeric mixture (1.5:1) of the title compound. (168 mg, 78%).

$^1$H NMR (300 MHz, DMSO-d$_6$) δ 2.55-2.61 (m, 1H), 3.40-3.55 (m, 1H), 4.08 (d, 0.6H), 4.23 (d, 0.4H), 4.65 (d, 0.6H), 4.95 (dd, 0.4H), 5.31 (d, 0.4H), 5.36 (d, 0.4H), 5.45 (dd, 0.6H), 5.78 (bd, 0.6H), 6.04-6.09 (m, 1H), 6.21-6.28 (m, 1H), 6.94 (d, 1H), 7.16-7.44 (m, 9H), 7.84-7.95 (m, 4H). MS APCI, m/z=423 (M+1). LC/MS 3.00 min., Method A.

d. (3S,7S)-3-amino-1-benzyl-7-phenyl-1,3,4,7-tetrahydro-2H-azepin-2-one (5d) and (3R,7S)-3-amino-1-benzyl-7-phenyl-1,3,4,7-tetrahydro-2H-azepin-2-one (5e)

To 2-[(7S)-1-benzyl-2-oxo-7-phenyl-2,3,4,7-tetrahydro-1H-azepin-3-yl]-1H-isoindole-1,3(2H)-dione (5c) (126 mg) dissolved in MeOH (4 mL) was added hydrazine hydrate (0.036 mL) and the mixture was stirred overnight at RT. A white precipitate formed in solution. The reaction mixture was diluted with ether and the precipitate was filtered and washed with ether. The etheral filtrate was concentrated and the resulting residue dissolved in DCM. The DCM solution was washed with $H_2O$ and brine, dried ($Na_2SO_4$) and concentrated. The diastereomeric mixture was separated via preparative plate chromatography (eluent 10% MeOH/DCM) to give (3R,7S)-3-amino-1-benzyl-7-phenyl-1,3,4,7-tetrahydro-2H-azepin-2-one (5e) and (3S,7S)-3-amino-1-benzyl-7-phenyl-1,3,4,7-tetrahydro-2H-azepin-2-one (5d) (combined yield of 72%).

5e
$^1$H NMR (300 MHz, CDCl$_3$) δ 2.23-2.43 (m, 2H), 3.62 (dd, 1H), 4.22 (d, 1H), 5.02 (d, 1H), 5.63 (d, 1H), 5.85-6.03 (m, 2H), 7.19-7.35 (m, 10H). MS APCI, m/z=293 (M+1). LC/MS 1.89 min., Method A.

5d (Sample Contains 20% 5e)
$^1$H NMR (300 MHz, CDCl$_3$) δ 2.33-2.44 (m, 1H), 2.63-2.71 (m, 1H), 4.18 (d, 1H), 4.56 (bd, 2H), 5.84-5.88 (m, 2H), 6.02-6.12 (m, 1H), 6.79-6.82 (m, 2H), 7.11-7.15 (m, 3H), 7.22-7.32 (m, 5H). MS APCI, m/z=293 (M+1). LC/MS 1.89 min., Method A.

Example 6 and 6A

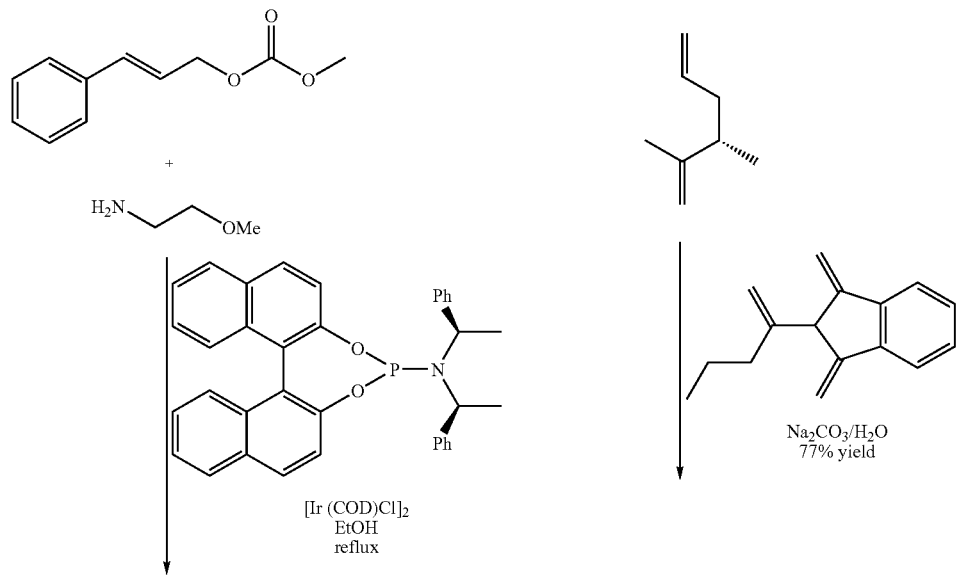

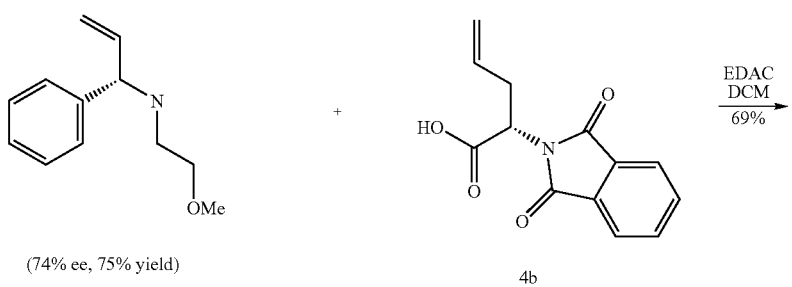

-continued
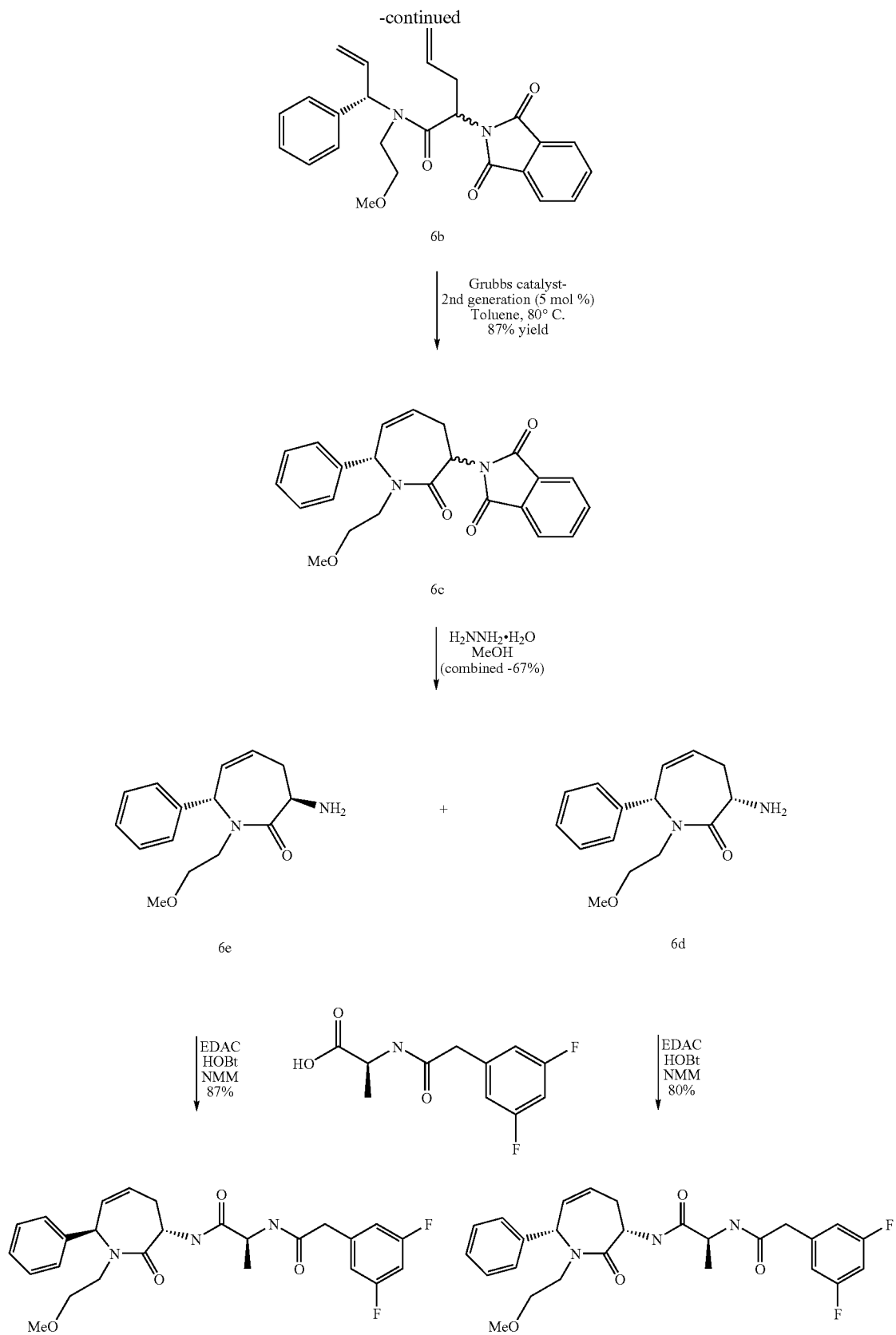

Example 6

N²-[(3,5-difluorophenyl)acetyl]-N¹-[(3S,7S)-1-(2-methoxyethyl)-2-oxo-7-phenyl-2,3,4,7-tetrahydro-1H-azepin-3-yl]-L-alaninamide (6)

To a solution of (3S,7S)-3-amino-1-(2-methoxyethyl)-7-phenyl-1,3,4,7-tetrahydro-2H-azepin-2-one (6d) (55 mg) in DCM (4 mL) at 0° C. under N₂ was added N-[(3,5-difluorophenyl)acetyl]-L-alanine (51 mg), HOBt-hydrate (71 mg), EDAC.HCl (61 mg) and N-methyl morpholine (34 mg). The reaction mixture was stirred 1 h at 0° C. and 3 h at RT, then diluted with 30% hexanes/EtOAc (100 mL). The organic phase was consecutively washed with H₂O, 0.2 N HCl, saturated NaHCO₃, and brine, dried (Na₂SO₄), filtered and evaporated. The crude product was purified by flash chromatography (1%-2% MeOH/DCM) to afford a white solid (82 mg, 80%).

¹H NMR (300 MHz, CDCl₃) δ 1.41 (d, 3H), 2.17-2.28 (m, 1H), 2.79-2.87 (m, 1H), 2.92-3.08 (m, 2H) 3.14 (s, 3H), 3.16-3.24 (m, 1H), 3.53-3.62 (m, 1H), 3.55 (s, 2H), 4.45-4.55 (m, 1H), 5.48-5.56 (m, 1H), 5.79-5.89 (m, 2H), 6.19-6.27 (m, 2H), 6.70-6.76 (m, 1H), 6.85 (bd, 2H), 7.21 (bd, 1H), 7.36-7.46 (m, 5H). ¹⁹F NMR (300 MHz, CDCl₃)δ –108.98. MS APCI, m/z=486(M+1). LC/MS 2.12 min., Method A.

Example 6A

N²-[(3,5-difluorophenyl)acetyl]-N¹-[(3S,7R)-1-(2-methoxyethyl)-2-oxo-7-phenyl-2,3,4,7-tetrahydro-1H-azepin-3-yl]-L-alaninamide (6A)

Utilizing (3R,7S)-3-amino-1-(2-methoxyethyl)-7-phenyl-1,3,4,7-tetrahydro-2H-azepin-2-one (6e), the title compound was synthesized using the same procedure as that described for Example 6. The desired product was isolated as a white solid (89 mg, 87%).

¹H NMR (300 MHz, CDCl₃). δ 1.29 (d, 3H), 2.08-2.19 (m, 1H), 2.56-2.63 (m, 1H), 3.33 (s, 3H), 3.40-3.45 (m, 1H), 3.48 (s, 2H), 3.53-3.65 (m, 2H), 4.27-4.35 (m, 1H), 4.36-4.45 (m, 1H), 4.51-4.58 (m, 1H), 5.24 (d, 1H), 5.90-5.95 (m, 1H), 6.14-6.19 (m, 2H), 6.67-6.74 (m, 1H), 6.79 (bd, 2H), 6.99 (bd, 1H), 7.27-7.39 (m, 5H). ¹⁹F NMR (300 MHz, CDCl₃)δ–109.13. MS APCI, m/z=486(M+1). LC/MS 2.09 min., Method A.

The starting amine (6d/6e), was prepared in the following manner:

a. (1S)-N-(2-methoxyethyl)-1-phenylprop-2-en-1-amine (6a)

To a solution of (E)-cinnamyl methyl carbonate (0.50 g) in EtOH (10 mL) at RT under N₂ was added the (S)-(1,1'-Dinaphthyl-2,2'-di-(S,S)-1-phenylethylphosphoramidite (0.140 g), [Ir(COD)Cl]₂ (0.035 g) and 2-methoxyethylamine (0.39 g). The reaction mixture was stirred at 50° C. for 1.5 h, then cooled to RT. The reaction mixture was diluted with ether and washed with 2N HCl (×3). The combined acidic aqueous layer was made basic with aqueous 2N NaOH and extracted with DCM (×3). The combined DCM layer was washed with brine, dried (Na₂SO₄), filtered and evaporated The crude material was purified via column chromatography (gradient—5%, 10%, 15% EtOAc/hexanes) to give the desired product (0.375 g, 74% ee, 75% yield). ¹H NMR (300 MHz, CDCl₃) δ 2.62-2.81 (m, 2H), 3.34 (s, 3H), 3.49 (t, 2H), 4.18 (d, 1H), 5.09 (d, 1H), 5.20 (dd, 1H), 5.88-5.99 (m, 1H), 7.22-7.35 (m, 5H). MS APCI, m/z=192 (M+1). LC/MS 0.66 min., Method A.

b. 2-(1,3-dioxo-1,3-dihydro-2H-isoindol-2-yl)-N-(2-methoxyethyl)-N-[(1S)-1-phenylprop-2-en-1-yl]pent-4-enamide (6b)

To a solution of (1S)-N-(2-methoxyethyl)-1-phenylprop-2-en-1-amine (6a) (350 mg) in DCM (8 mL) at 0° C. under N₂ was added (2S)-2-(1,3-dioxo-1,3-dihydro-2H-isoindol-2-yl)pent-4-enoic acid (4b) (470 mg) and EDAC.HCl (444 mg). The mixture was stirred for 2 h at 0° C. and 4 h at RT, then diluted with 30% hexanes/EtOAc and washed with H₂O, 0.2 N HCl, saturated NaHCO₃, brine, dried (Na₂SO₄), filtered, and concentrated to a clear oil (548 mg, 69%). ¹H NMR (300 MHz) The NMR of this compound in both CDCl₃ and DMSO-d₆ (with elavated temperatures) was complex, thus limiting interpretation. MS APCI, m/z=419 (M+1). LC/MS 2.76 min., Method A.

c. 2-[(7S)-1-(2-methoxyethyl)-2-oxo-7-phenyl-2,3,4,7-tetrahydro-1H-azepin-3-yl]-1H-isoindole-1,3(2H)-dione (6c)

To a solution of 2-(1,3-dioxo-1,3-dihydro-2H-isoindol-2-yl)-N-(2-methoxyethyl)-N-[(1S)-1-phenylprop-2-en-1-yl]pent-4-enamide (6b) (524 mg) dissolved in Toluene (50 mL) at 80° C. under N₂ was added Grubbs catalyst (2nd generation) (53 mg) and the reaction mixture was stirred at 80° C. for 1 h, then cooled to RT. DMSO (0.2 mL) was added to the reaction and the mixture stirred for 1 h, then concentrated. The crude product was directly purified via flash chromatography (gradient—5%, 10%, 20%, 30% EtOAc/hexanes) to give a diastereomeric mixture (1:1) of the title compound. (426 mg, 87%).

¹H NMR (300 MHz, CDCl₃) δ 2.40-2.46 (m, 2H), 3.20 (s, 3H), 3.22-3.78 (m, 9H), 3.32 (s, 3H), 4.22-4.30 (m, 1H), 5.10 (dd, 1H), 5.34 (bd, 1H), 5.50 (dd, 1H), 5.74 (bd, 1H), 5.99-6.06 (m, 2H), 6.22-6.33 (m, 2H), 7.35-7.49 (m, 10H), 7.64-7.80 (m, 6H), 7.84-7.89 (m, 2H) MS APCI, m/z=391 (M+1). LC/MS 2.53 min., Method A.

d. (3S,7S)-3-amino-1-(2-methoxyethyl)-7-phenyl-13,4,7-tetrahydro-2H-azepin-2-one (6d) and (3R,7S)-3-amino-1-(2-methoxyethyl)-7-phenyl-1,3,4,7-tetrahydro-2H-azepin-2-one (6e)

To 2-[(7S)-1-(2-methoxyethyl)-2-oxo-7-phenyl-2,3,4,7-tetrahydro-1H-azepin-3-yl]-1H-isoindole-1,3(2H)-dione (6c) (420 mg) dissolved in MeOH (10 mL) was added hydrazine hydrate (0.1 mL) and the mixture was stirred overnight at RT. A white precipitate formed in solution. The reaction mixture was diluted with ether and the precipitate was filtered and washed with ether. The etheral filtrate was concentrated and the resulting residue dissolved in DCM. The DCM solution was washed with H₂O and brine, dried (Na₂SO₄) and concentrated. The diastereomeric mixture was separated via preparative plate chromatography (eluent 10% MeOH in 1:1 ether/DCM) to give (3R,7S)-3-amino-1-(2-methoxyethyl)-7-phenyl-1,3,4,7-tetrahydro-2H-azepin-2-one (6e) and (3S,7S)-3-amino-1-(2-methoxyethyl)-7-phenyl-1,3,4,7-tetrahydro-2H-azepin-2-one (6d) (combined yield of 67%).

6e
¹H NMR (300 MHz, CDCl₃) δ 2.12-2.35 (m, 2H), 3.33 (s, 3H), 3.39-3.66 (m, 4H), 4.30 (dt, 1H), 5.20 (bd, 1H), 5.91-5.97 (m, 1H), 6.15-6.22 (m, 1H), 7.26-7.36 (m, 5H). MS APCI, m/z=261 (M+1). LC/MS 1.02 min., Method A.

6d $^1$H NMR (300 MHz, CDCl$_3$) δ 2.20-2.31 (m, 1H), 2.57-2.65 (m, 1H), 3.00-3.27 (m, 3H), 3.15 (s, 3H), 3.47-3.57 (m, 1H), 4.49-4.55 (m, 1H), 5.80-5.85 (m, 2H), 6.19-6.24 (m, 1H), 7.35-7.45 (m, 5H). MS APCI, m/z=261 (M+1). LC/MS 1.12 min., Method A.

Example 7

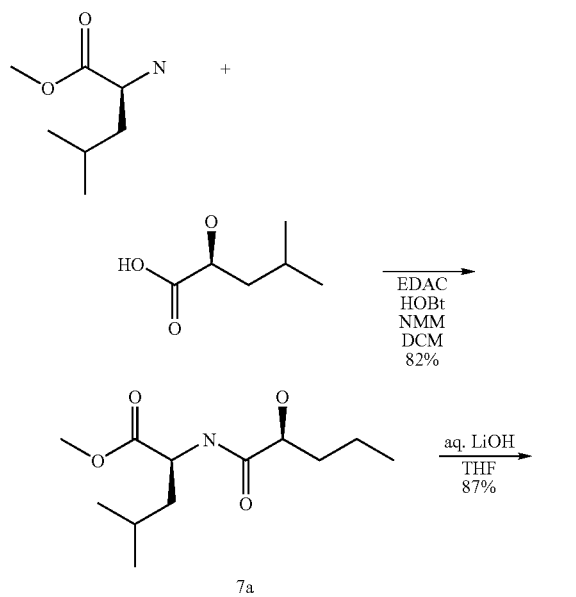

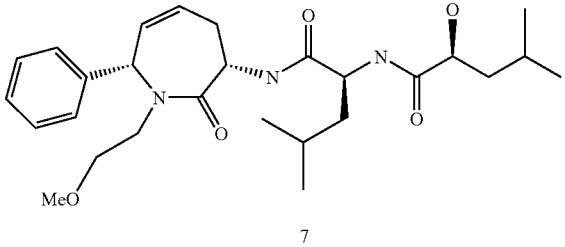

7

Example 7

N$^2$-[(2S)-2-hydroxy-4-methylpentanoyl]-N$^1$-[(3S,7S)-1-(2-methoxyethyl)-2-oxo-7-phenyl-2,3,4,7-tetrahydro-1H-azepin-3-yl]-L-leucinamide (7)

Utilizing (3S,7S)-3-amino-1-(2-methoxyethyl)-7-phenyl-1,3,4,7-tetrahydro-2H-azepin-2-one (6d) and N-[(2S)-2-hydroxy-4-methylpentanoyl]-L-leucine (7b), the title compound was synthesized using the same procedure as that described for Example 6.

$^1$H NMR (300 MHz, CDCl$_3$) δ 0.95-0.98 (m, 12H), 1.52-1.69 (m, 4H), 1.83-1.88 (m, 1H), 2.18-2.29 (m, 1H), 2.81-2.96 (m, 2H), 3.02-3.09 (m, 1H), 3.14 (s, 3H), 3.16-3.22 (m, 1H), 3.54-3.63 (m, 1H), 4.18-4.24 (m, 1H), 4.48-4.55 (m, 1H), 5.50-5.58 (m, 1H), 5.83-5.84 (m, 1H), 5.90 (bs, 1H), 6.18-6.23 (m, 1H), 6.94 (bd, 1H), 7.31-7.43 (m, 5H). MS APCI, m/z=488(M+1). LC/MS 2.47 min., Method A.

N-[(2S)-2-hydroxy-4-methylpentanoyl]-L-leucine (7b) was prepared in the following manner:

a. methyl N-[(2S)-2-hydroxy-4-methylpentanoyl]-L-leucinate (7a)

To a solution of L-leucine methyl ester hydrochloride (1.97 g) dissolved in DCM (32 mL) was added NMM (1.9 mL) and the mixture was stirred for 5 minutes before being cooled to 0° C. HOBt (4.0 g), EDAC (3.8 g) and L-α-hydroxyisocaproic acid (1.35 g) were then added sequentially to the reaction mixture. After 30 minutes at 0° C., the reaction was allowed to warm to room temperature and continued stirring overnight. The reaction mixture was concentrated and the resulting crude product was dissolved in EtOAc and washed 2×1.2N HCl, 2× saturated NaHCO$_3$, brine, dried (MgSO$_4$) and concentrated to yield the desired product (2.32 g, 82%). $^1$H NMR (300 MHz, CDCl$_3$) δ 0.93-0.96 (m, 12H), 1.50-1.67 (m, 5H), 1.82-1.93 (m, 1H), 3.73 (s, 3H), 3.83 (bs, 1H), 4.11-4.18 (m, 1H), 4.57-4.64 (m, 1H), 7.07 (d, 1H).

b. N-[(2S)-2-hydroxy-4-methylpentanoyl]-L-leucine (7b)

To a solution of methyl N-[(2S)-2-hydroxy-4-methylpentanoyl]-L-leucinate (7a) (2.13 g) dissolved in THF (21 mL) was added an aqueous 2.3 M LiOH solution (17 mL). The reaction mixture was stirred for 2 hours at room temperature, diluted with 1.2 N HCl (100 mL) and extracted with EtOAc. The organic layer was washed with brine and concentrated to give the desired product (1.75 g, 87%). $^1$H NMR (300 MHz, CDCl$_3$) δ 0.92-0.96 (m, 12H), 1.50-1.71 (m, 5H), 1.82-1.90 (m, 1H), 4.17-4.22 (m, 1H), 4.50-4.57 (m, 1H), 7.26 (d, 1H).

Example 8A and 8
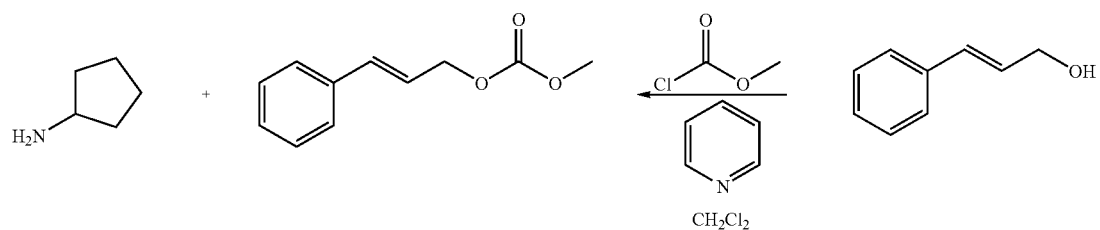
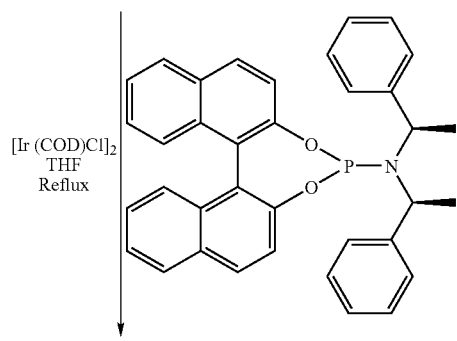
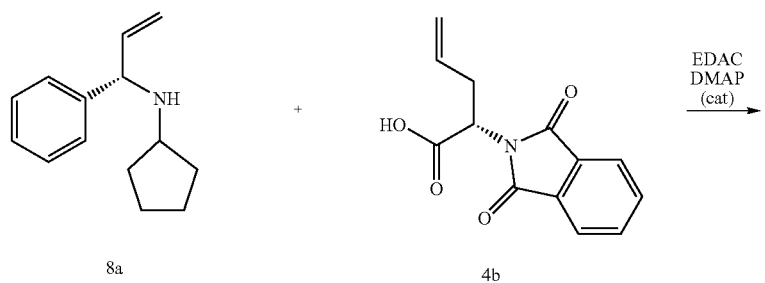
8a + 4b
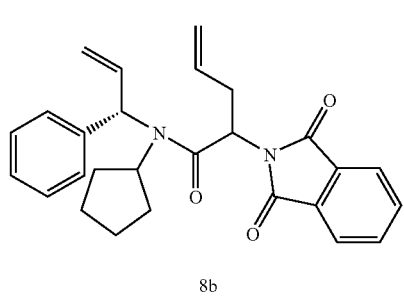
8b
Grubbs catalyst-
2nd generation (5 mol %)
Toluene, 80° C.

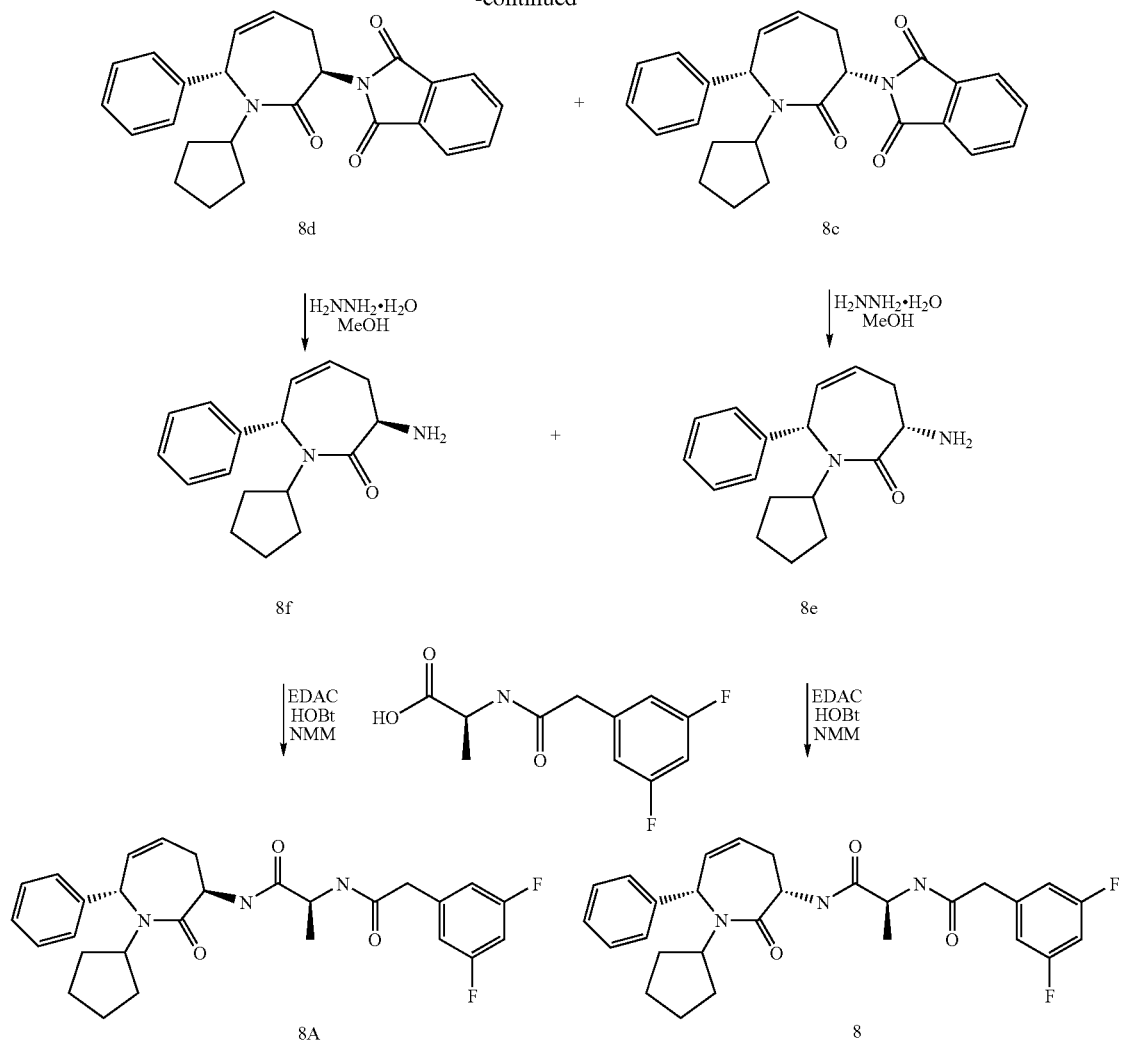

Example 8A

N¹-[(3R,7S)-1-cyclopentyl-2-oxo-7-phenyl-2,3,4,7-tetrahydro-1H-azepin-3-yl]-N²-[(3,5-difluorophenyl)acetyl]-L-alaninamide To a solution of (3R,7S)-3-amino-1-cyclopentyl-7-phenyl-1,3,4,7-tetrahydro-2H-azepin-2-one (8f) (65 mg) in DCM (4 ml) at RT under $N_2$ was added N-[(3,5-difluorophenyl)acetyl]-L-alanine (59 mg), HOBt (65 mg), EDAC.HCl (69 mg), and N-methylmorpholine (24 mg). The reaction was stirred at RT overnight, then diluted with DCM (10 ml) and washed with 1N HCl, 1N $K_2CO_3$, dried ($Na_2SO_4$), filtered and evaporated. The crude product was purified by flash chromatography (2% MeOH/DCM) to afford the title compound as an off white solid (60 mg, 50%). ¹H NMR (300 MHz, $CDCl_3$) δ 1.28 (d, 3H, J=7 Hz), 1.37-1.70 (m, 6H), 1.94-2.16 (m, 3H), 2.50-2.60 (m, 1H), 3.48 (s, 2H), 4.36-4.55 (m, 2H), 4.96 (d, 1H, J=8 Hz), 5.20 (tt, 1H, J=9 Hz, J=9 Hz), 5.87-5.94 (m, 1H), 6.18-6.33 (m, 2H), 6.67-6.80 (m, 3H), 7.00 (d, 1H, J=6 Hz), 7.25-7.38 (m, 5H). MS APCI, m/z=496 (M+1), LC/MS, 2.54 min.

Example 8

N¹-[(3S,7S)-1-cyclopentyl-2-oxo-7-phenyl-2,3,4,7-tetrahydro-1H-azepin-3-yl]-N²-[(3,5-difluorophenyl)acetyl]-L-alaninamide To a solution of crude (3S,7S)-3-amino-1-cyclopentyl-7-phenyl-1,3,4,7-tetrahydro-2H-azepin-2-one (8d) (40 mg) in DCM (3 ml) at RT under $N_2$ was added N-[(3,5-difluorophenyl)acetyl]-L-alanine (36 mg), HOBt (40 mg), EDAC.HCl (42 mg), and N-methylmorpholine (15 mg). The reaction was stirred at RT overnight., then diluted with DCM (10 ml) and washed with 1N HCl, 1N $K_2CO_3$, dried ($Na_2SO_4$), filtered and evaporated. The crude product was purified by flash chromatography (2% MeOH/DCM) to afford the title compound as a 70:30 mixture with N¹-[(3R,7R)-1-cyclopentyl-2-oxo-7-phenyl-2,3,4,7-tetrahydro-1H-azepin-3-yl]-N²-[(3,5-difluorophenyl)acetyl]-L-alaninamide as an off white solid (55 mg, 75%). ¹H NMR (300 MHz, $CDCl_3$) δ 1.17-2.21 (m, 12H), 2.79-2.87 (m, 1H), 3.55 (s, 2H), 5.44-5.52 (m, 1H), 5.80-5.84 (m, 1H), 5.90-5.93 (s, 1H), 6.26-6.35 (m, 2H), 6.69-6.86 (m, 3H), 7.19-7.46-(m, 6H). MS APCI, m/z=496 (M+1), LC/MS, 2.65 min.

The two starting amines, (3R,7S)-3-amino-1-cyclopentyl-7-phenyl-1,3,4,7-tetrahydro-2H-azepin-2-one (8f) and (3S,7S)-3-amino-1-cyclopentyl-7-phenyl-1,3,4,7-tetrahydro-2H-azepin-2-one (8e) were prepared in the following manor:

a. N-[(1S)-1-phenylprop-2-en-1-yl]cyclopentan-amine (8a)

To a solution of Methyl (2E)-3-phenylprop-2-en-1-yl carbonate (384 mg) in THF (5 ml), was added N,N-bis[(1S)-1-phenylethyl]dinaphtho[1,2-f:2',1'-d][1,3,2]dioxaphosphepin-4-amine (108 mg), and chloro(1,5-cyclooctadiene)iridium(I) dimer (27 mg) at RT under $N_2$. The mixture was heated at reflux overnight. Evaporated material then redissoled in a 50:50 mixture of EtOH:THF. To this solution was added macro porous p-toluenesulfonic acid resin (6 g) and the mixture was gently agitated for 3 h. At this time the resin was washed completely with THF, THF:EtOH and EtOH. To a suspension of the resin in MeOH (75 ml) was added 7 N $NH_3$.MeOH (75 ml). This mixture was gently agitated for 2 hours and filered, washing with MeOH, THF, THF:MeOH, and DCM. Evaporating this filtrate left the title compound as a yellow oil (360 mg, 89%). $^1$H NMR (300 MHz, $CDCl_3$) δ 1.25-1.87 (m, 9H), 2.98-3.07 (m, 1H), 4.24 (d, 1H, J=7 Hz), 5.06-5.21 (m, 2H), 5.87-5.99 (m, 1H), 7.20-7.34 (m, 5H). MS APCI, m/z=202 (M+1), LC/MS, 1.35 min.

The benzyl amide derivative of this amine was used to analyze the stereo purity.

N-benzyl-N-[(1S)-1-phenylprop-2-en-1-yl]cyclopentanamine

To a solution of N-[(1S)-1-phenylprop-2-en-1-yl]cyclopentanamine (24 mg) and diisopropylamine (18 mg) in DCM (2.5 ml) at RT under $N_2$ was added benzoyl chloride (20 mg). This mixture was stirred for 1 h. The reaction was evaporated and purified by flash chromatography (2% EtOAc/hexane) to afford the title compound (15 mg, 44%) as a pale oil. $^1$H NMR (300 MHz, $CDCl_3$) δ 1.22-2.27 (m, 8H), 3.57 (bs, 1H), 5.28-5.60 (m, 3H), 6.23 (bs, 1H), 7.00-7.71 (m, 10H). MS APCI, m/z=306 (M+1), LC/MS, 2.83 min. Chiral HPLC was used to determine ee % by comparing this sample to a known sample of the racemic compound N-benzyl-N-(1-phenylprop-2-en-1-yl)cyclopentanamine. 14.99 min (97.89%) and 17.52 min (2.11%) or 96% ee. Chiral HPLC method: Chiral Technologies 10 μm Chiralpak AD column 4.6 mm×250 mm. Solvents: A=IPA, B=Hexane. Isocratic Method 7% A/B over 30 minutes at 0.6 ml/mn.

b. (2S)-N-cyclopentyl-2-(1,3-dioxo-1,3-dihydro-2H-isoindol-2-yl)-N-[(1S)-1-phenylprop-2-en-1-yl]pentenamide (8b)

To a solution of (2S)-2-(1,3-dioxo-1,3-dihydro-2H-isoindol-2-yl)pent-4-enoic acid (361 mg), EDAC.HCl (408 mg), and dimethyl aminopyridine (8 mg) in DCM (4 ml) at −20° C. under $N_2$ was added a solution of N-[(1S)-1-phenylprop-2-en-1-yl]cyclopentanamine in DCM (3 ml). The mixture was allowed to stir at −20° C. for 1 hr then RT overnight. The next day the reaction was diluted with DCM and extracted with 0.1 N HCl. The aqueous layer was back extracted with DCM (×2). All organics were combined, dried ($Na_2SO_4$), filtered and evaporated. The resulting residue was purified by column chromatography (10% EtOAc/Hexane) to afford a mixture (85:15) (SS:RS) of the title compound and it's diasteromer (2R)-N-cyclopentyl-2-(1,3-dioxo-1,3-dihydro-2H-isoindol-2-yl)-N-[(1S)-1-phenylprop-2-en-1-yl]pent-4-enamide (249 mg) as determined by NMR. $^1$H NMR (300 MHz, d6-DMSO at 110° C.) δ 1.10-2.12 (m, H9), 2.38-3.15 (m, 2H), 4.88-5.21 (m, 4H), 5.30-5.45 (m, 3H), 5.70-5.90 (m, 1H), 6.00-6.18 (m, 1H), 6.21-6.38 (m, 0.17H), 6.95-7.12 (m, 1H), 7.19-7.41 (m, 5H), 7.18-7.95 (m, 4H). MS APCI, m/z=429 (M+1), LC/MS, 3.04 min.

c. 2-[(3R,7S)-1-cyclopentyl-2-oxo-7-phenyl-2,3,4,7-tetrahydro-1H-azepin-3-yl]-1H-isoindole-1,3(2H)-dione (8d) and 2-[(3S,7S)-1-cyclopentyl-2-oxo-7-phenyl-2,3,4,7-tetrahydro-1H-azepin-3-yl]-1H-isoindole-1,3(2H)-dione (8c)

To a solution of N-cyclopentyl-2-(1,3-dioxo-1,3-dihydro-2H-isoindol-2-yl)-N-[(1S)-1-phenylprop-2-en-1-yl]pent-4-enamide (330 mg) dissolved in Toluene (30 mL) at 80° C. under $N_2$ was added Grubbs catalyst (2nd generation) (33 mg) and the reaction mixture was stirred at 80° C. for 35 minutes, cooled to RT and concentrated in vacuo. The crude product was directly purified via flash chromatography (gradient—10%, 15% EtOAc/hexanes) to give the title compounds, 2-[(3R,7S)-1-cyclopentyl-2-oxo-7-phenyl-2,3,4,7-tetrahydro-1H-azepin-3-yl]-1H-isoindole-1,3(2H)-dione (8d) (182 mg) and 2-[(3S,7S)-1-cyclopentyl-2-oxo-7-phenyl-2,3,4,7-tetrahydro-1H-azepin-3-yl]-1H-isoindole-1,3(2H)-dione (8c) (95 mg, combined yield of 90%). (8d) $^1$H NMR (300 MHz, $CDCl_3$) δ 1.44-1.70 (m, 6H), 1.85-2.04 (m, 3H), 2.36-2.43 (m, 1H), 3.69-3.81 (m, 1H), 5.02-5.15 (m, 2H), 5.18-5.30 (m, 1H), 5.98-6.05 (m, 1H), 6.35-6.42 (m, 1H), 7.19-7.52 (m, 5H), 7.64-7.87 (m, 4H). MS APCI, m/z=401 (M+1), LC/MS, 2.73 min. (8c) $^1$H NMR (300 MHz, $CDCl_3$) δ 1.14-1.88 (m, 9H), 2.25-2.32 (m, 1H), 3.37-3.48 (m, 1H), 4.01-4.11 (m, 1H), 5.30 (dd, 1H, J=13 Hz, J=4 Hz), 5.52 (d, 1H, J=7 Hz), 6.04-6.11 (m, 1H), 6.43-6.50 (m, 1H), 7.29-7.55 (m, 5H), 7.69-7.90 (m, 4H). MS APCI, m/z=401 (M+1), LC/MS, 2.80.

d. (3R,7S)-3-amino-1-cyclopentyl-7-phenyl-1,3,4,7-tetrahydro-2H-azepin-2-one (8f)

To a solution of 2-[(3R,7S)-1-cyclopentyl-2-oxo-7-phenyl-2,3,4,7-tetrahydro-1H-azepin-3-yl]-1H-isoindole-1,3(2H)-dione (100 mg) in MeOH (4 ml), was added hydrazine hydrate (27 mg) at RT under $N_2$. The mixture was allowed to stir overnight at RT. The reaction was evaporated and the residue was taken up in DCM and washed with water. The organics were dried ($Na_2SO_4$), filtered and evacuated to afford the title compound (65 mg, 96% crude yield) yellow oil. $^1$H NMR (300 MHz, $CDCl_3$) δ 1.38-2.31 (m, 1H), 3.46-3.56 (m, 1H), 4.91 (d, 1H, J=8 Hz), 5.24-5.34 (m, 1H), 5.88-5.96 (m, 1H), 6.25-6.33 (m, 1H), 7.21-7.36 (m, 5H).

e. (3S,7S)-3-amino-1-cyclopentyl-7-phenyl-1,3,4,7-tetrahydro-2H-azepin-2-one (8e)

To a solution of 2-[(3S,7S)-1-cyclopentyl-2-oxo-7-phenyl-2,3,4,7-tetrahydro-1H-azepin-3-yl]-1H-isoindole-1,3(2H)-dione (75 mg) in MeOH (3 ml), was added hydrazine hydrate (21 mg) at RT under $N_2$. The mixture was allowed to stir overnight at RT. The reaction was evaporated and the residue was taken up in DCM and washed with water. The organics were dried ($Na_2SO_4$), filtered and evacuated to afford the title compound (40 mg, 79% crude yield) as a crude, yellow oil. This crude oil was not characterized or purified further before taken on to the coupling step.

Example 9A and 9
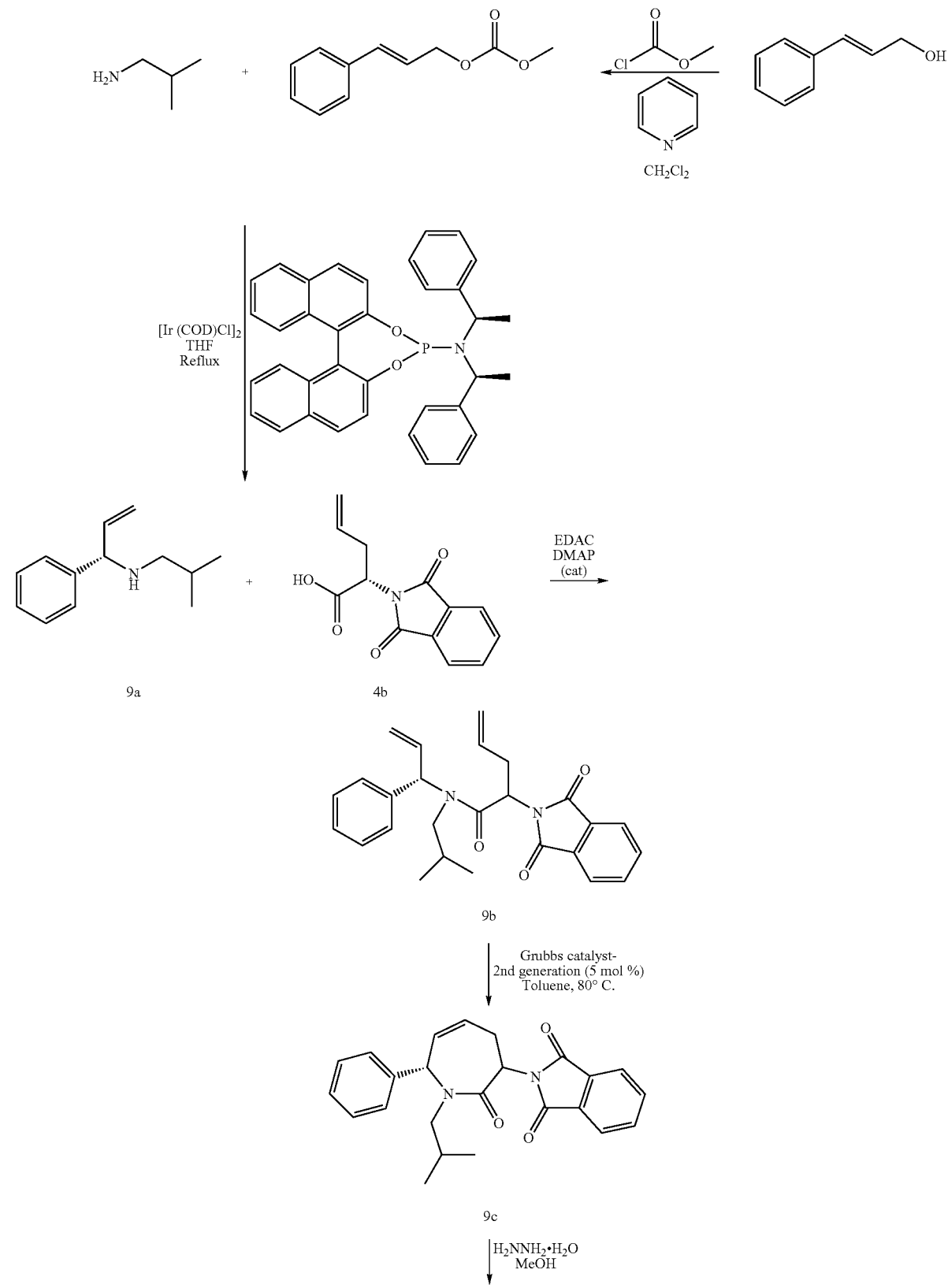

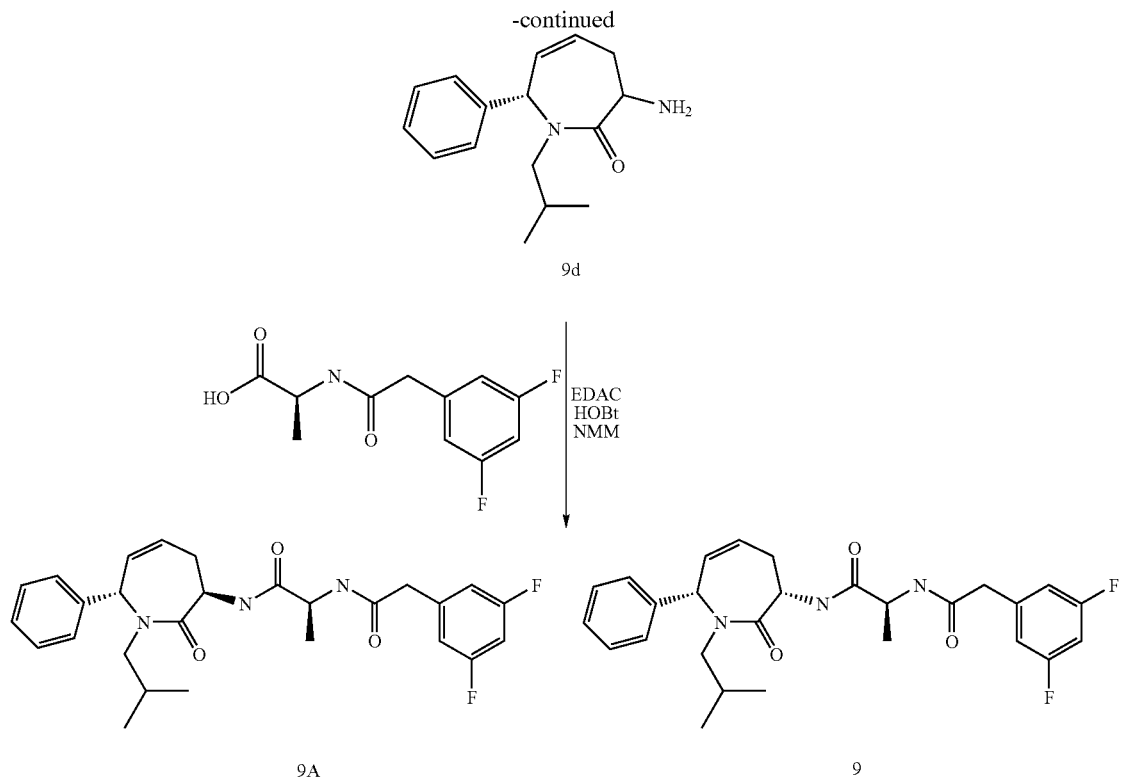

Example 9A

N¹-[(3R,7S)-1-isobutyl-2-oxo-7-phenyl-2,3,4,7-tetrahydro-1H-azepin-3-yl]-N²-[(3,5-difluorophenyl)acetyl]-L-alaninamide and Example 9. N¹-[(3S,7S)-1-isobutyl-2-oxo-7-phenyl-2,3,47-tetrahydro-1H-azepin-3-yl]-N²-[(3,5-difluorophenyl)acetyl]-L-alaninamide To a solution of a mixture of diastereomers (3RS,7S)-3-amino-1-isobutyl-7-phenyl-1,3,4,7-tetrahydro-2H-azepin-2-one (9d) (150 mg) in DCM (10 ml) at 0° C. under $N_2$ was added N-[(3,5-difluorophenyl)acetyl]-L-alanine (141 mg), HOBt (157 mg), EDAC.HCl (166 mg), and N-methylmorpholine (59 mg). The reaction was stirred at RT overnight, then diluted with DCM (10 ml) and washed with 0.1N HCl, 1N $K_2CO_3$, dried $Na_2SO_4$), filtered and evaporated. The crude product was purified by flash chromatography (2% MeOH/DCM) to afford a mixture of diasteromers (280 mg). The diasteromers were seperated by SFC chiral chromatagraphy. The method employed a 21×250 mm ChiralPak AD-H column using an isocratic elution of 25% Isopropanol in carbon dioxide monitored @ 220 nm. 12 injections of 23 mg each of the crude mixture were made in each run, with each run lasting 8 minutes. The title compounds were isolated as white solids (9A, 100 mg and 9, 92 mg, 68%). 9A ¹H NMR (300 MHz, CDCl₃) δ 0.93 (d, 3H, J=6.6 Hz), 0.99 (d, 3H, J=6.9 Hz), 1.29 (d, 3H, J=6.9 Hz), 1.92-2.21 (m, 2H), 2.60-2.67 (m, 1H), 2.77-2.83 (m, 1H), 3.47 (s, 2H), 4.25-4.52 (m, 3H), 5.05 (d, 1H, J=7.5 Hz), 5.95-6.00 (m, 1H), 6.16-6.22 (m, 2H), 6.66-6.82 (m, 3H), 7.04 (d, 1H), 7.25-7.39 (m, 5H). MS APCI, m/z=484 (M+1), LC/MS, 2.65 min. 9 ¹H NMR (300 MHz, CDCl₃) δ 0.61 (d, 3H, J=6.6 Hz), 0.68 (d, 3H, J=6.6 Hz), 1.41 (d, 3H, J=6.9 Hz), 2.20-2.43 (m, 2H), 2.81-2.90 (m, 1H), 3.34-3.42 (m, 1H), 3.55 (s, 2H), 4.45-4.55 (m, 1H), 5.50-5.58 (m, 1H), 5.82-5.91 (m, 2H), 6.24-6.30 (m, 2H), 6.68-6.91 (m, 3H), 7.41 (s, 5H). MS APCI, m/z=484 (M+1), LC/MS, 2.69 min.

The starting amine mixture (9d), (3RS,7S)-3-amino-1-isobutyl-7-phenyl-1,3,4,7-tetrahydro-2H-azepin-2-one was prepared in the following manor:

a. (1S)-N-isobutyl-1-phenylprop-2-en-1-amine (9a)

To a solution of Methyl (2E)-3-phenylprop-2-en-1-yl carbonate (1.5 g) in THF (25 ml), was added N,N-bis[(1S)-1-phenylethyl]dinaphtho[1,2-f:2',1'-d][1,3,2]dioxaphosphepin-4-amine (420 mg), and chloro(1,5-cyclooctadiene)iridium(I) dimer (105 mg) at RT under $N_2$. The mixture was heated at reflux overnight. Evaporated material then redissoled in a 50:50 mixture of EtOH:THF. To this solution was added macro porous p-toluenesulfonic acid resin (10 g) and the mixture was gently agitated for 3 h. At this time the resin was washed completely with THF, THF:EtOH and EtOH. To a suspension of the resin in MeOH (75 ml) was added 7 N $NH_3$.MeOH (75 ml). This mixture was gently agitated for 2 hours and filered, washing with MeOH, THF, THF:MeOH, and DCM. Evaporating this filtrate left a yellow oil (1.2 g). This oil was then distilled on a kuglerohr vacumme distilation aparatus. This left the title compound as a clear oil. (830 mg, 53%). ¹H NMR (300 MHz, CDCl₃) δ 0.90 (d, 6H, J=6.6 Hz), 1.64-1.81 (m, 1H), 2.18-2.45 (m, 2H), 4.15 (d, 1H, J=6.9 Hz), 5.06-5.22 (m, 2H), 5.85-5.97 (m, 1H), 7.20-7.41 (m, 5H).

The benzyl amide derivative of this amine was used to analyze the stereo purity.

N-isobutyl-N-[(1S)-1-phenylprop-2-en-1-yl]benzamide

To a solution of (1S)-N-isobutyl-1-phenylprop-2-en-1-amine (9a) (25 mg) and diisopropylamine (19 mg) in DCM (2.5 ml) at RT under N₂ was added benzoyl chloride (21 mg). This mixture was stirred for 1 h. The reaction was evaporated and purified by flash chromatography (2% EtOAc/hexane) to afford the title compound (15 mg, 44%) as a pale oil. ¹H NMR (300 MHz, CDCl₃) δ 0.70 (d, 6H, J=6.6 Hz), 0.81 (bs, 3H), 1.75 (bs, 1H), 2.99-3.06 (m, 1H), 3.25-3.32 (m, 1H), 5.20-5.28 (m, 1H), 5.41 (d, 1H, J=9 Hz), 6.16 (bs, 1H), 7.25-7.46 (m, 5H). MS APCI, m/z=294 (M+1), LC/MS, 2.78 min. Chiral SFC was used to determine ee % by comparing this sample to a known sample of the racemic compound N-isobutyl-N-[(1-phenylprop-2-en-1-yl]benzamide 2.128 min (2.92%) and 2.639 min (97.07%) or 94% ee. Chiral SFC method: 5 µm Chiralpak AS-H column 4.6 mm×250 mm. Isocratic method 10% MeOH in carbon dioxide @ 2.20 ml/mn over 4 minutes.

b. 2-(1,3-dioxo-1,3-dihydro-2H-isoindol-2-yl)-N-isobutyl-N-[(1S)-1-phenylprop-2-en-1-yl]pent-4-enamide (9b)

To a solution of (2S)-2-(1,3-dioxo-1,3-dihydro-2H-isoindol-2-yl)pent-4-enoic acid (467 mg), EDAC.HCl (529 mg), and dimethyl aminopyridine (20 mg) in DCM (10 ml) at −20° C. under N₂ was added a solution of (1S)-N-isobutyl-1-phenylprop-2-en-1-amine in DCM (6 ml). The mixture was allowed to stir at −20° C. for 1 hr then RT overnight. The next day the reaction was diluted with DCM and extracted with 0.1 N HCl. The aqueous layer was back extracted with DCM (×2). All organics were combined, dried (Na₂SO₄), filtered and evaporated. The resulting residue was purified by column chromatography (20% EtAOc/Hexane) to afford the title compound as a mixture of diastereomers in the form of a clear oil (628 mg, 82%). ¹H NMR (300 MHz, d6-DMSO) δ 0.50-0.732 (m, 7H), 1.24-1.98 (m, 3H), 2.15-2.26 (m, 1H), 2.73-3.3 (m, 4H), 4.74-5.42 (m, 4H), 5.75-6.24 (m, 3H), 6.99-7.38 (m, 5H), 7.79-7.88 (m, 4H). MS APCI, m/z=417 (M+1), LC/MS, 2.93 min.

c. 2-[(3RS,7S)-1-isobutyl-2-oxo-7-phenyl-2,3,7-tetrahydro-1H-azepin-3-yl]-1H-isoindole-1,3(2H)-dione (9c)

To a solution of 2-(1,3-dioxo-1,3-dihydro-2H-isoindol-2-yl)-N-isobutyl-N-[(1S)-1-phenylprop-2-en-1-yl]pent-4-enamide (921 mg) dissolved in Toluene (90 mL) at 80° C. under N₂ was added Grubbs catalyst (2nd generation) (94 mg) and the reaction mixture was stirred at 80° C. for 45 minutes, cooled to RT and concentrated in vacuo. The crude product was directly purified via flash chromatography (gradient—10%, 15% EtOAc/hexanes) to give the title compound as a mixture of diasteromers (400 mg, 47%) in the form of a white solid. ¹H NMR (300 MHz, CDCl₃) δ 0.70 (d, 3H, J=6.6 Hz), 0.77 (d, 3H, J=6.6 Hz), 0.93-0.99 (m, 6H), 1.67-1.71(m, 1H), 2.00-2.39 (m, 1H), 2.42-2.44 (m, 2H), 6.68-2.75 (m, 1H), 2.92-2.99 (m, 1H), 3.07-3.14 (m, 1H), 3.65-3.74 (m, 2H), 4.21-4.29 (m, 1H), 5.05 (dd, 1H, J=3 Hz, 13.2 Hz), 5.13 (d, 1H, J=7.5 Hz), 5.76 (dd, 1H, J=3.7 Hz, 13.4 Hz), 5.71 (d, 1H, J=4.2 Hz), 6.05-6.12 (m, 2H), 6.28-6.36 (m, 2H), 7.25-7.48 (m, 5H), 7.63-7.88 (m, 4H). MS APCI, m/z=389 (M+1), LC/MS, 2.82 min.

d. (3RS,7S)-3-amino-1-isobutyl-7-phenyl-1,3,47-tetrahydro-2H-azepin-2-one (9d)

To a solution of the diasteremeric mixture, 2-[(3RS,7R)-1-isobutyl-2-oxo-7-phenyl-2,3,4,7-tetrahydro-1H-azepin-3-yl]-1H-isoindole-1,3(2H)-dione (9c) (360 mg) in MeOH (20 ml), was added hydrazine hydrate (97 mg) at RT under N₂. The mixture was allowed to stir overnight at RT. The reaction was evaporated and the residue was taken up in DCM and washed with water. The organics were dried (Na₂SO₄), filtered and evacuated to afford the title compound (152 mg, 64% crude yield) as a yellow oil.

¹H NMR (300 MHz, CDCl₃) δ 0.61-0.68 (m, 6H), 0.91-1.00 (m, 6H), 1.39-1.48 (m, 1H), 1.91-2.03 (m, 1H), 2.16-2.81 (m, 4H), 3.27-3.34 (m, 1H), 3.48-3.53 (m, 1H), 4.27-4.36 (m, 1H), 4.50-4.54 (m, 1H), 5.01 (d, 1H, J=7.8 Hz), 5.83-6.28 (m, 4H), 7.23-7.39 (m, 5H). MS APCI, m/z=259 (M+1), LC/MS, 1.67 and 1.78 min.

Example 10 and 10A

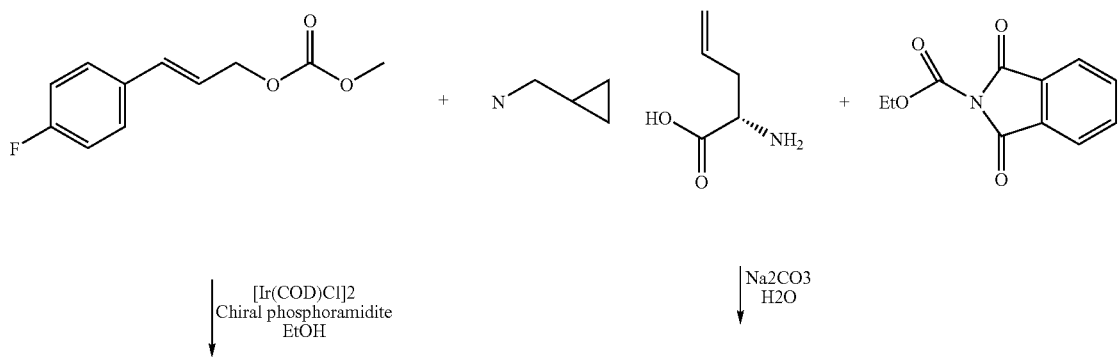

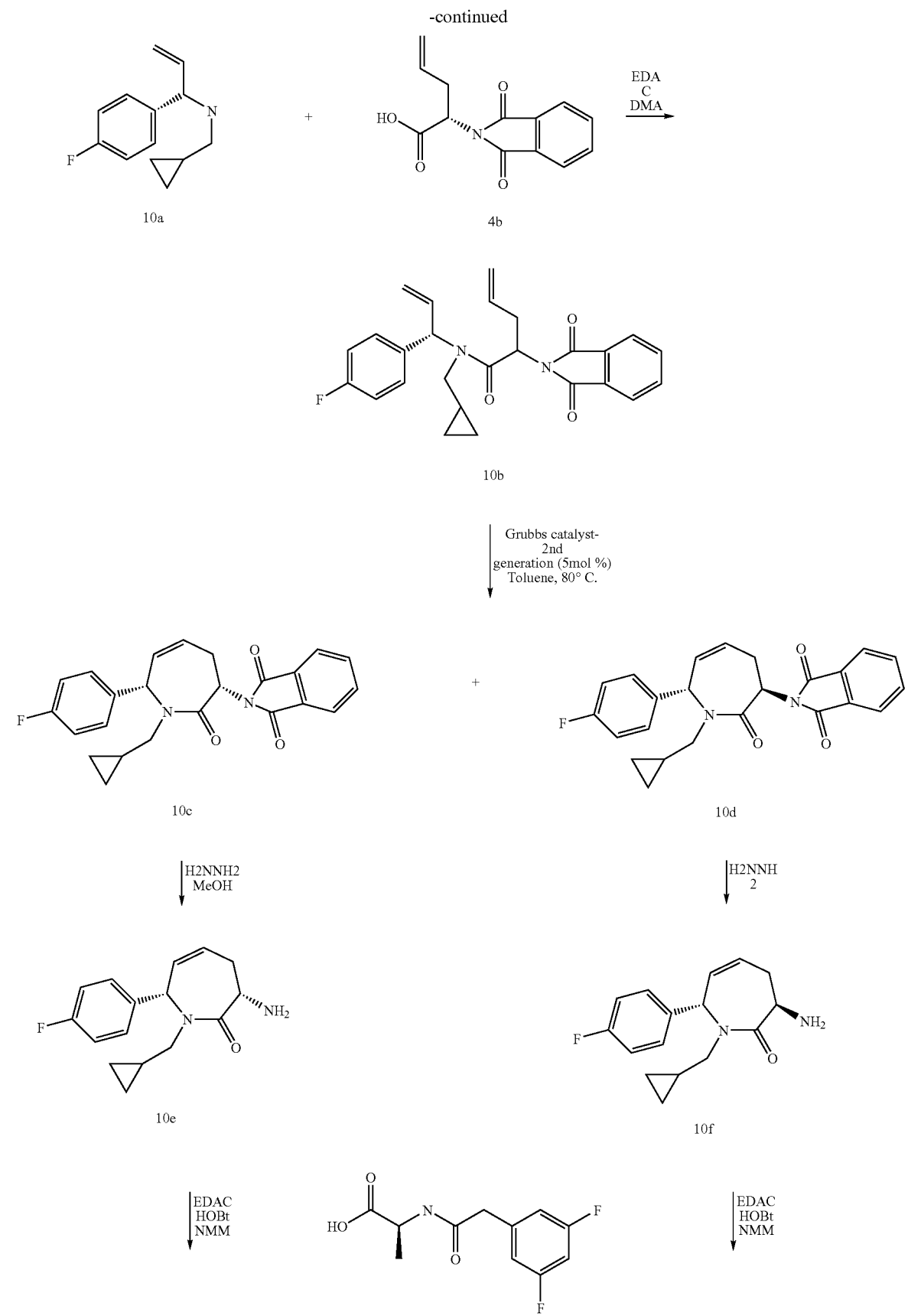

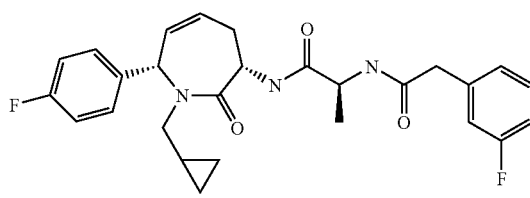

10

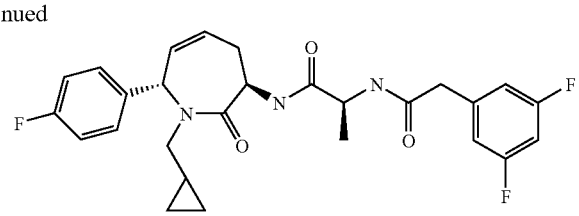

10A

Example 10

N¹-[(3S,7S)-1-(cyclopropylmethyl)-7-(4-fluorophenyl)-2-oxo-2,3,4,7-tetrahydro-1H-azepin-3-yl]-N²-[(3,5-difluorophenyl)acetyl]-L-alaninamide To a solution of (3S,7S)-3-amino-1-(cyclopylmethyl)-7-(4-fluorophenyl)-1,3,4,7-tetrahydro-2H-azepin-2-one (10e) (36 mg) in DCM (3 mL) at 0° C. under $N_2$ was added N-[(3,5-difluorophenyl)acetyl]-L-alanine (32 mg), HOBt-hydrate (44 mg), EDAC.HCl (38 mg) and N-methyl morpholine (21 mg). The reaction mixture was stirred 1 h at 0° C. and 3H at room temperature, then diluted with 30% Hexanes/EtOAc (100 mL). The organic phase was consecutively washed with $H_2O$, 0.2 N HCl, saturated $NaHCO_3$, and brine, dried ($Na_2SO_4$), filtered and evaporated. The crude product was purified by flash chromatography (2% MeOH/DCM) to afford the title compound as an off-white solid (59 mg, 96%). $^1$H NMR (300 MHz, $CDCl_3$) δ 0.39 (m, 2H), 0.56 (m, 2H), 1.22 (m, 1H), 1.31 (d, 3H), 1.71 (m, 1H), 2.02)m, 1H), 3.20 (d, 2H), 3.80 (s, 2H), 4.60-4.69 (m, 1H), 4.96 (m, 1H), 5.31 (m, 1H), 6.13 (bd, 1H), 6.48 (m, 1H), 6.84 (bd, 2H), 6.99-7.22 (m, 5H). MS APCI, m/z=500 (M+1). LC/MS 2.22 min., Method A.

Example 10A

N¹-[(3R,7S)-1-(cyclopropylmethyl)-7-(4-fluorophenyl)-2-oxo-2,3,4,7-tetrahydro-1H-azepin-3-yl]-N²-[(3,5-difluorophenyl)acetyl]-L-alaninamide Utilizing (3R,7S)-3-amino-1-(cyclopropylmethyl)-7-(4-flurophenyl)-1,3,4,7-tetrahydro-2H-azepin-2-one (10f), the title compound was synthesized using the same procedure as that described for Example 10. The crude product was purified by flash chromatography (2% MeOH/DCM) to afford the title compound as an off-white solid (72%). $^1$H NMR (300 MHz, $CDCl_3$) δ 0.39 (m, 2H), 0.56 (m, 2H), 1.22 (m, 1H), 1.31 (d, 3H), 1.71 (m, 1H), 2.02 (m, 1H), 3.20 (d, 2H), 3.80 (s, 2H), 4.60-4.69 (m, 1H), 4.96 (m, 1H), 5.31 (m, 1H), 6.13 (bd, 1H), 6.48 (m, 1H), 6.84 (bd, 2H), 6.99-7.22 (m, 5H). MS APCI, m/z=500 (M+1). LC/MS 2.16 min., Method A.

The stereoselective allylic amine (1S)-N-(cyclopropylmethyl)-1-(4-fluorophenyl)prop-2-en-1-amine (10) was prepared by Iridium Complex-Catalyzed allylic amination of allylic esters:

a. (1S)-N-(cyclopropylmethyl)-1-(4-fluorophenyl)prop-2-en-1-amine (10a)

A mixture of (2E)-3-(4-fluorophenyl)prop-2-en-1-yl methyl carbonate (420 mg), N,N-bis[(1S)-1-phenylethyl]dinaphtho[1,2-f:2',1'-d][1,3,2]dioxaphosphepin-4-amine (108 mg), [Ir(COD)Cl]2 (27 mg), cyclopropyl methyl amine (374 μL) and EtOH (5 mL) was stirred under refluxing EtOH for 6H under N2. The progress of the reaction was monitered by HPLC. At the end of the reaction, addition of co-solvent (20 ml EtOH and 20 ml THF) and MP-TsOH resin (6 g) and the mixture was allowed to stirred at RT with swilling every 15 mins for 2-3 hours. Filtered the resin and washed the resin with plenty of EtOH, THF, DCM. The resin was taken up in 3.5N NH3 in MeOH (20 mL) and let it stir for overnight. Filtered the resin and washed the resin excessively with EtOH, THF and DCM. Combined the filtrate and evaporated all the solvent. The crude product was purified by flash chromatography (10% EtOAc/Hexane) to afford the title compound as a viscous oil (350 mg, 88%). $^1$H NMR (300 MHz, $CDCl_3$) revealed branched/linear ratio (9:1) 0.27 (m, 2H), 0.47 (m, 2H), 1.10 (m, 1H), 2.40 (m, 2H), 4.51(m, 1H), 5.25-5.39 (m, 3H), 7.02-7.22 (m, 4H). MS APCI, m/z=206 (M+1). LC/MS 0.85 min., Method A. 94% ee was determined by NMR in the presence of TFAE-$d_{11}$ The starting amines (10e), and (10f) were prepared using the same procedure as described for amine 5e:

b. 2-N-(cyclopropylmethyl)-2-(1,3-dioxo-1,3-dihydro-2H-isoindol-2-yl)-[(1S)-1-(4-fluorophenyl)prop-2-en-1-yl)pent-4-enamide (10b)

The crude product was purified via flash chromatography (20% EtOAc/hexanes) to give the desired product as a viscous oil (60%). NMR studies revealed that there are two diastereomers presented at the ratio 3:1 (cis: trans). $^1$H NMR (300 MHz, $CDCl_3$) δ 0.39 (m, 2H), 0.56 (m, 2H), 1.18 (m, 1H), 2.78 (m, 2H-diastereomer/rotamer mixture), 3.03 (m, 2H), 4.83 (m, 1H), 5.38-5.75 (m, 5H), 6.80 (m, 1H), 6.89-7.23 (m, 4H), 7.77-7.93 (m, 4H). MS APCI, m/z=433 (M+1). LC/MS 3.08 min., Method A.

c. 2-[(3S,7S)-1-(cyclopropylmethyl)-7-(4-fluorophenyl)-2-oxo-2,4,7-tetrahydro-1H-azepin-3-yl]-1H-isoindole-1,3(2H)-dione (10d)

The crude product was directly purified via flash chromatography (gradient—5%, 10%, 15% and 20% EtOAc/hexanes) to give the title compound (2c) (49%) and 2-[(3R,7S)-1-(cyclopropylmethyl)-7-(4-fluorophenyl)-2-oxo-2,3,4,7-tetrahydro-1H-azepin-3-yl]-1H-isoindole-1,3(2H)-dione (10d) (9%) (combined yield of 58%).

10c $^1$H NMR (300 MHz, CDCl$_3$) δ 0.39 (m, 2H), 0.56 (m, 2H), 1.24 (m, 1H), 1.48-1.80 (m, 2H), 3.03 (m, 2H), 3.20 (m, 2H), 4.54 (m, 2H), 4.94 (d, 1H), 5.94 (m, 1H), 6.13 (m, 1H), 6.89-7.93 (m, 8H). MS APCI, m/z=405 (M+1). LC/MS 2.88 min., Method A.

10d $^1$H NMR (300 MHz, CDCl$_3$) δ 0.39 (m, 2H), 0.56 (m, 2H), 1.24 (m, 1H), 1.48-1.80 (m, 2H), 3.03 (m, 2H), 3.20 (m, 2H), 4.56 (m, 2H), 4.94 (d, 1H), 5.94 (m, 1H), 6.13 (m, 1H), 6.89-7.90 (m, 8H). MS APCI, m/z=405 (M+1). LC/MS 2.87 min., Method A.

d. (3S,7S)-3-amino-1-(cyclopropylmethyl)-7-(4-flurophenyl)-1,3,4,7-tetrahydro-2H-azepin-2-one (10e)

The title compound was isolated as a viscous oil (80%). $^1$H NMR (300 MHz, CDCl$_3$) δ 0.39 (m, 2H), 0.56 (m, 2H), 1.24 (m, 1H), 1.48-1.80 (m, 2H), 3.13-3.31 (m, 2H), 4.34 (m, 1H), 5.16 (d, 1H), 6.09 (m, 1H), 6.14 (m, 1H), 6.89-7.93 (m, 4H). MS APCI, m/z=275 (M+1). LC/MS 1.85 min., Method A.

e. (3R,7S)-3-amino-1-(cyclopropylmethyl)-7-(4-flurophenyl)-1,3,4,7-tetrahydro-2H-azepin-2-one (10f)

The title compound was isolated as a viscous oil (80%). $^1$H NMR (300 MHz, CDCl$_3$) δ 0.39 (m, 2H), 0.56 (m, 2H), 1.24 (m, 1H), 1.48-1.80 (m, 2H), 3.13-3.31 (m, 2H), 4.34 (m, 1H), 5.16 (d, 1H), 6.09 (m, 1H), 6.14 (m, 1H), 6.89-7.93 (m, 4H). MS APCI, m/z=275 (M+1). LC/MS 1.83 min., Method A.

Example 11 and 11A

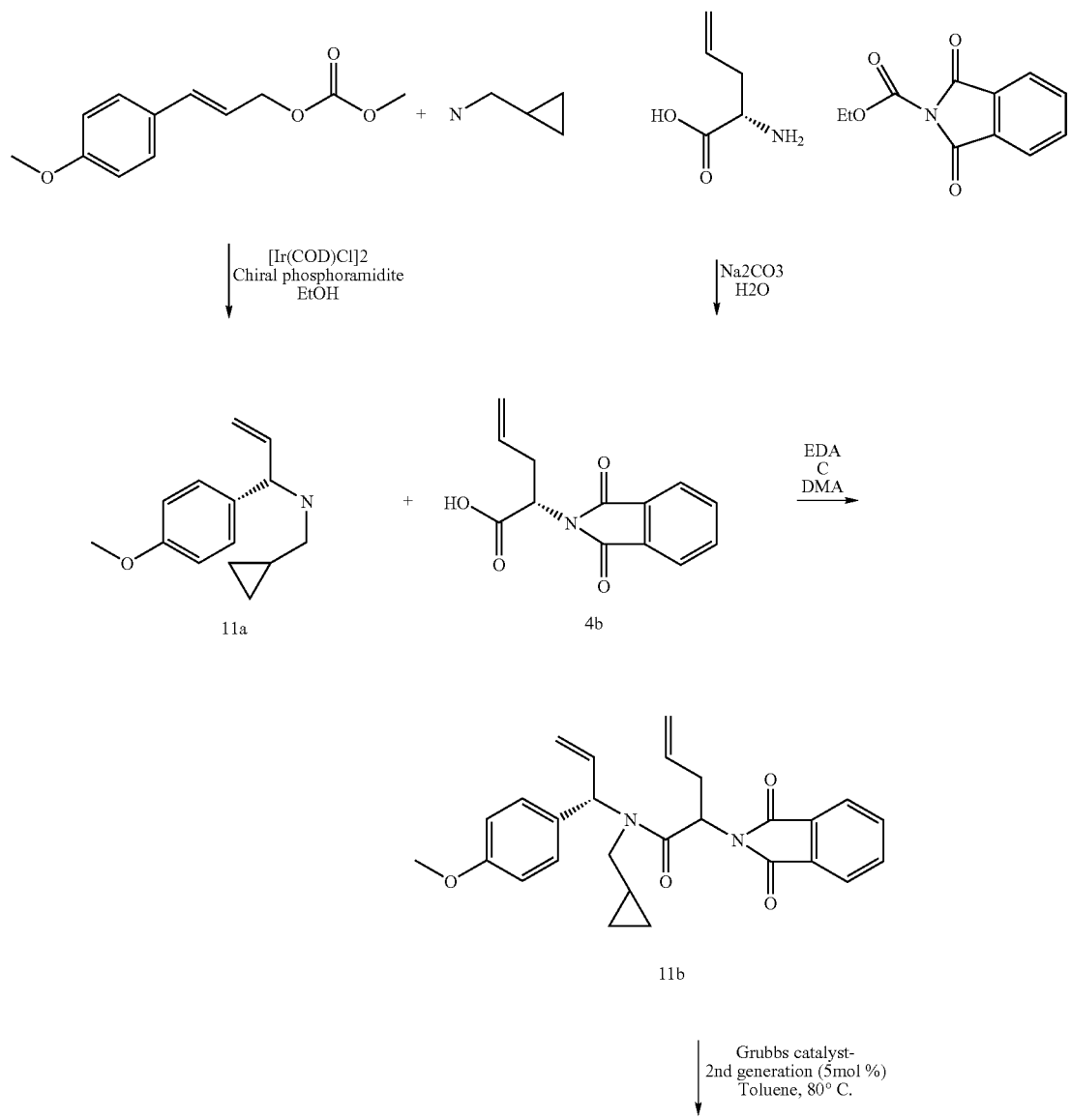

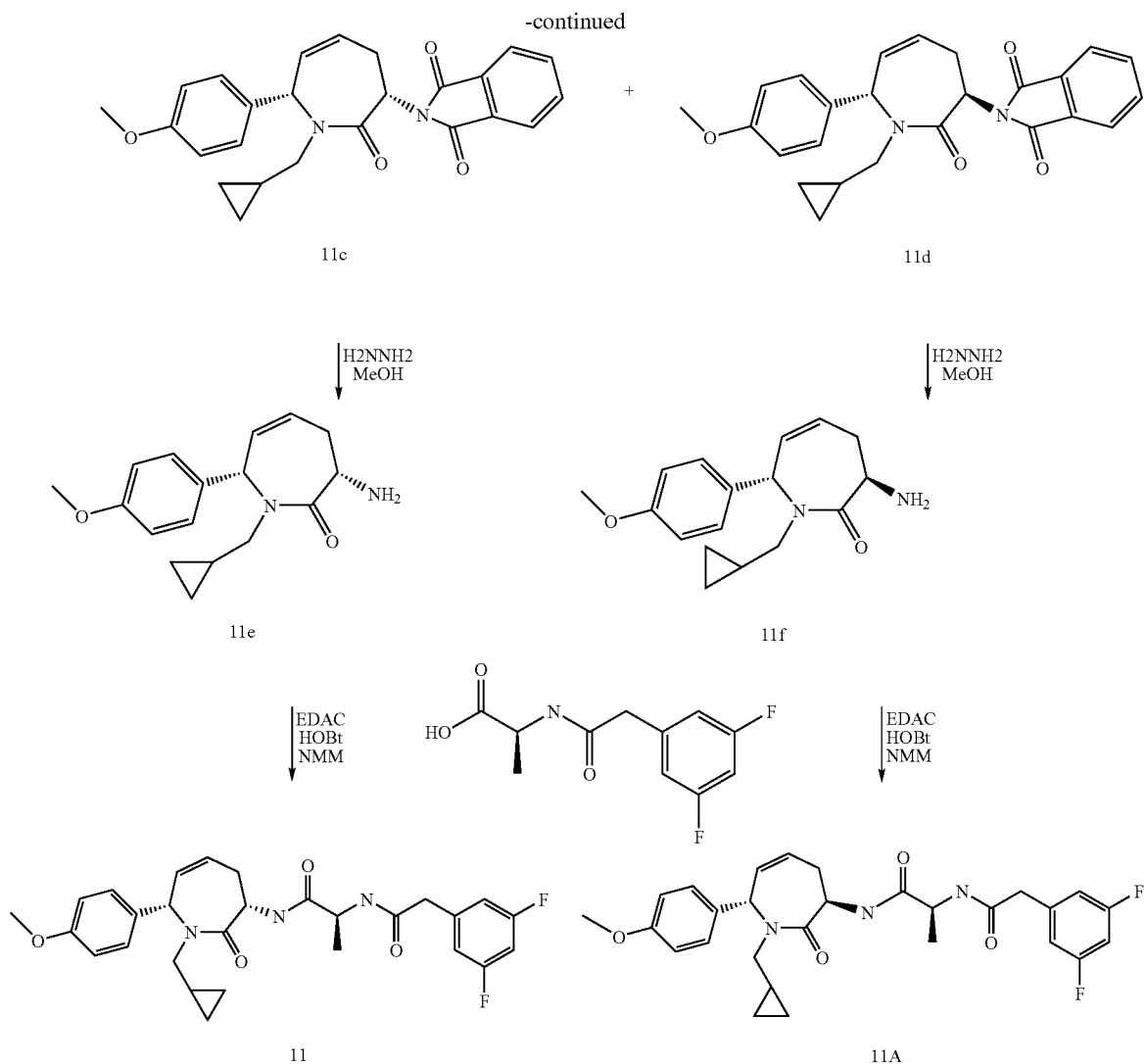

Example 11

N¹-[(3S,7S)-1-(cyclopropylmethyl)-7-(4-methoxyphenyl)-2-oxo-2,3,4,7-tetrahydro-1H-azepin-3-yl]-N²-[(3,5-difluorophenyl)acetyl]-L-alaninamide (11)

To a solution of (3S,7S)-3-amino-1-(cyclopylmethyl)-7-(4-methoxyphenyl)-1,3,4,7-tetrahydro-2H-azepin-2-one (11e) (45 mg) in DCM (3 mL) at 0° C. under $N_2$ was added N-[(3,5-difluorophenyl)acetyl]-L-alanine (38 mg), HOBt-hydrate (53 mg), EDAC.HCl (45 mg) and N-methyl morpholine (25 mg). The reaction mixture was stirred 1 h at 0° C. and 3H at room temperature, then diluted with 30% Hexanes/EtOAc (100 mL). The organic phase was consecutively washed with $H_2O$, 0.2 N HCl, saturated $NaHCO_3$, and brine, dried ($Na_2SO_4$), filtered and evaporated. The crude product was purified by flash chromatography (2% MeOH/DCM) to afford the title compound as an off-white solid (44 mg, 56%). ¹H NMR (300 MHz, $CDCl_3$) δ 0.40 (m, 2H), 0.58 (m, 2H), 1.29 (m, 3H), 1.75-1.99 (m, 2H), 3.10-3.26 (d, 2H), 3.66 (s, 1H), 3.80 (s, 2H), 4.60-4.69 (m, 1H), 4.96 (m, 1H), 5.31 (m, 1H), 6.13 (bd, 1H), 6.48 (m, 1H), 6.85-6.90 (m, 7H). MS APCI, m/z=512 (M+1). LC/MS 2.57 min., Method A.

Example 11A

N¹-[(3R,7S)-1-(cyclopropylmethyl)-7-(4-methoxyphenyl)-2-oxo-2,3,47-tetrahydro-1H-azepin-3-yl]-N²-[(3,5-difluorophenyl)acetyl]-L-alaninamide Utilizing (3R,7S)-3-amino-1-(cyclopropylmethyl)-7-(4-methoxyphenyl)-1,3,4,7-tetrahydro-2H-azepin-2-one (11f), the title compound was synthesized using the same procedure as that described for Example 11. The crude product was purified by flash chromatography (2% MeOH/DCM) to afford the title compound as an off-white solid (64%). ¹H NMR (300 MHz, $CDCl_3$) δ 0.40 (m, 2H), 0.58 (m, 2H), 1.29 (m, 3H), 1.75-1.99 (m, 2H), 3.10-3.26 (d, 2H), 3.66 (s, 3H), 3.80 (s, 2H), 4.60-4.69 (m, 1H), 4.97 (m, 1H), 5.31 (m, 1H), 6.13 (bd, 1H), 6.48 (m, 1H), 6.85-6.90 (m, 7H). MS APCI, m/z=512 (M+1). LC/MS 2.32 min., Method A.

The stereoselective allylic amine (1S)-N-(cyclopropylmethyl)-1-(4-methoxyphenyl)prop-2-en-1-amine (11a) was prepared by Iridium Complex-Catalyzed allylic amination of allylic esters:

a. (1S)-N-(cyclopropylmethyl)-1-(4-methoxyphenyl)prop-2-en-1-amine (11a)

A mixture of (2E)-3-(4-methoxyphenyl)prop-2-en-1-yl methyl carbonate (440 mg), N,N-bis[(1S)-1-phenylethyl]dinaphtho[1,2-f:2',1'-d][1,3,2]dioxaphosphepin-4-amine (108 mg), [Ir(COD)Cl]2 (27 mg), cyclopropyl methyl amine (374 µL) and EtOH (5 mL) was stirred under refluxing EtOH for 6H under N2. The progress of the reaction was monitered by HPLC. At the end of the reaction, addition of co-solvent (20 ml EtOH and 20 ml THF) and MP-TsOH resin (6 g) and the mixture was allowed to stirred at RT with swilling every 15 mins for 2-3 hours. Filtered the resin and washed the resin with plenty of EtOH, THF, DCM. The resin was taken up in 3.5N NH3 in MeOH (20 mL) and let it stir for overnight. Filtered the resin and washed the resin excessively with EtOH, THF and DCM. Combined the filtrate and evaporated all the solvent. The crude product was purified by flash chromatography (10% EtOAc/Hexane) to afford the title compound as a viscous oil (365 mg, 84%). $^1$H NMR (300 MHz, CDCl$_3$) δ 0.27 (m, 2H), 0.47 (m, 2H), 1.10 (m, 1H), 2.40 (m, 2H), 3.75 (s, 3H), 4.51 (m, 1H), 5.25-5.39 (m, 3H), 6.89-7.06 (m, 4H) (revealed branched/linear ratio (9:1)). MS APCI, m/z=218 (M+1). LC/MS 1.1 min., Method A. 80% ee was determined by NMR in the presence of TFAE-d$_{11}$.

The starting amines (11e) and (11f) were prepared using the same procedure as described for amine 5e b. N-(cyclopropylmethyl)-2-(1,3-dioxo-1,3-dihydro-2H-isoindol-2-yl)-N-(1S)-1-(4-methoxyphenyl)prop-2-en-1-yl)pent-4-enamide (11b)

The crude product was purified via flash chromatography (20% EtOAc/hexanes) to give the desired product as a viscous oil (55%). NMR studies revealed that there are two diastereomers presented at the ratio 3:1 (cis: trans). $^1$H NMR (300 MHz, CDCl$_3$) δ 0.39 (m, 2H), 0.56 (m, 2H), 1.18 (m, 1H), 2.78 (m, 2H-diastereomer/rotamer mixture), 3.03 (m, 2H), 3.66 (s, 3H), 4.83 (m, 1H), 5.38-5.85 (m, 5H), 6.66-7.16 (m, 4H), 7.76-7.91 (m, 4H). MS APCI, m/z=445 (M+1). LC/MS 2.64-2.66 min., Method A.

c. 2-[(3S,7S)-1-(cyclopropylmethyl)-7-(4-methoxyphenyl)-2-oxo-2,3,4,7-tetrahydro-1H-azepin-3-yl]-1H-isoindole-1,3(2H)-dione (11c)

The crude product was directly purified via flash chromatography (gradient—5%, 10%, 15% and 20% EtOAc/hexanes) to give the title compound (3c) (50%). $^1$H NMR (300 MHz, CDCl$_3$) δ 0.39 (m, 2H), 0.56 (m, 2H), 1.24 (m, 1H), 1.48-1.80 (m, 2H), 3.11-3.27 (m, 2H), 3.66 (s, 3H), 4.54 (m, 2H), 4.92 (d, 1H), 5.94 (m, 1H), 6.15 (m, 1H), 6.89-6.93 (m, 4H), 7.80-7.90 (m, 4H). MS APCI, m/z=417 (M+1). LC/MS 2.64 min., Method A.

d. 2-[(3R,7S)-1-(cyclopropylmethyl)-7-(4-fluorophenyl)-2-oxo-2,3,4,7-tetrahydro-1H-azepin-3-yl]-1H-isoindole-1,3(2H)-dione (11d) (15%) (combined yield of 65%)

$^1$H NMR (300 MHz, CDCl$_3$) δ 0.39 (m, 2H), 0.56 (m, 2H), 1.24 (m, 1H), 1.48-1.80 (m, 2H), 3.11-3.27 (m, 2H), 3.66 (s, 3H), 4.54 (m, 2H), 4.92 (d, 1H), 5.94 (m, 1H), 6.15 (m, 1H), 6.89-6.93 (m, 4H), 7.80-7.90 (m, 4H). MS APCI, m/z=417 (M+1). LC/MS 2.66 min., Method A.

e. (3S,7S)-3-amino-1-(cyclopropylmethyl)-7-(4-methoxyphenyl)-1,3,4,7-tetrahydro-2H-azepin-2-one (11e)

The title compound was isolated as a viscous oil (72%). $^1$H NMR (300 MHz, CDCl$_3$) 0.39 (m, 2H), 0.56 (m, 2H), 1.26 (m, 1H), 1.63-1.90 (m, 2H), 3.13-3.28 (m, 2H), 3.66 (s, 3H), 4.34 (m, 1H), 5.16 (d, 1H), 6.09 (m, 1H), 6.14 (m, 1H), 6.83-6.94 (m, 4H). MS APCI, m/z=287 (M+1). LC/MS 1.50 min, Method A.

f. (3R,7S)-3-amino-1-(cyclopropylmethyl)-7-(4-methoxyphenyl)-1,3,4,7-tetrahydro-2H-azepin-2-one (11f)

The title compound was isolated as a viscous oil (80%). $^1$H NMR (300 MHz, CDCl$_3$) δ 0.39 (m, 2H), 0.56 (m, 2H), 1.26 (m, 1H), 1.63-1.90 (m, 2H), 3.13-3.28 (m, 2H), 3.66 (s, 3H), 4.34 (m, 1H), 5.16 (d, 1H), 6.09 (m, 1H), 6.14 (m, 1H), 6.83-6.94 (m, 4H). MS APCI, m/z=287 (M+1). LC/MS 1.46 min, Method A.

Example 12

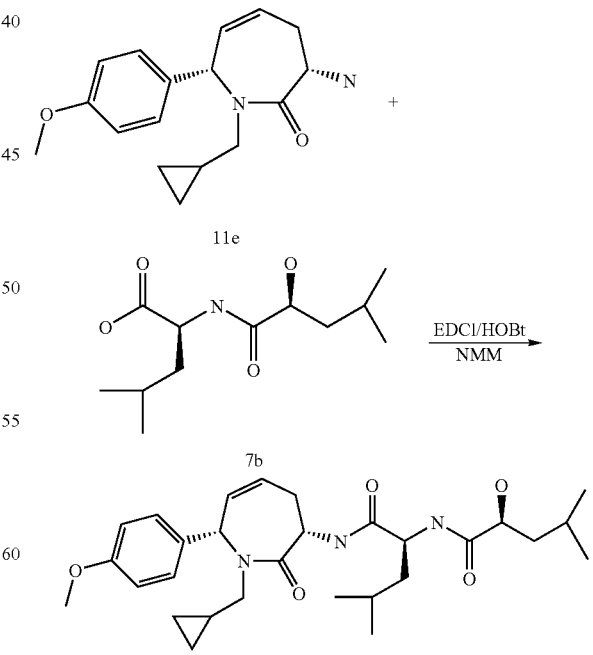

12

Example 12

N$^1$-[(3S,7S)-1-(cyclopropylmethyl)-7-(4-methoxyphenyl)-2-oxo-2,3,4,7-tetrahydro-1H-azepin-3-yl]-N$^2$-[(2S)-2-hydroxy-4-methylpentanoyl]-L-leucinamide To a solution of (3S,7S)-3-amino-1-(cyclopylmethyl)-7-(4-methoxyphenyl)-1,3,4,7-tetrahydro-2H-azepin-2-one (11e) (35 mg) in DCM (3 mL) at 0° C. under N$_2$ was added N-[(2S)-2-hydroxy-4-methylpentanoyl]-L-leucine (7b) (30 mg), HOBt-hydrate (41 mg), EDAC.HCl (35 mg) and N-methyl morpholine (25 mg). The reaction mixture was stirred 1 h at 0° C. and 3H at room temperature, then diluted with 30% Hexanes/EtOAc (100 mL). The organic phase was consecutively washed with H$_2$O, 0.2 N HCl, saturated NaHCO$_3$, and brine, dried (Na$_2$SO$_4$), filtered and evaporated. The crude product was purified by flash chromatography (2% MeOH/DCM) to afford the title compound as an off-white solid (60 mg, 95%). $^1$H NMR (300 MHz, CDCl$_3$) δ 0.40 (m, 2H), 0.58 (m, 2H), 0.74 (m, 1H), 0.87 (d, 6H), 1.26 (m, 1H), 1.53, (m, 2H), 1.59 (m, 1H), 1.67 (m, 2H), 2.00 (m, 2H), 3.20 (m, 2H), 3.66 (s, 1H), 3.89 (m, 1H), 4.28 (m, 1H), 4.96 (m, 1H), 5.32 (m, 1H), 6.13 (bd, 1H), 6.48 (m, 1H), 6.85-6.94 (m, 4H). MS APCI, m/z=514 (M+1). LC/MS 2.47 min., Method A.

The compounds of the present invention are useful for the prevention and treatment of Alzheimer's disease. Without being bond by any specific theory, it is the current understanding that the compounds of the present invention function by inhibiting amyloid β production. Methods of treatment target formation of amyloid P production through enzymes involved in the proteolytic processing of 1 amyloid precursor protein. Compounds that inhibit β and γ secretase activity, either directly or indirectly, controls the production of amyloid β. The inhibitions of β and γ secretases reduce the production of amyloid β and are thought to reduce or prevent the neurological disorders such as Alzheimer's disease. The compounds of the present invention have utility for the prevention and treatment of disorders involving amyloid β production, such as cerebrovascular disorders.

Compounds of the present invention have been shown to inhibit amyloid β production, as determined by the gamma secretase detergent extract assay and gamma secretase whole cell described below.

Compounds provided by this invention should also be useful as standards and reagents in determining the ability of a potential pharmaceutical to inhibit amyloid β production. These would be provided in commercial kits comprising a compound of this invention.

As used herein "ug" denotes microgram, "mg" denotes milligram, "g" denotes gram, "uL" denotes microliter, "mL" denotes milliliter, "L" denotes liter, "nM" denotes nanomolar, ".uM" denotes micromolar, "mM" denotes millimolar, "M" denotes molar, "nm" denotes nanometer, "DMSO" denotes dimethyl sulfoxide, "DTT" denotes, "DPBS" denotes "EDTA" denotes ethylenediaminetetraacetate, Gamma Secretase Detergent Extract Assay The gamma secretase enzyme assay measures the amount of amyloid β (Aβ)40 product generated by the cleavage of C100, a truncated form of amyloid precursor protein (APP). The C100 substrate is a recombinant protein purified from *E. coli* inclusion bodies. The γ secretase enzyme complex is prepared by detergent extraction of HeLa 8A8 cell membranes. The enzyme reaction contains 10 μl of inhibitor at a defined concentration, diluted from a DMSO stock into 96-well microplates (final concentration of DMSO is maintained at 5%). 20 ul of the C100 substrate (600 nM final concentration), in reaction buffer, (50 mM MES, pH 6.5, containing 100 mM NaCl, 1 mM EDTA, 1 mM DTT, 1 mg/mL BSA, 0.25% Chapso, 0.01% PE, 0.01% PC and a protease cocktail), is added to the plates. The reactions are initiated by addition of 10 ul enzyme at a 20-fold dilution from stock. An Aβ40 standard curve diluted in the reaction buffer plus C100 is included in each assay. Plates are incubated for 3 hours at 37 degrees. After the incubation period, 50 μl of an antibody mixture is added: rabbit anti-Aβ40 antibody (Biosource #44-3481) at 0.16 ug/ml and biotinylated 4G8 (Senetek #240-10) at 0.25 ug/ml in DPBS (Fisher # MT21031CV) containing 0.5% bovine serum albumin, 0.5% Tween 20. Plates are then incubated overnight at 4 degrees. The following morning, a 50 ul mixture of 0.0625 mg/ml Ruthenium labeled goat anti-rabbit IgG (labeled in-house) and 125 ug/ml of Streptavadin beads (Igen #M280), diluted in the same DPBS buffer, is added to detect the cleaved product. After an one hour incubation period at room temperature, an Igen M Series instrument is utilized to quantitate the results by electrochemiluminescence.

Gamma Secretase Whole Cell Assay (GSWC)

Preparation of Cells for Assay

Human Embryonic Kidney (HEK) cells stably expressing human Amyloid Precursor protein (APP) and Presenelin I were grown in DMEM media (Fisher MT10013CV) containing 10% fetal calf serum (Fisher #MT135011CV), 0.2 mg/mL G418 (Fisher #MT30234CR) and 1× concentration of antibiotic/antimycotic mixture (Fisher #MT30004CI). Cells were grown in tissue culture flasks and passaged every week at a ratio of 1:30.

Thirty minutes prior to incubation with test compounds, cells were harvested by treating the monolayer with DPBS (Fisher #MT21031CV) containing 3 mM EDTA. Cells were resuspended at a density of 2 million cells/mL in complete growth medium.

Aβ 40 Assay

Test compounds were solubilized in DMSO at a concentration of 3.3 mM. From this stock solution a dilution series was prepared in complete growth medium of cells. Dilution series were then transferred to 96 well assay plate (Costar #3595) with 100 μL in each well. Cells (100 μL) were added to each well containing test compound. Two controls, one containing only cells (Total) and one containing only growth medium (Background) were also included. Cells were incubated with compounds for 14-16 hours in cell culture incubator.

At the end of 14-16 hour incubation, 100 μL of supernatant was transferred from each well in to a polypropylene 96 well plate. This supernatant was mixed with 100 μL of DPBS (Fisher # MT21031CV) containing 0.5% bovine serum albumin, 0.5% Tween 20, 0.25 μg/mL of biotinylated 4G8 (Senetek #240-10), 0.18 μg/mL rabbit anti-Aβ40 antibody (Biosource #44-3481), 0.045 μg/mL Ruthenium labeled goat anti-rabbit IgG (labeled in-house) and 60 μg/mL of Streptavadin beads (Igen #M280). The mixture was incubated for 4-6 hours at 4° C. on a plate shaker.

At the completion of 4-6 hour incubation, plate was brought to room temperature and the generated Aβ40 was detected using the Igen M8 analyzer. Raw data was imported into Microsoft Excel software. IC$_{50}$ values for inhibition of Aβ40 generation by test compounds were calculated using Excel-Fit.

The invention claimed is:
1. A compound of formula (I):

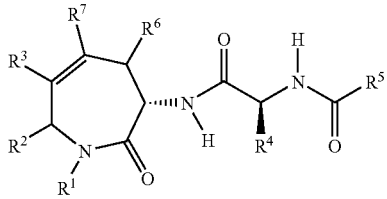

wherein:
R$^1$ is selected from H, optionally substituted C$_{1-3}$alkylaryl, optionally substituted C$_{1-3}$alkylheterocycle, optionally substituted alkyl, optionally substituted C$_{3-6}$cycloalkyl, C$_{2-4}$alkylNR$^a$R$^b$, and C$_{1-4}$alkylCOR$^d$, wherein all such optional substitutions are made with 0, 1, 2 or 3 R$^e$;
R$^a$ and R$^b$ are, at each occurrence independently selected from H, C$_{1-4}$alkyl and C$_{5-6}$cycloalkyl, or R$^a$ and R$^b$ and the N to which they are attached in combination form a 5 or 6-membered N-linked heterocycle having 2 nitrogen or, 1 nitrogen and 1 oxygen, ring atoms, wherein the non-linked nitrogen is substituted with R$^c$;
R$^c$ is, at each occurrence independently selected from H, C$_{1-3}$alkyl, and substituted phenyl with 0, 1, 2, or 3 R$^e$;
R$^d$ is, at each occurrence independently selected from C$_{1-3}$alkyl, C$_{1-3}$alkoxy, and NR$^a$R$^b$;
R$^e$ is, at each occurrence independently selected from OH, F, Cl, Br, I, CN, NO$_2$, CF$_3$, C$_{1-6}$alkyl, or C$_{1-6}$alkoxy;
R$^2$, R$^3$, R$^6$ and R$^7$ are independently selected from H, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, optionally substituted C$_{1-3}$alkylaryl, optionally substituted C$_{1-3}$alkylheterocycle, optionally substituted C$_{1-6}$alkyl, and optionally substituted C$_{3-6}$cycloalkyl, wherein all such optional substitutions are made with 0, 1, 2, or 3 R$^e$ moieties, with the requirement that one or more of R$^2$, R$^3$, R$^6$ and R$^7$ are aromatic or heteroaromatic;
R$^4$ is H, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, C$_{1-6}$alkyl, C$_{3-6}$ cycloalkyl, or CR$^9$R$^{10}$R$^{11}$;
R$^5$ is —C$_{1-6}$alkyl, —C$_{1-3}$alkylR$^{12}$ or CH(OH)R$^{13}$;
R$^9$, R$^{10}$ and R$^{11}$ are, at each occurrence independently selected from H, F, C$_{1-4}$alkyl, OH, OCH$_3$, SH, SCH$_3$, and CH$_2$SCH$_3$;
R$^{12}$ is phenyl substituted with 0, 1, 2 or 3 R$^e$; and
R$^{13}$ is C$_{1-6}$alkyl or R$^{12}$;
or a pharmaceutically acceptable salt thereof.
2. A compound of claim 1, wherein:
R$^1$ is selected from H, and optionally substituted alkyl, wherein such optional substitution is made with 0, 1, or 2 substituents selected from C$_{1-6}$cycloalkyl, C$_{1-6}$cycloalkoxy, or phenyl;
R$^2$, R$^3$, R$^6$ and R$^7$ are independently selected from H, or optionally substituted 6-membered aromatic, wherein such optional substitution is made with 0, 1, 2 or 3 R$^e$ moieties, with the requirement that one or more of R$^2$, R$^3$, R$^6$ and R$^7$ are aromatic;
R$^4$ is H, or C$_{1-6}$alkyl;
R$^5$ is —C$_{1-6}$alkyl, or —C$_{1-3}$alkylR$^{12}$;
R$^{12}$ is phenyl substituted with 0, 1, 2 or 3 R$^e$;
R$^e$ is, at each occurrence independently selected from OH, F, Cl, Br, I, CN, NO$_2$, CF$_3$, C$_{1-6}$alkyl, and C$_{1-6}$alkoxy;
or a pharmaceutically acceptable salt thereof.
3. A compound of claim 1, wherein:
R$^1$ is selected from H, —C$_{1-6}$alkyl, —(CH$_2$)$_2$OCH$_3$, —CH$_2$-phenyl, —CH$_2$C$_{1-6}$cycloalkyl;
R$^2$, R$^3$, R$^6$ and R$^7$ are independently selected from H, and a substituted phenyl, wherein such substituent is selected from 1, 2, or 3 of the following F, Cl, Br, I or OCH$_3$;
R$^4$ is H, or C$_{1-6}$alkyl;
R$^5$ is —C$_{1-6}$alkyl, or —C$_{1-3}$alkylR$^{12}$ wherein R$^{12}$ is a substituted phenyl, wherein such substituent is selected from 1, 2 or 3 of the following F, Cl, Br, I and OCH$_3$;
or a pharmaceutically acceptable salt thereof.
4. A compound of claim 1, wherein:
R$^1$ is —C$_{1-3}$alkyl or —CH$_2$C$_{1-4}$cycloalkyl.
5. A compound of claim 1, wherein:
R$^1$ is methyl or —CH$_2$cyclopropane.
6. A compound of claim 1, wherein:
R$^e$ is, at each occurrence independently selected from F, Cl, CF$_3$, C$_{1-6}$alkyl, and C$_{1-6}$alkoxy.
7. A compound of claim 1, wherein:
R$^2$ is an optionally substituted phenyl, wherein such optional substitution is made with 0, 1, 2, or 3 R$^e$ moieties.
8. A compound of claim 1, wherein:
R$^3$, R$^6$ and R$^7$ are H.
9. A compound of claim 1, wherein:
R$^4$ is C$_{1-6}$alkyl.
10. A compound of claim 1, wherein:
R$^5$ is —C$_{1-6}$alkyl or —C$_{1-3}$alkylR$^{12}$ wherein R$^{12}$ is a substituted phenyl, wherein such substituent is selected from 1, 2 or 3 of the following F, Cl, Br, I and OCH$_3$.
11. A compound of claim 1 selected from:
N$^2$-[(3,5-difluorophenyl)acetyl]-N$^1$-[(3S,7S)-1-methyl-2-oxo-7-phenyl-2,3,4,7-tetrahydro-1H-azepin-3-yl]-L-alaninamide;
N$^2$-[(3,5-difluorophenyl)acetyl]-N$^1$-[(3S,7R)-1-methyl-2-oxo-7-phenyl-2,3,4,7-tetrahydro-1H-azepin-3-yl]-L-alaninamide;
N$^1$-[(3S,7S)-1-(cyclopropylmethyl)-2-oxo-7-phenyl-2,3,4,7-tetrahydro-1H-azepin-3-yl]-N$^2$-[(3,5-difluorophenyl)acetyl]-L-alaninamide;
N$^1$-[(3S,7R)-1-(cyclopropylmethyl)-2-oxo-7-phenyl-2,3,4,7-tetrahydro-1H-azepin-3-yl]-N$^2$-[(3,5-difluorophenyl)acetyl]-L-alaninamide;
N$^1$-[(3S,7S)-1-benzyl-2-oxo-7-phenyl-2,3,4,7-tetrahydro-1H-azepin-3-yl]-N$^2$-[(3,5-difluorophenyl)acetyl]-L-alaninamide;
N$^1$-[(3S,7R)-1-benzyl-2-oxo-7-phenyl-2,3,4,7-tetrahydro-1H-azepin-3-yl]-N$^2$-[(3,5-difluorophenyl)acetyl]-L-alaninamide;
N$^2$-[(3,5-difluorophenyl)acetyl]-N$^1$-[(3S,7S)-1-(2-methoxyethyl)-2-oxo-7-phenyl-2,3,4,7-tetrahydro-1H-azepin-3-yl]-L-alaninamide;
N$^2$-[(3,5-difluorophenyl)acetyl]-N$^1$-[(3S,7R)-1-(2-methoxyethyl)-2-oxo-7-phenyl-2,3,4,7-tetrahydro-1H-azepin-3-yl]-L-alaninamide;
N$^2$-[(2S)-2-hydroxy-4-methylpentanoyl]-N$^1$-[(3S,7S)-1-(2-methoxyethyl)-2-oxo-7-phenyl-2,3,4,7-tetrahydro-1H-azepin-3-yl]-L-leucinamide;

N$^1$-[(3R,7S)-1-cyclopentyl-2-oxo-7-phenyl-2,3,4,7-tetrahydro-1H-azepin-3-yl]-N$^2$-[(3,5-difluorophenyl)acetyl]-L-alaninamide;

N$^1$-[(3S,7S)-1-cyclopentyl-2-oxo-7-phenyl-2,3,4,7-tetrahydro-1H-azepin-3-yl]-N$^2$-[(3,5-difluorophenyl)acetyl]-L-alaninamide;

N$^1$-[(3R,7S)-1-isobutyl-2-oxo-7-phenyl-2,3,4,7-tetrahydro-1H-azepin-3-yl]-N$^2$-[(3,5-difluorophenyl)acetyl]-L-alaninamide;

N$^1$-[(3S,7S)-1-isobutyl-2-oxo-7-phenyl-2,3,4,7-tetrahydro-1H-azepin-3-yl]-N$^2$-[(3,5-difluorophenyl)acetyl]-L-alaninamide;

N$^1$-[(3S,7S)-1-(cyclopropylmethyl)-7-(4-fluorophenyl)-2-oxo-2,3,4,7-tetrahydro-1H-azepin-3-yl]-N$^2$-[(3,5-difluorophenyl)acetyl]-L-alaninamide;

N$^1$-[(3R,7S)-1-(cyclopropylmethyl)-7-(4-fluorophenyl)-2-oxo-2,3,4,7-tetrahydro-1H-azepin-3-yl]-N$^2$-[(3,5-difluorophenyl)acetyl]-L-alaninamide N$^1$-[(3S,7S)-1-(cyclopropylmethyl)-7-(4-methoxyphenyl)-2-oxo-2,3,4,7-tetrahydro-1H-azepin-3-yl]-N$^2$-[(3,5-difluorophenyl)acetyl]-L-alaninamide (11)

N$^1$-[(3R,7S)-1-(cyclopropylmethyl)-7-(4-methoxyphenyl)-2-oxo-2,3,4,7-tetrahydro-1H-azepin-3-yl]-N$^2$-[(3,5-difluorophenyl)acetyl]-L-alaninamide;

N$^1$-[(3S,7S)-1-(cyclopropylmethyl)-7-(4-methoxyphenyl)-2-oxo-2,3,4,7-tetrahydro-1H-azepin-3-yl]-N$^2$-[(2S)-2-hydroxy-4-methylpentanoyl]-L-leucinamide;

N$^2$-[(2S)-2-(3,5-difluorophenyl)-2-hydroxyacetyl]-N$^1$-[(3S,7S)-1-methyl-2-oxo-7-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S,7S)-1-methyl-2-oxo-7-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S,7S)-2-oxo-7-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S,7S)-2-oxo-7-phenyl-2,3,4,7-tetrahydro-1H-azepin-3-yl]-L-alaninamide;

N$^2$-[(3,5-difluorophenyl)acetyl]-N$^1$-[(3S)-1-methyl-2-oxo-6-phenyl-2,3,4,7-tetrahydro-1H-azepin-3-yl]-L-alaninamide;

N$^2$-[(3,5-difluorophenyl)acetyl]-N$^1$-[(3S)-2-oxo-6-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S)-1-methyl-2-oxo-6-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S)-1-methyl-2-oxo-6-2,3,4,7-tetrahydro-1H-azepin-3-yl]-L-alaninamide;

N$^2$-[(2R)-2-(3,5-difluorophenyl)-2-hydroxyacetyl]-N$^1$-[(3S)-2-oxo-6-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S)-2-oxo-6-phenyl-2,3,4,7-tetrahydro-1H-azepin-3-yl]-L-alaninamide;

N$^2$-[(3,5-difluorophenyl)acetyl]-N$^1$-[(3S)-1-methyl-2-oxo-5-phenyl-2,3,4,7-tetrahydro-1H-azepin-3-yl]-L-alaninamide;

N$^2$-[(3,5-difluorophenyl)acetyl]-N$^1$-[(3S)-2-oxo-5-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S)-1-methyl-2-oxo-5-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S)-1-methyl-2-oxo-5-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S)-2-oxo-5-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S)-2-oxo-5-phenyl-2,3,4,7-tetrahydro-1H-azepin-3-yl]-L-alaninamide;

N$^2$-[(3,5-difluorophenyl)acetyl]-N$^1$-[(3S,4S)-1-methyl-2-oxo-4-phenyl-2,3,4,7-tetrahydro-1H-azepin-3-yl]-L-alaninamide;

N$^2$-[(3,5-difluorophenyl)acetyl]-N$^1$-[(3S,4S)-2-oxo-4-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S,4S)-1-methyl-2-oxo-4-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S,4S)-1-methyl-2-oxo-4-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S,4S)-2-oxo-4-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S,4S)-2-oxo-4-phenyl-2,3,4,7-tetrahydro-1H-azepin-3-yl]-L-alaninamide;

N$^2$-[(3,5-difluorophenyl)acetyl]-N$^1$-[(3S,4R)-1-methyl-2-oxo-4-phenyl-2,3,4,7-tetrahydro-1H-azepin-3-yl]-L-alaninamide;

N$^2$-[(3,5-difluorophenyl)acetyl]-N$^1$-[(3S,4R)-2-oxo-4-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S,4R)-1-methyl-2-oxo-4-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S,4R)-1-methyl-2-oxo-4-phenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S,4R)-2-oxo-4-phenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S,4R)-2-oxo-4-phenyl-2,3,4,7-tetrahydro-1H-azepin-3-yl]-L-alaninamide;

N$^2$-[(3,5-difluorophenyl)acetyl]-N$^1$-[(3S,4S,7S)-1-methyl-2-oxo-4,7-diphenyl-2,3,4,7-tetrahydro-1H-azepin-3-yl]-L-alaninamide;

N$^2$-[(3,5-difluorophenyl)acetyl]-N$^1$-[(3S,4S,7S)-2-oxo-4,7-diphenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S,4S,7S)-1-methyl-2-oxo-4,7-diphenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S,4S,7S)-1-methyl-2-oxo-4,7-diphenyl-2,3,4,7-tetrahydro-1H-azepin-3-yl]-L-alaninamide;

N$^2$-[(2S)-2-(3,5-difluorophenyl)-2-hydroxyacetyl]-N$^1$-[(3S,4S,7S)-2-oxo-4,7-diphenyl-2,3,4,7-tetrahydro-1H-azepin-3-yl]-L-alaninamide;

N$^2$-[(2R)-2-(3,5-difluorophenyl)-2-hydroxyacetyl]-N$^1$-[(3S,4S,7S)-2-oxo-4,7-diphenyl-2,3,4,7-tetrahydro-1H-azepin-3-yl]-L-alaninamide;

N$^2$-[(3,5-difluorophenyl)acetyl]-N$^1$-[(3S,4R,7S)-1-methyl-2-oxo-4,7-diphenyl-2,3,4,7-tetrahydro-1H-azepin-3-yl]-L-alaninamide;

N²-[(3,5-difluorophenyl)acetyl]-N¹-[(3S,4R,7S)-2-oxo-4,7-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,4R,7S)-1-methyl-2-oxo-4,7-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,4R,7S)-1-methyl-2-oxo-4,7-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,4R,7S)-2-oxo-4,7-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,4R,7S)-2-oxo-4,7-diphenyl-2,3,4,7-tetrahydro-1H-azepin-3-yl]-L-alaninamide;
N²-[(3,5-difluorophenyl)acetyl]-N¹-[(3S,4R,7R)-1-methyl-2-oxo-4,7-diphenyl-2,3,4,7-tetrahydro-1H-azepin-3-yl]-L-alaninamide;
N²-[(3,5-difluorophenyl)acetyl]-N¹-[(3S,4R,7R)-2-oxo-4,7-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,4R,7R)-1-methyl-2-oxo-4,7-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,4R,7R)-1-methyl-2-oxo-4,7-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,4R,7R)-2-oxo-4,7-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,4R,7R)-2-oxo-4,7-diphenyl-2,3,4,7-tetrahydro-1H-azepin-3-yl]-L-alaninamide;
N²-[(3,5-difluorophenyl)acetyl]-N¹-[(3S,7R)-1-methyl-2-oxo-5,7-diphenyl-2,3,4,7-tetrahydro-1H-azepin-3-yl]-L-alaninamide;
N²-[(3,5-difluorophenyl)acetyl]-N¹-[(3S,7R)-2-oxo-5,7-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,7R)-1-methyl-2-oxo-5,7-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,7R)-1-methyl-2-oxo-5,7-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,7R)-2-oxo-5,7-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,7R)-2-oxo-5,7-diphenyl-2,3,4,7-tetrahydro-1H-azepin-3-yl]-L-alaninamide;
N²-[(3,5-difluorophenyl)acetyl]-N¹-[(3S,7S)-1-methyl-2-oxo-5,7-diphenyl-2,3,4,7-tetrahydro-1H-azepin-3-yl]-L-alaninamide;
N²-[(3,5-difluorophenyl)acetyl]-N¹-[(3S,7S)-2-oxo-5,7-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,7S)-1-methyl-2-oxo-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,7S)-1-methyl-2-oxo-5,7-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,7S)-2-oxo-5,7-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,7S)-2-oxo-5,7-diphenyl-2,3,4,7-tetrahydro-1H-azepin-3-yl]-L-alaninamide;
N²-[(3,5-difluorophenyl)acetyl]-N¹-[(3S,4R)-1-methyl-2-oxo-4,6-diphenyl-2,3,4,7-tetrahydro-1H-azepin-3-yl]-L-alaninamide;
N²-[(3,5-difluorophenyl)acetyl]-N¹-[(3S,4R)-2-oxo-4,6-diphenyl-2,3,4,7-tetrahydro-azepin-3-yl]-L-alaninamide;
N²-[(2S)-2-(3,5-difluorophenyl)-2-hydroxyacetyl]-N¹-[(3S,4R)-1-methyl-2-oxo-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,4R)-1-methyl-2-oxo-4,6-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,4R)-2-oxo-4,6-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,4R)-2-oxo-4,6-diphenyl-2,3,4,7-tetrahydro-1H-azepin-3-yl]-L-alaninamide;
N²-[(3,5-difluorophenyl)acetyl]-N¹-[(3S,4S)-1-methyl-2-oxo-4,6-diphenyl-2,3,4,7-tetrahydro-1H-azepin-3-yl]-L-alaninamide;
N²-[(3,5-difluorophenyl)acetyl]-N¹-[(3S,4S)-2-oxo-4,6-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,4S)-1-methyl-2-oxo-4,6-diphenyl-2,3,4,7-tetrahydro-1H-azepin-3-yl]-L-alaninamide;
N²-[(2R)-2-(3,5-difluorophenyl)-2-hydroxyacetyl]-N¹-[(3S,4S)-1-methyl-2-oxo-4,6-diphenyl-2,3,4,7-tetrahydro-1H-azepin-3-yl]-L-alaninamide;
N²-[(2S)-2-(3,5-difluorophenyl)-2-hydroxyacetyl]-N¹-[(3S,4S)-2-oxo-4,6-diphenyl-2,3,4,7-tetrahydro-1H-azepin-3-yl]-L-alaninamide; and
N²-[(2R)-2-(3,5-difluorophenyl)-2-hydroxyacetyl]-N¹-[(3S,4S)-2-oxo-4,6-diphenyl-2,3,4,7-tetrahydro-1H-azepin-3-yl]-L-alaninamide;

or pharmaceutically acceptable salt thereof.

12. A compound of formula (II):

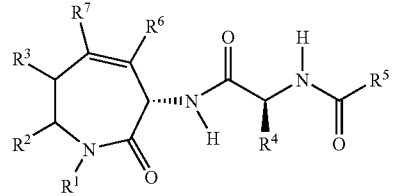

(II)

wherein:
$R^1$ is selected from H, optionally substituted $C_{1-3}$alkylaryl, optionally substituted $C_{1-3}$alkylheterocycle, optionally substituted alkyl, optionally substituted $C_{3-6}$cycloalkyl, $C_{2-4}$alkylNR$^a$R$^b$, and $C_{1-4}$alkylCOR$^d$, wherein all such optional substitutions are made with 0, 1, 2 or 3 R$^e$;

$R^a$ and $R^b$ are, at each occurrence independently selected from H, $C_{1-4}$alkyl and $C_{5-6}$cycloalkyl, or $R^a$ and $R^b$ and the N to which they are attached in combination form a 5 or 6-membered N-linked heterocycle having 2 nitrogen or, 1 nitrogen and 1 oxygen, ring atoms, wherein the non-linked nitrogen is substituted with R$^c$;

R$^c$ is, at each occurrence independently selected from H, C$_{1-3}$alkyl, and substituted phenyl with 0, 1, 2, or 3 R$^e$;

R$^d$ is, at each occurrence independently selected from C$_{1-3}$alkyl, C$_{1-3}$alkoxy, and NR$^a$R$^b$;

R$^e$ is, at each occurrence independently selected from OH, F, Cl, Br, I, CN, NO$_2$, CF$_3$, C$_{1-6}$alkyl, and C$_{1-6}$alkoxy;

R$^2$, R$^3$, R$^6$ and R$^7$ are independently selected from H, optionally substituted 5- or 6-membered aromatic or heteroaromatic ring, said ring having 0, 1, 2, or 3, nitrogen, oxygen or sulfur atoms, but not more than 2 oxygen atoms or 2 sulfur atoms or 1 oxygen and 1 sulfur atom, optionally substituted C$_{1-3}$alkylaryl, optionally substituted C$_{1-3}$alkylheterocycle, optionally substituted C$_{1-6}$alkyl, and optionally substituted C$_{3-6}$ cycloalkyl, wherein all such optional substitutions are made with 0, 1, 2, or 3 R$^e$ moieties, with the requirement that one or more of R$^2$, R$^3$, R$^6$ and R$^7$ are aromatic or heteroaromatic;

R$^4$ is H, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, C$_{1-6}$alkyl, C$_{3-6}$ cycloalkyl, or CR$^9$R$^{10}$R$^{11}$;

R$^5$ is C$_{1-3}$alkylR$^{12}$ or CH(OH)R$^{13}$;

R$^9$, R$^{10}$ and R$^{11}$ are, at each occurrence independently selected from H, F, C$_{1-4}$alkyl, OH, OCH$_3$, SH, SCH$_3$, and CH$_2$SCH$_3$;

R$^{12}$ is phenyl substituted with 0, 1, 2 or 3 R$^e$;

R$^{13}$ is C$_{1-6}$alkyl or R$^{12}$;

or a pharmaceutically acceptable salt thereof.

13. A compound of claim 12, wherein:

R$^1$ is selected from H, and optionally substituted alkyl wherein such optional substitution is made with 0, 1, or 2 substituents selected from C$_{1-6}$cycloalkyl, C$_{1-6}$cycloalkoxy, and phenyl;

R$^2$, R$^3$, R$^6$ and R$^7$ are independently selected from H, and optionally substituted 6-membered aromatic, wherein such optional substitution is made with 0, 1, 2, or 3 R$^e$ moieties, with the requirement that one or more of R$^2$, R$^3$, R$^6$ and R$^7$ are aromatic;

R$^4$ is H, or C$_{1-6}$alkyl;

R$^5$ is C$_{1-3}$alkylR$^{12}$ or C$_{1-6}$alkyl;

R$^{12}$ is phenyl substituted with 0, 1, 2 or 3 R$^e$;

R$^e$ is, at each occurrence independently selected from OH, F, Cl, Br, I, CN, NO$_2$, CF$_3$, C$_{1-6}$alkyl, or C$_{1-6}$alkoxy;

or a pharmaceutically acceptable salt thereof.

14. A compound of claim 12, wherein:

R$^1$ is selected from H, —C$_{1-6}$alkyl, —(CH$_2$)$_2$OCH$_3$, —CH$_2$-phenyl, and —CH$_2$C$_{1-6}$cycloalkyl;

R$^2$, R$^3$, R$^6$ and R$^7$ are independently selected from H, and a substituted phenyl, wherein such substitutent is selected from 1, 2, or 3 of the following F, Cl, Br, I and OCH$_3$;

R$^4$ is H, or C$_{1-6}$alkyl;

R$^5$ is —C$_{1-6}$alkyl, or —C$_{1-3}$alkylR$^{12}$ wherein R$^{12}$ is a substituted phenyl, wherein such substituent is selected from 1, 2 or 3 of the following F, Cl, Br, I and OCH$_3$;

or a pharmaceutically acceptable salt thereof.

15. A compound of claim 12, wherein:

R$^1$ is selected from —C$_{1-3}$alkyl, and —CH$_2$C$_{1-4}$cycloalkyl.

16. A compound of claim 12, wherein:

R$^1$ is selected from methyl and —CH$_2$cyclopropane.

17. A compound of claim 12, wherein:

R$^e$ is at each occurrence independently selected from F, Cl, CF$_3$, C$_{1-6}$alkyl, and C$_{1-6}$alkoxy.

18. A compound of claim 12, wherein:

R$^2$ is an optionally substituted phenyl, wherein such optional substitution is made with 0, 1, 2, and 3 R$^e$ moieties.

19. A compound of claim 12, wherein:

R$^3$, R$^6$ and R$^7$ are H.

20. A compound of claim 12, wherein:

R$^4$ is C$_{1-6}$alkyl.

21. A compound of claim 12, wherein:

R$^5$ is —C$_{1-6}$alkyl, —C$_{1-3}$alkylR$^{12}$ wherein R$^{12}$ is a substituted phenyl, wherein such substituent is selected from 1, 2 and 3 of the following F, Cl, Br, I and OCH$_3$.

22. A compound of claim 12 selected from:

N$^2$-[(3,5-difluorophenyl)acetyl]-N$^1$-[(3S,7S)-1-methyl-2-oxo-7-phenyl-2,3,6,7-tetrahydro-1H-azepin-3-yl]-L-alaninamide;

N$^2$-[(3,5-difluorophenyl)acetyl]-N$^1$-[(3S,7S)-2-oxo-7-phenyl-2,3,6,7-tetrahydro-1H-azepin-3-yl]-L-alaninamide;

N$^2$-[(2S)-2-(3,5-difluorophenyl)-2-hydroxyacetyl]-N$^1$-[(3S,7S)-1-methyl-2-oxo-7-phenyl-2,3,6,7-tetrahydro-1H-azepin-3-yl]-L-alaninamide;

N$^2$-[(2R)-2-(3,5-difluorophenyl)-2-hydroxyacetyl]-N$^1$-[(3S,7S)-1-methyl-2-oxo-7-phenyl-2,3,6,7-tetrahydro-1H-azepin-3-yl]-L-alaninamide;

N$^2$-[(2S)-2-(3,5-difluorophenyl)-2-hydroxyacetyl]-N$^1$-[(3S,7S)-2-oxo-7-phenyl-2,3,6,7-tetrahydro-1H-azepin-3-yl]-L-alaninamide;

N$^2$-[(2R)-2-(3,5-difluorophenyl)-2-hydroxyacetyl]-N$^1$-[(3S,7S)-2-oxo-7-phenyl-2,3,6,7-tetrahydro-1H-azepin-3-yl]-L-alaninamide;

N$^2$-[(3,5-difluorophenyl)acetyl]-N$^1$-[(3S,7R)-1-methyl-2-oxo-7-phenyl-2,3,6,7-tetrahydro-1H-azepin-3-yl]-L-alaninamide;

N$^2$-[(3,5-difluorophenyl)acetyl]-N$^1$-[(3S,7R)-2-oxo-7-phenyl-2,3,6,7-tetrahydro-1H-azepin-3-yl]-L-alaninamide;

N$^2$-[(2S)-2-(3,5-difluorophenyl)-2-hydroxyacetyl]-N$^1$-[(3S,7R)-1-methyl-2-oxo-7-phenyl-2,3,6,7-tetrahydro-1H-azepin-3-yl]-L-alaninamide;

N$^2$-[(2R)-2-(3,5-difluorophenyl)-2-hydroxyacetyl]-N$^1$-[(3S,7R)-1-methyl-2-oxo-7-phenyl-2,3,6,7-tetrahydro-1H-azepin-3-yl]-L-alaninamide;

N$^2$-[(2S)-2-(3,5-difluorophenyl)-2-hydroxyacetyl]-N$^1$-[(3S,7R)-2-oxo-7-phenyl-2,3,6,7-tetrahydro-1H-azepin-3-yl]-L-alaninamide;

N$^2$-[(2R)-2-(3,5-difluorophenyl)-2-hydroxyacetyl]-N$^1$-[(3S,7R)-2-oxo-7-phenyl-2,3,6,7-tetrahydro-1H-azepin-3-yl]-L-alaninamide;

N$^2$-[(3,5-difluorophenyl)acetyl]-N$^1$-[(3S,6R)-1-methyl-2-oxo-6-phenyl-2,3,6,7-tetrahydro-1H-azepin-3-yl]-L-alaninamide;

N$^2$-[(3,5-difluorophenyl)acetyl]-N$^1$-[(3S,6R)-2-oxo-6-phenyl-2,3,6,7-tetrahydro-1H-azepin-3-yl]-L-alaninamide;

N 2-[(2S)-2-(3,5-difluorophenyl)-2-hydroxyacetyl]-N$^1$-[(3S,6R)-1-methyl-2-oxo-6-phenyl-2,3,6,7-tetrahydro-1H-azepin-3-yl]-L-alaninamide;

N$^2$-[(2R)-2-(3,5-difluorophenyl)-2-hydroxyacetyl]-N$^1$-[(3S,6R)-1-methyl-2oxo-6-phenyl-2,3,6,7-tetrahydro-1H-azepin-3-yl]-L-alaninamide;

N$^2$-[(2S)-2-(3,5-difluorophenyl)-2-hydroxyacetyl]-N$^1$-[(3S,6R)-2-oxo-6-phenyl-2,3,6,7-tetrahydro-1H-azepin-3-yl]-L-alaninamide;

N$^2$-[(2R)-2-(3,5-difluorophenyl)-2-hydroxyacetyl]-N$^1$-[(3S,6R)-2-oxo-6-phenyl-2,3,6,7-tetrahydro-1H-azepin-3-yl]-L-alaninamide;

N²-[(3,5-difluorophenyl)acetyl]-N¹-[(3S,6S)-1-methyl-2-oxo-6-phenyl-2,3,6,7-tetrahydro-1H-azepin-3-yl]-L-alaninamide;

N²-[(3,5-difluorophenyl)acetyl]-N¹-[(3S,6S)-2-oxo-6-phenyl-2,3,6,7-tetrahydro-1H-azepin-3-yl]-L-alaninamide;

N²-[(2S)-2-(3,5-difluorophenyl)-2-hydroxyacetyl]-N¹-[(3S,6S)-1-methyl-2-oxo-6-phenyl-2,3,6,7-tetrahydro-1H-azepin-3-yl]-L-alaninamide;

N²-[(2R)-2-(3,5-difluorophenyl)-2-hydroxyacetyl]-N¹-[(3S,6S)-1-methyl-2-oxo-6-phenyl-2,3,6,7-tetrahydro-1H-azepin-3-yl]-L-alaninamide;

N²-[(2S)-2-(3,5-difluorophenyl)-2-hydroxyacetyl]-N¹-[(3S,6S)-2-oxo-7-phenyl-2,3,6,7-tetrahydro-1H-azepin-3-yl]-L-alaninamide;

N²-[(2R)-2-(3,5-difluorophenyl)-2-hydroxyacetyl]-N¹-[(3S,6S)-2-oxo-6-phenyl-2,3,6,7-tetrahydro-1H-azepin-3-yl]-L-alaninamide;

N²-[(3,5-difluorophenyl)acetyl]-N¹-[(3S)-1-methyl-2-oxo-5-phenyl-2,3,6,7-tetrahydro-1H-azepin-3-yl]-L-alaninamide;

N²-[(3,5-difluorophenyl)acetyl]-N¹-[(3S)-2-oxo-5-phenyl-2,3,6,7-tetrahydro-1H-azepin-3-yl]-L-alaninamide;

N²-[(2S)-2-(3,5-difluorophenyl)-2-hydroxyacetyl]-N¹-[(3S)-1-methyl-2-oxo-5-phenyl-2,3,6,7-tetrahydro-1H-azepin-3-yl]-L-alaninamide;

N²-[(2R)-2-(3,5-difluorophenyl)-2-hydroxyacetyl]-N¹-[(3S)-1-methyl-2-oxo-5-phenyl-2,3,6,7-tetrahydro-1H-azepin-3-yl]-L-alaninamide;

N²-[(2S)-2-(3,5-difluorophenyl)-2-hydroxyacetyl]-N¹-[(3S)-2-oxo-5-phenyl-2,3,6,7-tetrahydro-1H-azepin-3-yl]-L-alaninamide;

N²-[(2R)-2-(3,5-difluorophenyl)-2-hydroxyacetyl]-N¹-[(3S)-2-oxo-5-phenyl-2,3,6,7-tetrahydro-1H-azepin-3-yl]-L-alaninamide;

N²-[(3,5-difluorophenyl)acetyl]-N¹-[(3S)-1-methyl-2-oxo-4-phenyl-2,3,6,7-tetrahydro-1H-azepin-3-yl]-L-alaninamide;

N²-[(3,5-difluorophenyl)acetyl]-N¹-[(3S)-2-oxo-4-phenyl-2,3,6,7-tetrahydro-1H-azepin-3-yl]-L-alaninamide;

N²-[(2S)-2-(3,5-difluorophenyl)-2-hydroxyacetyl]-N¹-[(3S)-1-methyl-2-oxo-4-phenyl-2,3,6,7-tetrahydro-1H-azepin-3-yl]-L-alaninamide;

N²-[(2R)-2-(3,5-difluorophenyl)-2-hydroxyacetyl]-N¹-[(3S)-1-methyl-2-oxo-4-phenyl-2,3,6,7-tetrahydro-1H-azepin-3-yl]-L-alaninamide;

N²-[(2S)-2-(3,5-difluorophenyl)-2-hydroxyacetyl]-N¹-[(3S)-2-oxo-4-phenyl-2,3,6,7-tetrahydro-1H-azepin-3-yl]-L-alaninamide; and N²-[(2R)-2-(3,5-difluorophenyl)-2-hydroxyacetyl]-N¹-[(3S)-2-oxo-4-phenyl-2,3,6,7-tetrahydro-1H-azepin-3-yl]-L-alaninamide;

or pharmaceutically acceptable salt thereof.

23. A compound of formula (III):

(III)

wherein:

$R^1$ is selected from H, optionally substituted $C_{1-3}$alkylaryl, optionally substituted $C_{1-3}$alkylheterocycle, optionally substituted alkyl, optionally substituted $C_{3-6}$cycloalkyl, $C_{2-4}$alkylNR$^a$R$^b$, and —$C_{1-4}$alkyl-COR$^d$, wherein all such optional substitutions are made with 0, 1, 2 or 3 R$^e$;

$R^a$ and $R^b$ are, at each occurrence independently selected from H, $C_{1-4}$alkyl and $C_{5-6}$cycloalkyl, or $R^a$ and $R^b$ and the N to which they are attached in combination form a 5 or 6-membered N-linked heterocycle having 2 nitrogen or, 1 nitrogen and 1 oxygen, ring atoms, wherein the non-linked nitrogen is substituted with $R^c$;

$R^c$ is, at each occurrence independently selected from H, $C_{1-3}$alkyl, and substituted phenyl with 0, 1, 2, and 3 $R^e$;

$R^d$ is, at each occurrence independently selected from $C_{1-3}$alkyl, $C_{1-3}$alkoxy, and NR$^a$R$^b$;

$R^e$ is, at each occurrence independently selected from OH, F, Cl, Br, I, CN, NO$_2$, CF$_3$, $C_{1-6}$alkyl, and $C_{1-6}$alkoxy;

$R^2$, $R^3$ and $R^7$ are independently selected from H, optionally substituted $C_{1-3}$alkylaryl, optionally substituted $C_{1-3}$alkylheterocycle, optionally substituted 5- or 6-membered aromatic or heteroaromatic ring, said ring having 0, 1, 2 or 3, nitrogen, oxygen or sulfur atoms, but not more than 2 oxygen atoms or 2 sulfur atoms or 1 oxygen and 1 sulfur atom, optionally substituted $C_{1-6}$alkyl, and optionally substituted $C_{3-6}$ cycloalkyl, wherein all such optional substitutions are made with 0, 1, 2, and 3 R$^e$ moieties, with the requirement that one or more of $R^2$, $R^3$ and $R^7$ are aromatic or heteroaromatic;

$R^6$ is independently selected from H, optionally substituted $C_{1-3}$alkylaryl, optionally substituted $C_{1-3}$alkylheterocycle, optionally substituted $C_{1-6}$alkyl, and optionally substituted $C_{3-6}$ cycloalkyl, wherein all such optional substitutions are made with 0, 1, 2, or 3 R$^e$ moieties;

$R^4$ is H, optionally substituted 5- or 6-membered aromatic or heteroaromatic ring, said ring having 0, 1, 2 or 3, nitrogen, oxygen and sulfur atoms, but not more than 2 oxygen atoms or 2 sulfur atoms or 1 oxygen and 1 sulfur atom, $C_{1-6}$alkyl, $C_{3-6}$ cycloalkyl, or CR$^9$R$^{10}$R$^{11}$;

$R^5$ is —$C_{1-6}$alkyl, —$C_{1-3}$alkylR$^{12}$ or CH(OH)R$^{13}$;

$R^9$, $R^{10}$ and $R^{11}$ are, at each occurrence independently selected from H, F, $C_{1-4}$alkyl, OH, OCH$_3$, SH, SCH$_3$, and CH$_2$SCH$_3$;

$R^{12}$ is phenyl substituted with 0, 1, 2 and 3 $R^e$;

$R^{13}$ is $C_{1-6}$alkyl or $R^{12}$;

or a pharmaceutically acceptable salt thereof.

24. A compound of claim 23, wherein:
$R^1$ is selected from H, and optionally substituted alkyl, wherein such optional substitution is made with 0, 1, or 2 substituents selected from $C_{1-6}$cycloalkyl, $C_{1-6}$cycloalkoxy, and phenyl;
$R^2$, $R^3$, $R^6$ and $R^7$ are independently selected from H, and optionally substituted 6-membered aromatic, wherein such optional substitution is made with 0, 1, 2, or 3 $R^e$ moieties, with the requirement that one or more of $R^2$, $R^3$, $R^6$ and $R^7$ are aromatic;
$R^4$ is H, or $C_{1-6}$alkyl;
$R^5$ is —$C_{1-6}$alkyl or —$C_{1-3}$alkyl$R^{12}$;
$R^{12}$ is phenyl substituted with 0, 1, 2 or 3 $R^e$;
$R^e$ is, at each occurrence independently selected from OH, F, Cl, Br, I, CN, $NO_2$, $CF_3$, $C_{1-6}$alkyl, and $C_{1-6}$alkoxy;
or a pharmaceutically acceptable salt thereof.

25. A compound of claim 23, wherein:
$R^1$ is selected from H, —$C_{1-6}$alkyl, —$(CH_2)_2OCH_3$, —$CH_2$-phenyl, and —$CH_2C_{1-6}$cycloalkyl;
$R^2$, $R^3$, $R^6$ and $R^7$ are independently selected from H, and a substituted phenyl, wherein such substituent is selected from 1, 2, and 3 of the following F, Cl, Br, I and $OCH_3$;
$R^4$ is H, or $C_{1-6}$alkyl;
$R^5$ is —$C_{1-6}$alkyl or —$C_{1-3}$alkyl$R^{12}$ wherein $R^{12}$ is a substituted phenyl, wherein such substituent is selected from 1, 2 or 3 of the following F, Cl, Br, I and $OCH_3$;
or a pharmaceutically acceptable salt thereof.

26. A compound of claim 23, wherein:
$R^1$ is —$C_{1-6}$alkyl or —$CH_2C_{1-4}$cycloalkyl.

27. A compound of claim 23, wherein:
$R^1$ is methyl and —$CH_2$cyclopropane.

28. A compound of claim 23, wherein:
$R^e$ is, at each occurrence independently selected from F, Cl, $CF_3$, $C_{1-6}$alkyl, or $C_{1-6}$alkoxy.

29. A compound of claim 23, wherein:
$R^2$ is an optionally substituted phenyl, wherein such optional substitution is made with 0, 1, 2, or 3 $R^e$ moieties.

30. A compound of claim 23, wherein:
$R^3$, $R^6$ and $R^7$ are H.

31. A compound of claim 23, wherein:
$R^4$ is $C_{1-6}$alkyl.

32. A compound of claim 23, wherein:
$R^5$ is —$C_{1-6}$alkyl or —$C_{1-3}$alkyl$R^{12}$ wherein $R^{12}$ is a substituted phenyl, wherein such substituent is selected from 1, 2 and 3 of the following F, Cl, Br, I and $OCH_3$.

33. A compound of claim 23 selected from:
$N^2$-[(3,5-difluorophenyl)acetyl]-$N^1$-[(3S,7S)-1-methyl-2-oxo-7-phenylazepan-3-yl]-L-alaninamide;
$N^2$-[(3,5-difluorophenyl)acetyl]-$N^1$-[(3S,7R)-1-methyl-2-oxo-7-phenylazepan-3-yl]-L-alaninamide;
$N^2$-[(3,5-difluorophenyl)acetyl]-$N^1$-[(3R,7S)-1-methyl-2-oxo-7-phenylazepan-3-yl]-L-alaninamide;
$N^2$-[(3,5-difluorophenyl)acetyl]-$N^1$-[(3R,7R)-1-methyl-2-oxo-7-phenylazepan-3-yl]-L-alaninamide;
$N^2$-[(3,5-difluorophenyl)acetyl]-$N^1$-[(3S,7R)-2-oxo-7-phenylazepan-3-yl]-L-alaninamide;
$N^2$-[(2S)-2-(3,5-difluorophenyl)-2-hydroxyacetyl]-$N^1$-[(3S,7R)-1-methyl-2-oxo-7-phenylazepan-3-yl]-L-alaninamide;
$N^2$-[(2R)-2-(3,5-difluorophenyl)-2-hydroxyacetyl]-$N^1$-[(3S,7R)-1-methyl-2-oxo-7-phenylazepan-3-yl]-L-alaninamide;
$N^2$-[(2S)-2-(3,5-difluorophenyl)-2-hydroxyacetyl]-$N^1$-[(3S,7R)-2-oxo-7-phenylazepan-3-yl]-L-alaninamide;
$N^2$-[(2R)-2-(3,5-difluorophenyl)-2-hydroxyacetyl]-$N^1$-[(3S,7R)-2-oxo-7-phenylazepan-3-yl]-L-alaninamide;
$N^2$-[(3,5-difluorophenyl)acetyl]-$N^1$-[(3S,7S)-2-oxo-7-phenylazepan-3-yl]-L-alaninamide;
$N^2$-[(2S)-2-(3,5-difluorophenyl)-2-hydroxyacetyl]-$N^1$-[(3S,7S)-1-methyl-2-oxo-7-phenylazepan-3-yl]-L-alaninamide;
$N^2$-[(2R)-2-(3,5-difluorophenyl)-2-hydroxyacetyl]-$N^1$-[(3S,7S)-1-methyl-2-oxo-7-phenylazepan-3-yl]-L-alaninamide;
$N^2$-[(2S)-2-(3,5-difluorophenyl)-2-hydroxyacetyl]-$N^1$-[(3S,7S)-2-oxo-7-phenylazepan-3-yl]-L-alaninamide;
$N^2$-[(2R)-2-(3,5-difluorophenyl)-2-hydroxyacetyl]-$N^1$-[(3S,7S)-2-oxo-7-phenylazepan-3-yl]-L-alaninamide;
$N^2$-[(3,5-difluorophenyl)acetyl]-$N^1$-[(3S,6R)-1-methyl-2-oxo-6-phenylazepan-3-yl]-L-alaninamide;
$N^2$-[(3,5-difluorophenyl)acetyl]-$N^1$-[(3S,6R)-2-oxo-6-phenylazepan-3-yl]-L-alaninamide;
$N^2$-[(2S)-2-(3,5-difluorophenyl)-2-hydroxyacetyl]-$N^1$-[(3S,6R)-1-methyl-2-oxo-6-phenylazepan-3-yl]-L-alaninamide;
$N^2$-[(2R)-2-(3,5-difluorophenyl)-2-hydroxyacetyl]-$N^1$-[(3S,6R)-1-methyl-2-oxo-6-phenylazepan-3-yl]-L-alaninamide;
$N^2$-[(2S)-2-(3,5-difluorophenyl)-2-hydroxyacetyl]-$N^1$-[(3S,6R)-2-oxo-6-phenylazepan-3-yl]-L-alaninamide;
$N^2$-[(2R)-2-(3,5-difluorophenyl)-2-hydroxyacetyl]-$N^1$-[(3S,6R)-1-methyl-2-oxo-6-phenylazepan-3-yl]-L-alaninamide;
$N^2$-[(3,5-difluorophenyl)acetyl]-$N^1$-[(3S,6S)-1-methyl-2-oxo-6-phenylazepan-3-yl]-L-alaninamide;
$N^2$-[(3,5-difluorophenyl)acetyl]-$N^1$-[(3S,6S)-2-oxo-6-phenylazepan-3-yl]-L-alaninamide;
$N^2$-[(2S)-2-(3,5-difluorophenyl)-2-hydroxyacetyl]-$N^1$-[(3S,6S)-1-methyl-2-oxo-6-phenylazepan-3-yl]-L-alaninamide;
$N^2$-[(2R)-2-(3,5-difluorophenyl)-2-hydroxyacetyl]-$N^1$-[(3S,6S)-1-methyl-2-oxo-6-phenylazepan-3-yl]-L-alaninamide;
$N^2$-[(2S)-2-(3,5-difluorophenyl)-2-hydroxyacetyl]-$N^1$-[(3S,6S)-2-oxo-6-phenylazepan-3-yl]-L-alaninamide;
$N^2$-[(2R)-2-(3,5-difluorophenyl)-2-hydroxyacetyl]-$N^1$-[(3S,6S)-2-oxo-6-phenylazepan-3-yl]-L-alaninamide;
$N^2$-[(3,5-difluorophenyl)acetyl]-$N^1$-[(3S,4R)-1-methyl-2-oxo-4-phenylazepan-3-yl]-L-alaninamide;
$N^2$-[(3,5-difluorophenyl)acetyl]-$N^1$-[(3S,4R)-2-oxo-4-phenylazepan-3-yl]-L-alaninamide;
$N^2$-[(2S)-2-(3,5-difluorophenyl)-2-hydroxyacetyl]-$N^1$-[(3S,4R)-1-methyl-2-oxo-4-phenylazepan-3-yl]-L-alaninamide;
$N^2$-[(2R)-2-(3,5-difluorophenyl)-2-hydroxyacetyl]-$N^1$-[(3S,4R)-1-methyl-2-oxo-4-phenylazepan-3-yl]-L-alaninamide;
$N^2$-[(2S)-2-(3,5-difluorophenyl)-2-hydroxyacetyl]-$N^1$-[(3S,4R)-2-oxo-4-phenylazepan-3-yl]-L-alaninamide;
$N^2$-[(2R)-2-(3,5-difluorophenyl)-2-hydroxyacetyl]-$N^1$-[(3S,4R)-2-oxo-4-phenylazepan-3-yl]-L-alaninamide;
$N^2$-[(3,5-difluorophenyl)acetyl]-$N^1$-[(3S,4S)-1-methyl-2-oxo-4-phenylazepan-3-yl]-L-alaninamide;
$N^2$-[(3,5-difluorophenyl)acetyl]-$N^1$-[(3S,4S)-2-oxo-4-phenylazepan-3-yl]-L-alaninamide;
$N^2$-[(2S)-2-(3,5-difluorophenyl)-2-hydroxyacetyl]-$N^1$-[(3S,4S)-1-methyl-2-oxo-4-phenylazepan-3-yl]-L-alaninamide;
$N^2$-[(2R)-2-(3,5-difluorophenyl)-2-hydroxyacetyl]-$N^1$-[(3S,4S)-1-methyl-2-oxo-4-phenylazepan-3-yl]-L-alaninamide;

$N^2$-[(2S)-2-(3,5-difluorophenyl)-2-hydroxyacetyl]-$N^1$-[(3S,4S)-2-oxo-4-phenylazepan-3-yl]-L-alaninamide;

$N^2$-[(2R)-2-(3,5-difluorophenyl)-2-hydroxyacetyl]-$N^1$-[(3S,4S)-2-oxo-4-phenylazepan-3-yl]-L-alaninamide;

$N^2$-[(3,5-difluorophenyl)acetyl]-$N^1$-[(3S,4R,7S)-1-methyl-2-oxo-4,7-diphenylazepan-yl]-L-alaninamide;

$N^2$-[(3,5-difluorophenyl)acetyl]-$N^1$-[(3S,4R,7S)-2-oxo-4,7-diphenylazepan-3-yl]-L-alaninamide;

$N^2$-[(2S)-2-(3,5-difluorophenyl)-2-hydroxyacetyl]-$N^1$-[(3S,4R,7S)-1-methyl-2-oxo-4,7-diphenylazepan-3-yl]-L-alaninamide;

$N^2$-[(2R)-2-(3,5-difluorophenyl)-2-hydroxyacetyl]-$N^1$-[(3S,4R,7S)-1-methyl-2-oxo-4,7-diphenylazepan-3-yl]-L-alaninamide;

$N^2$-[(2S)-2-(3,5-difluorophenyl)-2-hydroxyacetyl]-$N^1$-[(3S,4R,7S)-2-oxo-4,7-diphenylazepan-3-yl]-L-alaninamide;

$N^2$-[(2R)-2-(3,5-difluorophenyl)-2-hydroxyacetyl]-$N^1$-[(3S,4R,7S)-2-oxo-4,7-diphenylazepan-3-yl]-L-alaninamide;

$N^2$-[(3,5-difluorophenyl)acetyl]-$N^1$-[(3S,4S,7S)-1-methyl-2-oxo-4,7-diphenylazepan-3-yl]-L-alaninamide;

$N^2$-[(3,5-difluorophenyl)acetyl]-$N^1$-[(3S,4S,7S)-2-oxo-4,7-diphenylazepan-3-yl]-L-alaninamide;

$N^2$-[(2S)-2-(3,5-difluorophenyl)-2-hydroxyacetyl]-$N^1$-[(3S,4S,7S)-1-methyl-2-oxo-4,7-diphenylazepan-3-yl]-L-alaninamide;

$N^2$-[(2R)-2-(3,5-difluorophenyl)-2-hydroxyacetyl]-$N^1$-[(3S,4S,7S)-1-methyl-2-oxo-4,7-diphenylazepan-3-yl]-L-alaninamide;

$N^2$-[(2S)-2-(3,5-difluorophenyl)-2-hydroxyacetyl]-$N^1$-[(3S,4S,7S)-2-oxo-4,7-diphenylazepan-3-yl]-L-alaninamide;

$N^2$-[(2R)-2-(3,5-difluorophenyl)-2-hydroxyacetyl]-$N^1$-[(3S,4S,7S)-2-oxo-4,7-diphenylazepan-3-yl]-L-alaninamide;

$N^2$-[(3,5-difluorophenyl)acetyl]-$N^1$-[(3S,4R,7R)-1-methyl-2-oxo-4,7-diphenylazepan-3-yl]-L-alaninamide;

$N^2$-[(3,5-difluorophenyl)acetyl]-$N^1$-[(3S,4R,7R)-2-oxo-4,7-diphenylazepan-3-yl]-L-alaninamide;

$N^2$-[(2S)-2-(3,5-difluorophenyl)-2-hydroxyacetyl]-$N^1$-[(3S,4R,7R)-1-methyl-2-oxo-4,7-diphenylazepan-3-yl]-L-alaninamide;

$N^2$-[(2R)-2-(3,5-difluorophenyl)-2-hydroxyacetyl]-$N^1$-[(3S,4R,7R)-1-methyl-2-oxo-4,7-diphenylazepan-3-yl]-L-alaninamide;

$N^2$-[(2S)-2-(3,5-difluorophenyl)-2-hydroxyacetyl]-$N^1$-[(3S,4R,7R)-2-oxo-4,7-diphenylazepan-3-yl]-L-alaninamide;

$N^2$-[(2R)-2-(3,5-difluorophenyl)-2-hydroxyacetyl]-$N^1$-[(3S,4R,7R)-2-oxo-4,7-diphenylazepan-3-yl]-L-alaninamide;

$N^2$-[(3,5-difluorophenyl)acetyl]-$N^1$-[(3S,4R,6S)-1-methyl-2-oxo-4,6-diphenylazepan-3-yl]-L-alaninamide;

$N^2$-[(3,5-difluorophenyl)acetyl]-$N^1$-[(3S,4R,6S)-2-oxo-4,6-diphenylazepan-3-yl]-L-alaninamide;

$N^2$-[(2S)-2-(3,5-difluorophenyl)-2-hydroxyacetyl]-$N^1$-[(3S,4R,6S)-1-methyl-2-oxo-4,6-diphenylazepan-3-yl]-L-alaninamide;

$N^2$-[(2R)-2-(3,5-difluorophenyl)-2-hydroxyacetyl]-$N^1$-[(3S,4R,6S)-1-methyl-2-oxo-4,6-diphenylazepan-3-yl]-L-alaninamide;

$N^2$-[(2S)-2-(3,5-difluorophenyl)-2-hydroxyacetyl]-$N^1$-[(3S,4R,6S)-2-oxo-4,6-diphenylazepan-3-yl]-L-alaninamide;

$N^2$-[(2R)-2-(3,5-difluorophenyl)-2-hydroxyacetyl]-$N^1$-[(3S,4R,6S)-2-oxo-4,6-diphenylazepan-3-yl]-L-alaninamide;

$N^2$-[(3,5-difluorophenyl)acetyl]-$N^1$-[(3S,4S,6S)-1-methyl-2-oxo-4,6-diphenylazepan-3-yl]-L-alaninamide;

$N^2$-[(3,5-difluorophenyl)acetyl]-$N^1$-[(3S,4S,6S)-2-oxo-4,6-diphenylazepan-3-yl]-L-alaninamide;

$N^2$-[(2S)-2-(3,5-difluorophenyl)-2-hydroxyacetyl]-$N^1$-[(3S,4S,6S)-1-methyl-2-oxo-4,6-diphenylazepan-3-yl]-L-alaninamide;

$N^2$-[(2R)-2-(3,5-difluorophenyl)-2-hydroxyacetyl]-$N^1$-[(3S,4S,6S)-1-methyl-2-oxo-4,6-diphenylazepan-3-yl]-L-alaninamide;

$N^2$-[(2S)-2-(3,5-difluorophenyl)-2-hydroxyacetyl]-$N^1$-[(3S,4S,6S)-2-oxo-4,6-diphenylazepan-3-yl]-L-alaninamide;

$N^2$-[(2R)-2-(3,5-difluorophenyl)-2-hydroxyacetyl]-$N^1$-[(3S,4S,6S)-2-oxo-4,6-diphenylazepan-3-yl]-L-alaninamide;

$N^2$-[(3,5-difluorophenyl)acetyl]-$N^1$-[(3S,4R,6R)-1-methyl-2-oxo-4,6-diphenylazepan-3-yl]-L-alaninamide;

$N^2$-[(3,5-difluorophenyl)acetyl]-$N^1$-[(3S,4R,6R)-2-oxo-4,6-diphenylazepan-3-yl]-L-alaninamide;

$N^2$-[(2S)-2-(3,5-difluorophenyl)-2-hydroxyacetyl]-$N^1$-[(3S,4R,6R)-1-methyl-2-oxo-4,6-diphenylazepan-3-yl]-L-alaninamide;

$N^2$-[(2R)-2-(3,5-difluorophenyl)-2-hydroxyacetyl]-$N^1$-[(3S,4R,6R)-1-methyl-2-oxo-4,6-diphenylazepan-3-yl]-L-alaninamide;

$N^2$-[(2S)-2-(3,5-difluorophenyl)-2-hydroxyacetyl]-$N^1$-[(3S,4R,6R)-2-oxo-4,6-diphenylazepan-3-yl]-L-alaninamide;

$N^2$-[(2R)-2-(3,5-difluorophenyl)-2-hydroxyacetyl]-$N^1$-[(3S,4R,6R)-2-oxo-4,6-diphenylazepan-3-yl]-L-alaninamide;

$N^2$-[(3,5-difluorophenyl)acetyl]-$N^1$-[(3S,5R,7S)-1-methyl-2-oxo-5,7-diphenylazepan-3-yl]-L-alaninamide;

$N^2$-[(3,5-difluorophenyl)acetyl]-$N^1$-[(3S,5R,7S)-2-oxo-5,7-diphenylazepan-3-yl]-L-alaninamide;

$N^2$-[(2S)-2-(3,5-difluorophenyl)-2-hydroxyacetyl]-$N^1$-[(3S,5R,7S)-1-methyl-2-oxo-5,7-diphenylazepan-3-yl]-L-alaninamide;

$N^2$-[(2R)-2-(3,5-difluorophenyl)-2-hydroxyacetyl]-$N^1$-[(3S,5R,7S)-1-methyl-2-oxo-5,7-diphenylazepan-3-yl]-L-alaninamide;

$N^2$-[(2S)-2-(3,5-difluorophenyl)-2-hydroxyacetyl]-$N^1$-[(3S,5R,7S)-2-oxo-5,7-diphenylazepan-3-yl]-L-alaninamide;

$N^2$-[(2R)-2-(3,5-difluorophenyl)-2-hydroxyacetyl]-$N^1$-[(3S,5R,7S)-2-oxo-5,7-diphenylazepan-3-yl]-L-alaninamide;

$N^2$-[(3,5-difluorophenyl)acetyl]-$N^1$-[(3S,5S,7S)-1-methyl-2-oxo-5,7-diphenylazepan-3-yl]-L-alaninamide;

$N^2$-[(3,5-difluorophenyl)acetyl]-$N^1$-[(3S,5S,7S)-2-oxo-5,7-diphenylazepan-3-yl]-L-alaninamide;

$N^2$-[(2S)-2-(3,5-difluorophenyl)-2-hydroxyacetyl]-$N^1$-[(3S,5S,7S)-1-methyl-2-oxo-5,7-diphenylazepan-3-yl]-L-alaninamide;

$N^2$-[(2R)-2-(3,5-difluorophenyl)-2-hydroxyacetyl]-$N^1$-[(3S,5S,7S)-1-methyl-2-oxo-5,7-diphenylazepan-3-yl]-L-alaninamide;

$N^2$-[(2S)-2-(3,5-difluorophenyl)-2-hydroxyacetyl]-$N^1$-[(3S,5S,7S)-2-oxo-5,7-diphenylazepan-3-yl]-L-alaninamide;

$N^2$-[(2R)-2-(3,5-difluorophenyl)-2-hydroxyacetyl]-$N^1$-[(3S,5S,7S)-2-oxo-5,7-diphenylazepan-3-yl]-L-alaninamide;

N²-[(3,5-difluorophenyl)acetyl]-N¹-[(3S,5R,7R)-1-methyl-2-oxo-5,7-diphenylazepan-3-yl]-L-alaninamide;
N²-[(3,5-difluorophenyl)acetyl]-N¹-[(3S,5R,7R)-2-oxo-5,7-diphenylazepan-3-yl]-L-alaninamide;
N²-[(2S)-2-(3,5-difluorophenyl)-2-hydroxyacetyl]-N¹-[(3S,5R,7R)-1-methyl-2-oxo-5,7-diphenylazepan-3-yl]-L-alaninamide;
N²-[(2R)-2-(3,5-difluorophenyl)-2-hydroxyacetyl]-N¹-[(3S,5R,7R)-1-methyl-2-oxo-5,7-diphenylazepan-3-yl]-L-alaninamide;
N²-[(2S)-2-(3,5-difluorophenyl)-2-hydroxyacetyl]-N¹-[(3S,5R,7R)-2-oxo-5,7-diphenylazepan-3-yl]-L-alaninamide;
N²-[(2R)-2-(3,5-difluorophenyl)-2-hydroxyacetyl]-N¹-[(3S,5R,7R)-2-oxo-5,7-diphenylazepan-3-yl]-L-alaninamide;
N²-[(3,5-difluorophenyl)acetyl]-N¹-[(3S,5S)-1-methyl-2-oxo-5-phenylazepan-3-yl]-L-alaninamide;
N²-[(3,5-difluorophenyl)acetyl]-N¹-[(3S,5S)-2-oxo-5-phenylazepan-3-yl]-L-alaninamide;
N²-[(2S)-2-(3,5-difluorophenyl)-2-hydroxyacetyl]-N¹-[(3S,5S)-1-methyl-2-oxo-5-phenylazepan-3-yl]-L-alaninamide;
N²-[(2R)-2-(3,5-difluorophenyl)-2-hydroxyacetyl]-N¹-[(3S,5S)-1-methyl-2-oxo-5-phenylazepan-3-yl]-L-alaninamide;
N²-[(2S)-2-(3,5-difluorophenyl)-2-hydroxyacetyl]-N¹-[(3S,5S)-2-oxo-5-phenylazepan-3-yl]-L-alaninamide;
N²-[(2R)-2-(3,5-difluorophenyl)-2-hydroxyacetyl]-N¹-[(3S,5S)-2-oxo-5-phenylazepan-3-yl]-L-alaninamide;
N²-[(3,5-difluorophenyl)acetyl]-N¹-[(3S,5R)-1-methyl-2-oxo-5-phenylazepan-3-yl]-L-alaninamide;
N²-[(3,5-difluorophenyl)acetyl]-N¹-[(3S,5R)-2-oxo-5-phenylazepan-3-yl]-L-alaninamide;
N²-[(2S)-2-(3,5-difluorophenyl)-2-hydroxyacetyl]-N¹-[(3S,5R)-1-methyl-2-oxo-5-phenylazepan-3-yl]-L-alaninamide;
N²-[(2R)-2-(3,5-difluorophenyl)-2-hydroxyacetyl]-N¹-[(3S,5R)-1-methyl-2-oxo-5-phenylazepan-3-yl]-L-alaninamide;
N²-[(2S)-2-(3,5-difluorophenyl)-2-hydroxyacetyl]-N¹-[(3S,5R)-2-oxo-5-phenylazepan-3-yl]-L-alaninamide; and
N²-[(2R)-2-(3,5-difluorophenyl)-2-hydroxyacetyl]-N¹-[(3S,5R)-2-oxo-5-phenylazepan-3-yl]-L-alaninamide;
or pharmaceutically acceptable salt thereof.

34. A pharmaceutical composition comprising a compound of claim 1 or a pharmaceutically acceptable salt thereof, together with at least one pharmaceutically acceptable carrier, diluent or excipient.

35. A process for preparing a compound of formula 1f

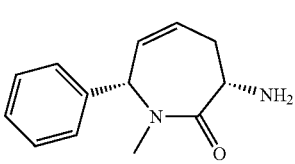

1f comprising reacting tert-butyl[(3S,7S)-1-methyl-2-oxo-7-phenyl-2,3,4,7-tetrahydro-1H-azepin-3-yl]carbamate with triflouroacetic acid.

36. A process for preparing a compound of formula 1

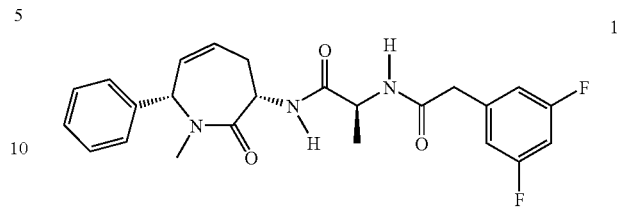

1 comprising reacting a compound of formula 1f

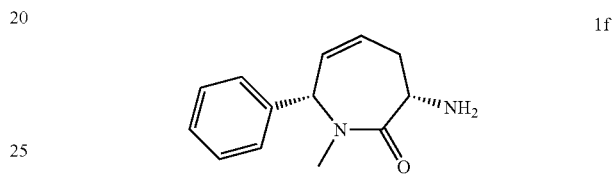

1f and N-[(3,5-difluorophenyl)acetyl]-L-alanine with HOBt-hydrate, and N-methyl morpholine.

37. A process for preparing a compound of formula 2e

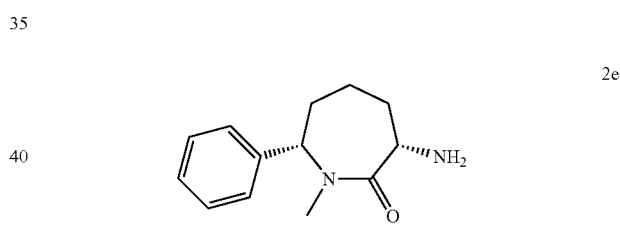

2e comprising reacting benzyl [(3S,7S)-1-methyl-2-oxo-7-phenyl-2,3,4,7-tetrahydro-1H-azepin-3-yl]carbamate with H₂ and Pearlman's Catalyst in ethanol.

38. A process for preparing a compound of formula 2

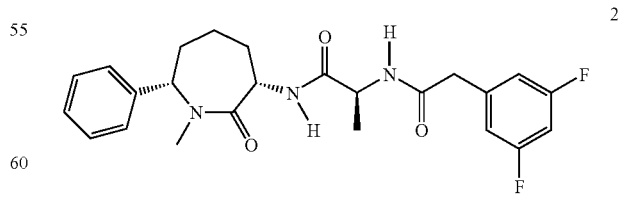

2 comprising reacting (3S,7S)-3-amino-1-methyl-7-phenylazepan-2-one and N-[(3,5-difluorophenyl)acetyl]-L-alanine with HOBt-hydrate, EDAC.HCl and N-methyl morpholine.

39. A process for preparing (3R,7S)-3-amino-1-(cyclopropylmethyl)-7-(4-methoxyphenyl)-1,3,4,7-tetrahydro-2H-azepin-2-one comprising reacting a compound of formula 11d

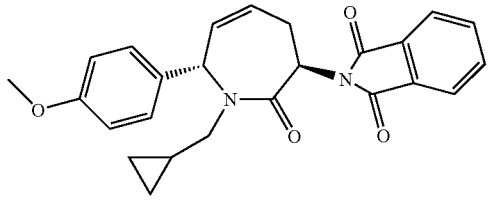

with H$_2$NNH$_2$ in methanol.

40. A process for preparing a compound of formula 11A

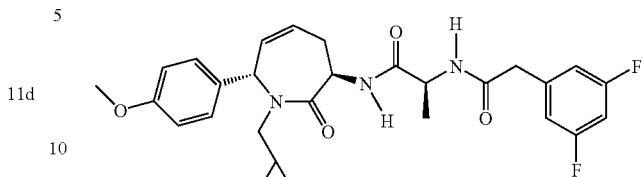

comprising reacting (3R,7S)-3-amino-1-(cyclopropylmethyl)-7-(4-methoxyphenyl)-1,3,4,7-tetrahydro-2H-azepin-2-one and N-[(3,5-difluorophenyl)acetyl]-L-alanine with with HOBt-hydrate, EDAC.HCl and N-methyl morpholine.

* * * * *